US012716077B2

(12) United States Patent
Houston et al.

(10) Patent No.: US 12,716,077 B2
(45) Date of Patent: Aug. 25, 2026

(54) FERMENTATIVE PRODUCTION OF ISOPRENOIDS

(71) Applicant: DSM IP ASSETS B.V., Heerlen (NL)

(72) Inventors: Peter Louis Houston, Kaiseraugst (CH); Valmik Kanubhai Vyas, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 516 days.

(21) Appl. No.: 18/251,189

(22) PCT Filed: Nov. 1, 2021

(86) PCT No.: PCT/EP2021/080282

§ 371 (c)(1),
(2) Date: Apr. 28, 2023

(87) PCT Pub. No.: WO2022/090548

PCT Pub. Date: May 5, 2022

(65) Prior Publication Data

US 2023/0407344 A1 Dec. 21, 2023

Related U.S. Application Data

(60) Provisional application No. 63/107,898, filed on Oct. 30, 2020.

(51) Int. Cl.
*C12P 23/00* (2006.01)
*C12P 5/00* (2006.01)

(52) U.S. Cl.
CPC .................................... *C12P 5/007* (2013.01)

(58) Field of Classification Search
CPC .. C12P 23/00; C12P 5/00; C12P 5/007; C12R 2001/645
See application file for complete search history.

(56) References Cited

U.S. PATENT DOCUMENTS

2014/0170720 A1 6/2014 Kim et al.
2016/0130628 A1 5/2016 Kim
2023/0407344 A1* 12/2023 Houston ................. C12P 5/007

FOREIGN PATENT DOCUMENTS

| | | | |
|---|---|---|---|
| WO | 2006102342 | A3 | 10/2007 |
| WO | 2008042338 | A3 | 10/2008 |
| WO | 2014096992 | A1 | 6/2014 |
| WO | 2016172282 | A1 | 10/2016 |
| WO | 2019057999 | A1 | 3/2019 |
| WO | 2019058000 | A1 | 3/2019 |
| WO | 2019058001 | A1 | 3/2019 |
| WO | 2020141168 | A1 | 7/2020 |

OTHER PUBLICATIONS

Ausubel et al., Current Protocols in Molecular Biology, Wiley Online Library, Printed May 9, 2019, 5 pages.

Brennan et al., Alleviating Monoterpene Toxicity Using a Two-Phase Extractive Fermentation for the Bioproduction of Jet Fuel Mixtures in *Saccharomyces cere visiae*, Biotechnology and Bioengineering, May 28, 2012, pp. 2513-2522, vol. 109, No. 10.

Creuly et al., Bioconversion of fatty acids into methyl ketones by spores of Pen icillium roquefortii in a water-organic solvent, two-phase system, Enzyme and Microbial Technology, Aug. 1, 1992, pp. 669-678, vol. 14, No. 8.

Dujon et al., Genome evolution in yeasts, Nature, Jul. 2004, 10 pages, vol. 430.

Frohwritter et al., Production of the sesquiterpene ()-valencene by metabolically engineered Corynebacterium glutamicum, Journal of Biotechnology, Jun. 6, 2014, pp. 205-213, vol. 191.

Jang et al., Comparison of extraction phases for a two-phase culture of a recombinant *E. coli* producing retinoids, Biotechnology Letters, Mar. 1, 2014, pp. 497-505, vol. 36, No. 3.

Jang et al., Retinoid production using metabolically engineered *Escherichia coil* with a two-phase culture system, Microbial Cell Factories, 2011, 12 pages.

Jang et al., Selective Retinol Production by Modulating the Composition of Retinoids From Metabolically Engineered *E. coli*, Biotechnology and Bioegineering, May 12, 2015, pp. 1604-1612, vol. 112, No. 8.

Johnson et al., Safety Assessment of Isoparaffins as Used in Cosmetics, International Journal of Technology, Jun. 29, 2017, 27 pages.

Kang et al., Biosynthesis of pinene from glucose using metabolicallyengineered Cotynebacterium glutamicum, Biotechnology Letters, Jun. 15, 2014, pp. 2069-2077, vol. 36, No. 10, Kluwer Academic Publishers.

Needleman et al., A General Method Applicable to the Search for Similarities in the Amino Acid Sequence of Two Proteins, Department of Biochemistry, Northwestern University, and Nuclear Medicine Service,, Published 1970, pp. 443-453, vol. 48.

Newman et al., High-Level Production of Amorpha 4,11-Diene in a Two-Phase Partitioning Bioreactor of Metabolically Engineered *Escherichia coli*, Biotechnology and Bioengineering, Jan. 1, 2006, pp. 684-691, vol. 95.

Rice Peter, EMBOSS: The European Molecular Biology Open Software Suite, The European Molecular Biology Open Software Suite, Jun. 2006, 2 pages, vol. 16, No. 6.

Sambrook et al., Molecular Cloning, A Laboratory Manual, 30 pages, Second edition.

Schewe et al., Bioprocess Engineering for Microbial Synthesis and Conversion of Isoprenoids, Advances in Biochemical Engineering, Jan. 1, 2015, pp. 251-286, vol. 148.

Sun et al., Vitamin A Production by Engineered *Saccharomyces cerevisiae* from Xylose via Two-Phase in Situ Extraction, ACS Synthetic Biology, Sep. 20, 2019, vol. 8, No. 9.

(Continued)

*Primary Examiner* — Tekchand Saidha
(74) *Attorney, Agent, or Firm* — Nixon & Vanderhye, PC

(57) ABSTRACT

The present invention is related to fermentative production of isoprenoids, comprising cultivation of a suitable host cell, such as fungal host cell, particularly oleaginous host cell, in an improved two-phase culture system.

13 Claims, No Drawings

Specification includes a Sequence Listing.

(56) References Cited

OTHER PUBLICATIONS

Swiss Institute of Bioinformatics, Scan Prosite—user manual, Prosite, Date unknown, 8 pages.
International Search Report for PCT/EP2021/080282 mailed Feb. 14, 2022, 7 pages.
Written Opinion of the ISA for PCT/EP2021/080282 mailed Feb. 14, 2022, 12 pages.

* cited by examiner

FERMENTATIVE PRODUCTION OF ISOPRENOIDS

This application is the U.S. national phase of International Application No. PCT/EP2021/080282 filed Nov. 1, 2021 which designated the U.S. and claims priority to U.S. 63/107,898 filed Oct. 30, 2020, the entire contents of each of which are hereby incorporated by reference.

The present invention is related to fermentative production of isoprenoids, comprising cultivation of a suitable host cell, such as fungal host cell, particularly oleaginous host cell, in an improved two-phase culture system. Current chemical production methods for isoprenoids with less than C40 carbon backbone, such as apocarotenoids, including but not limited to vitamin, have some undesirable characteristics such as e.g. high-energy consumption, complicated purification steps and/or undesirable by-products. Therefore, over the past decades, other approaches to manufacture these compounds, comprising microbial conversion steps have been investigated, which would lead to more economical as well as ecological production.

In general, the biological systems that produce the herein defined isoprenoids are industrially intractable and/or produce the compounds at such low levels that commercial scale isolation is not practical. The most limiting factors include instability of intermediates in such biological systems and/or the relatively high production of by-products. As an example, formation of fatty acid retinyl esters (FAREs) in fermentative production of vitamin A, particularly using oleaginous host cells grown on triglycerides, is an important limiting factor in the process towards bio-based vitamin A/retinol.

In order to circumvent some of these issues in fermentative production of isoprenoids with less than 40 carbons as backbone, so-called two-phase cultivation systems have been developed, wherein the fermentation products are collected outside the cell in the so-called second phase comprising lipophilic solvents such as e.g. Drakeol®, silicone oil or n-dodecane (see WO2020/141168 or Jang et al., Microbial Cell Factories 10:59, 2011). However, the yield as well as impurity profile with the known solvents is not satisfactory.

Thus, it is an ongoing task to look for more efficient production processes using the two-phase culture system, in particular to look for solvents with improved properties.

Surprisingly, we now identified an improved process for fermentative production of isoprenoids with less than 40 carbons as backbone, including apocarotenoids, using a two-phase culture system, wherein second phase solvents collecting the fermentation products are used that are not lost/disappearing during the fermentation and thus can lead to increased productivity and/or improved purity of the fermentation products.

Particularly, the present invention is directed to a two-phase culture system including an in vitro extraction system for fermentative production of isoprenoids with less than 40 carbons as backbone ("<C40-isoprenoids") including apocarotenoids, such as e.g. retinoids, sesquiterpenes, diterpenes or ionones, including but not limited to alpha-farnesene, abienol, alpha- and beta-ionone, wherein a suitable host cell, particularly fungal host cell, such as e.g. an oleaginous yeast, e.g. *Yarrowia* or *Saccharomyces*, is grown on a suitable carbon source and in the presence of a lipophilic solvent that is not disappearing during the fermentation.

A suitable lipophilic solvent, i.e. second phase solvent, with minimal loss and/or disappearance during the fermentation as defined herein and to be used for the present invention might be selected from isoparaffins comprising mixtures of alkanes, cycloparaffin, isoalkanes, cycloalkanes, or dodecanes. The solvents might be natural or synthetic ones. Examples of commercially available useful solvents might be selected from Total, e.g. Isane® solvents, Shell, e.g. ShellSolTD or ShellSolT, Exxon Mobile, e.g. Isopar™ fluids, particularly such as e.g. Isopar™ M, Isopar™ N, Isopar™ H, Isopar™ K, Isopar™ L, or mixtures thereof or mixtures with iso-dodecane isomers, as e.g. commercially available under the tradename AC365770010 (Acros Organics). Preferably, the second phase solvent is selected from isoparaffins comprising, e.g. Isopar™ M, Isopar™ N, Isopar™ H, Isopar™ K, Isopar™ L, and mixtures thereof, more preferably comprising Isopar™ N, Isopar™ L and/or Isopar™ M.

Further suitable lipophilic solvents, i.e. second phase solvents, with minimal loss and/or disappearance during the fermentation as defined herein and to be used for the present invention might be selected from lipophilic solvents comprising mixtures of n-alkanes, isoalkanes, hydrocarbons. The solvents might be natural or synthetic ones. Examples of commercially available useful solvents might be selected from Exxon Mobil, as e.g. commercially available under the tradenames Exxsol™ D60, D80, D95 or D110.

It is understood that useful solvents include the above listed commercially available solvents as well as the respective solvents with the same or equivalent properties but known/available from other suppliers.

As used herein, a solvent has equivalent or identical properties as Isopar™ fluids, including Isopar™ M, Isopar™ H, Isopar™ K, Isopar™ L, and is defined as branched-chain isomers, preferably terminally methylated form of a straight-chain alkane, which contain six to twenty six carbons, perhaps chemically coupled from smaller alkane precursors in strong acid, hydrogenated with $H_2$ and catalyst, such as nickel or platinum, to remove unsaturation and trace aromatics. These are known in current industrial suppliers as Isopar™ (Exxon Mobil Chemical), Soltrol™ (Chevron Phillips Chemical Company), Shellsol™ OMS (Royal Dutch Shell), iso-octane and iso-dodecane. Specifically, the use of Isopar™ M is preferred. The use of these in consumer products is outlined in a review by Johnson et al., Int J Toxicol. 2012 Nov-Dec;31 (6 Suppl): 269S-95S.

As used herein, a solvent has equivalent or identical properties as Exxsol™ D60, D80, D95, D110. These Exxsol™ Ds are narrow boiling distillation cuts from cracked hydrocarbons that have been reduced by catalytic hydrogenation to remove aromatics and unsaturation.

A suitable <C40-isoprenoid that is produced in the two-phase culture system according to the present invention might be selected from isoprenoids, including but not limited to retinoids, e.g. retinol, retinal, retinyl acetate, including 4-keto- and 3-hydroxy-forms, alpha-ionone, beta-ionone, including dihydroxy forms, santalol, valencene, nootkatone, patchoulol, alpha-farnesene, abienol, steviol, i.e. fermentation products, typically 15 to 30 carbons in length, that can pass through the cell wall of the host cell to be collected outside the cell in the second phase solvent as defined herein.

As used herein, the term "not disappearing" in connection with the second phase solvents as defined herein means that the same amount of solvent present at the start of the fermentation is still detectable at the end of the fermentation process. A loss or disappearance of solvent might be due to e.g. consumption by the host cell and/or evaporation during the fermentation. The terms "loss" or "disappearance" are used interchangeably herein. Such solvent as used for the process of the present invention is also called a "stable" solvent. Thus, a stable solvent according to the present invention means a loss or disappearance of the solvent during the fermentation in the range of about 20% or less, e.g. in the range of about 20, 15, 10, 8, 5, 3, 2, 1% or even no loss or disappearance of the solvent during the fermentation.

In one embodiment of the present invention, the two-phase culture system as defined herein, including the use of the solvents as defined herein, results in a disappearance of solvents of about 20% or less, i.e, wherein at least about 80%, such as e.g. 85, 90, 92, 95, 97, 98, 99, 100% of solvent present at the start of the fermentation is still present at the end of the fermentation process. Particularly useful solvents that are still present at the end of the fermentation might be selected from solvents identical or equivalent to Isopar™ M, L, H, K or Exxsol™ D110.

Thus, the present invention is directed to fermentative production of <C40-isoprenoids including but not limited to apocarotenoids, sesquiterpenes, diterpenes or ionones, comprising cultivating a suitable host cell as defined herein under suitable culture conditions in a two-phase culture system, in the presence of a solvent as defined herein with a loss of solvent of about 20% or less during the fermentation.

As used herein, the term "solvent comprising isoparaffins" or "solvent comprising mixtures of alkanes" means that the percentage of isoparaffins and/or mixtures of alkanes is at least in the range of about 90%, preferably in the range of about 95, 98, 99, or 100% (v/v), including the solvents described herein, particularly solvents known under the tradename Isopar™ M, Isopar™ N, Isopar™ H, Isopar™ K, Isopar™ L, Exxsol™ D60, D80, D95, D110 or solvents with equivalent or identical properties but from other suppliers. Such range might be also applicable to solvents comprising other lipophilic compounds, such as e.g. a solvent comprising n-dodecane, silicone oil, hexadecane or Drakeol®. The use of a solvent with a percentage of isoparaffins and/or mixtures of alkanes as defined herein is used interchangeably with the term "in the presence of a lipophilic solvent".

In one embodiment, the present invention is related to a process for reducing or abolishing the consumption of the second phase solvent, i.e. consumption of the second phase solvent by the host cell, as compared to consumption using n-dodecane as second phase. Particularly, the consumption of the second phase might be reduced by at least about 50%, such as e.g. 60, 65, 70, 75, 80, 85, 90, 95, 97, 99 or 100% compared to consumption using n-dodecane as second phase solvent via a process using a lipophilic solvent as described herein. Preferably, the lipophilic solvent is selected from solvents known under the tradename Isopar™ M, Isopar™ N, Isopar™ H, Isopar™ K, Isopar™ L, Exxsol™ D110 or solvents with equivalent or identical properties but from other suppliers.

In a further embodiment, the present invention is related to a two-phase culture system for fermentative production of <C40-isoprenoids as defined herein in the presence of a lipophilic solvent as described herein, wherein the evaporation of the solvent is reduced or abolished, particularly reduced by at least about 50%, such as e.g. 60, 65, 70, 75, 80, 85, 90, 95, 97, 99 or 100%. Preferably, the lipophilic solvent is selected from solvents known under the tradename Isopar™ M, Isopar™ N, Isopar™ H, Isopar™ K, Isopar™ L, Exxsol™ D60, Exxsol™ D110, more preferably Isopar™ L, Isopar™ M, Exxsol™ D110, or solvents with equivalent or identical properties but from other suppliers.

Thus, a stable solvent according to the present invention means that the evaporation and/or consumption is reduced by at least about 50% compared to known solvents such as e.g. n-dodecane, silicone oil or hexadecane. Such solvents with increased evaporations and/or consumption during the fermentation in the range of about more than 50% compared to the stable solvents as defined herein are defined as "non-stable solvents". Examples of such non-stable solvents are n-dodecane, silicone oil or hexadecane.

Evaporation of a solvent used in a two-phase culture system, including the measurement of mass of fermentation over time, and measurement of second phase volume at the beginning and end of the fermentation can be measured by mass balancing using LCMS. Further the measurement of incorporation of second phase into the product, such as e.g. retinyl acetate, indicates consumption. Measurement of isotopic $^{13}C$ ratios in product weighted towards the ratio in petrol vs the corn derived ethanol feed can be done by $^{13}C$ NMR or mass spectroscopy. Consumption of the solvent, such as e.g. isoparaffins, according to the present invention by the host organism, such as e.g. *Yarrowia*, is detection of oxygen consumption (measured by a dissolved oxygen probe) in the presence of the second phase in the absence of another carbon source, wherein consumption of oxygen above the background being the same as with no solvent correlates with consumption of the solvent. Finally, measurement/mass spec analysis of off-gas or condensation in a cold trap from fermentation can be used to measure evaporation.

In one embodiment the present invention features a fermentative process for production of <C40-isoprenoids as defined herein using a two-phase culture system, wherein the formation of by-products could be reduced, particularly reduced by at least about 10% in comparison to the use of a non-stable solvent, such as e.g. in the range of about 15, 20, 25, 30, 35, 40, 45, 50% or more. Particularly, such process for reducing the formation of by-products as defined herein is performed in the presence of a lipophilic solvent as defined herein, preferably wherein the solvent is selected from solvents known under the tradename Isopar™ M, Isopar™ N, Isopar™ L, Exxsol™ D60, Exxsol™ D95, Exxsol™ D110, more preferably Isopar™ M, Exxsol™ D60, Exxsol™ D95, Exxsol™ D110, or solvents with equivalent or identical properties but from other suppliers. Compared to the use of n-dodecane or Drakeol®, the reduction might be in the range of a least about 25%.

As used herein, the terms "by-products", "side-products" or "undesired fermentation products" in connection with fermentative production of <C40-isoprenoids according to the present invention are used interchangeably herein and refer to undesired co-production of competing products, i.e. impurities, which have to be separated from the desired fermentation products and/or limit the yield and/or productivity of the desired fermentation products. Furthermore, it relates to undesired conversion processes, i.e, wherein the conversion of an intermediate into the desired fermentation product is competing with undesired conversion of the intermediate into a side-product or undesired by-product. The terms <C-40 isoprenoids and (desired) fermentation products are used interchangeably herein.

With regards to production of retinoids, particularly production of retinyl acetate, as an example of an apocarotenoid which is included in the present invention, undesired side-products include but are not limited to formation of retinal, retinol, fatty acid retinyl esters (FAREs) or dihydro-forms such as e.g. dihydro-retinol or dihydro-retinyl acetate, particularly FAREs, which should be reduced or abolished.

With regards to production of ionones, such as e.g. alpha-ionone or beta-ionone, as a further example of an apocarotenoid which is included in the present invention, undesired side-products include but are not limited to formation of rosafluene, phytoene, ergosterol, dihydro-beta-ionone, and other reduced forms.

In a particular aspect of the present invention, the two-phase culture system as described herein is carried out in the presence of a lipophilic solvent comprising isoparaffins, such as e.g. selected from solvents that are commercially available as Isopar™ fluids, particular selected from Isopar™ M, Isopar™ N, Isopar™ K, Isopar™ L, Isopar™ H or solvents with equivalent or identical properties but from other suppliers, wherein the color of the desired fermentation product, particularly apocarotenoids such as e.g. retinoids, more particularly retinyl acetate, that accumulates in said solvent is translucent, compared to dark/black (opaque) color such as e.g. obtained in the presence of a second phase solvent such as e.g. Drakeol®.

As known in the art, color can be precisely described in several different co-ordinate systems, such as XYZ, RGB, CYMK, or L*a*b*, including the Pantone® Matching System (PMS). In these systems, different values are assigned to variables like L*, a*, and b* as known in the art. The skilled person knows which instrument to use depending on the different color measurement systems and how to measure the color of the fermentation products present in the second phase solvents as described herein.

As used herein, the term "translucent" can be defined as a transmittance above 10%, where transmittance is the amount of light going through the solvent, i.e. defined as light exiting from solvent/light entering solvent, with 1 cm distance through the solvent. It can also be defined as the ability to read a newspaper through about 5 cm of the solvent.

With regards to the translucent color profile as indicated particularly in Table 9, it refers to light yellowish color of the fermentation product, particularly retinoids, more particularly retinyl acetate, present in the second phase solvent as defined herein. Thus, the translucent color of the retinoids present in second phase solvents such as e.g. Isopar™ M, H, K, L corresponds to a color according to PMS 120-PMS 129 as defined by the Pantone® Matching System (PMS) color scheme. The terms "translucent", "transparent", "light yellow" or "light yellowish" are used interchangeably herein.

As used herein, the term "dark/black" is opaque and can be defined as transmittance less than 10%, according to the definition given above.

With regards to the dark/black color profile as indicated particularly in Table 9, it refers to the dark (opaque) color of the fermentation product, particularly retinoids, more particularly retinyl acetate, present in the second phase solvent as defined herein. Thus, the dark color of the retinoids present in second phase solvents such as e.g. Exxsols D60, D80, D95, D110 or Drakeol 5 corresponds to a color according to PMS 182-PMS 209 as defined by the Pantone® Matching System (PMS) color scheme.

Production of <C40-isoprenoids as described above using the two-phase culture system as defined herein in the presence of a lipophilic solvent as defined herein includes cultivation of a suitable host cell, particularly fungal host cell, such as e.g. an oleaginous yeast, e.g. *Yarrowia* or *Saccharomyces*, said host cell being grown on a suitable carbon source.

Suitable host cells to be used for the present invention might be selected from any host cell capable of <C40-isoprenoid production including apocarotenoid, sesquiterpene, diterpene or ionone production, such as e.g. fungal host cell, more particularly an oleaginous host cell, such as e.g. *Yarrowia, Rhodosporidium, Lipomyces, Saccharomyces* or *Rhodotorula*, preferably *Yarrowia* or *Saccharomyces*, more preferably *Yarrowia lipolytica* or *Saccharomyces cerevisiae*. Depending on the fermentation product, the skilled person knows which host cell to select including the respective culture conditions.

Suitable carbon sources to be used for the present invention might be selected from linear alkanes, free fatty acids, including triglycerides, particularly vegetable oil, such as e.g. selected from the group consisting of oil originated from corn, soy, olive, sunflower, canola, cottonseed, rapeseed, sesame, safflower, grapeseed or mixtures thereof, including the respective free fatty acids, such as e.g. oleic acid, palmitic acid or linoleic acid. Suitable carbon sources might furthermore be selected from ethanol, glycerol or glucose and mixtures of one or more of the above-listed carbon sources.

In one embodiment, the present invention is directed to a process for the production of retinoids, in particular production of retinyl acetate, i.e. a two-phase culture system in the presence of a lipophilic solvent as defined herein, wherein a retinyl acetate producing host cell, preferably oleaginous yeast cell such as e.g. *Yarrowia*, is cultivated under suitable culture conditions, wherein the lipophilic solvent, preferably selected from solvents that are commercially available as Isopar™ fluids, particular selected from Isopar™ M, Isopar™ N, Isopar™ K, Isopar™ L, Isopar™ H or solvents with equivalent or identical properties but from other suppliers, is not consumed or evaporated during the fermentation process, and/or wherein the formation of FAREs as by-product is reduced or abolished, particularly reduced to at least about 50%, such as e.g. at least about 40, 30, 20, 15, 10, 5, 3, 2, 1, or 0.5% based on total retinoids, and/or wherein the color of the retinyl acetate is translucent and not dark in comparison to e.g. the use of Drakeol® as second phase solvent.

Suitable retinoid-producing host cells, particularly retinyl acetate-producing host cells to be used for the present invention might be selected fungal host cells including oleaginous yeast cells, such as e.g. *Rhodosporidium, Lipomyces, Saccharomyces* or *Yarrowia*, preferably *Yarrowia*, more preferably *Yarrowia lipolytica*, particularly expressing genes coding for heterologous enzymes EC class [EC 2.3.1.84] catalyzing the enzymatic conversion of retinol into retinyl acetate and/or comprising one or more genetic modifications in the endogenous lipase activity, such as i.e. reduced or abolished activity of endogenous lipases involved in conversion of retinol into fatty acid retinyl esters (FAREs), one major undesired side-product in fermentative retinoid production. Suitable strains expressing such ATFs are described in e.g. WO2019058001 or WO2020141168.

Preferably, the retinyl acetate-producing host cell to be used in the present invention is expressing a heterologous ATF, particularly fungal ATF, comprising a highly conserved partial amino acid sequence of at least 7 amino acid residues selected from [NDEHCS]-H-x(3)-D-[GA] (motifs are in Prosite syntax, as defined in https://prosite.expasy.org/scanprosite/scanprosite_doc.html), wherein "x" denotes an arbitrary amino acid and with the central histidine being part of the enzyme's binding pocket, preferably wherein the 7 amino acid motif is selected from [NDE]-H-x(3)-D-[GA], more preferably selected from [ND]-H-x(3)-D-[GA], most preferably selected from N—H-x(3)-D-[GA] corresponding to position N218 to G224 in the polypeptide according to SEQ ID NO:13 in WO2019058001. Examples of such enzymes might be particularly selected from *L. mirantina, L. fermentati, S. bayanus*, or *W. anomalus*, such as e.g. LmATF1 according to SEQ ID NO: 13 in WO2019058001, SbATF1, LffATF1, LfATF1, Wa1ATF1 or Wa3ATF1 as disclosed in WO2019058001, more preferably said ATFs comprising one or more amino acid substitution(s) in a sequence with at least about 20%, such as e.g. 25, 30, 35, 40, 45, 50, 55, 60, 65, 70, 75, 80, 85, 90, 92, 95, 97, 98, 99% or up to 100% identity to SEQ ID NO:13 in WO2019058001, wherein the one or more amino acid substitution(s) are located at position(s) corresponding to amino acid residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof and as particularly exemplified in Table 4 of WO2020141168, most preferably comprising one or more amino acid substitution(s) on positions corresponding to amino acid residue(s) 69, 407, 409, 480, 484, and combinations thereof in SEQ ID NO:13 in WO2019058001.

In one particular embodiment, the retinyl acetate-producing host cell to be used for the process according to the present invention comprises an amino acid substitution at a position corresponding to residue 69 in the polypeptide according to SEQ ID NO:13 in WO2019058001 leading to asparagine, serine or alanine at said residue, such as e.g. via substitution of histidine by asparagine (H69N), serine (H69S) or alanine (H69A), with preference for H69A. Said modified enzyme might be originated from yeast, such as e.g. *L. mirantina, L. fermentati, W. anomalus* or *S. bayanus*, preferably from *L. mirantina*, optionally being combined with amino acid substitution at a position corresponding to residue 407 in the polypeptide according to SEQ ID NO:13 in WO2019058001 leading to isoleucine at said residue, such as e.g. via substitution of valine by isoleucine (V4071), optionally being combined with an amino acid substitution at a position corresponding to residue 409 in the polypeptide according to SEQ ID NO:13 in WO2019058001 leading to alanine at said residue, such as e.g. via substitution of glycine by alanine (G409A), optionally being combined with amino acid substitution at a position corresponding to residue 480 in the polypeptide according to SEQ ID NO:13 in WO2019058001 leading to glutamic acid, lysine, methionine, phenylalanine or glutamine at said residue, such as e.g. via substitution of serine by glutamic acid (S480E), lysine (S480L), methionine (S480M), phenylalanine (S480F) or glutamine (S480Q), optionally being combined with amino acid substitution at a position corresponding to residue 484 in the polypeptide according to SEQ ID NO:13 in WO2019058001 leading to leucine at said residue, such as e.g. via substitution of isoleucine by leucine (1484L). Said modified enzyme might be originated from yeast, such as e.g. *L. mirantina, L. fermentati, W. anomalus* or *S. bayanus*, preferably from *L. mirantina*. In a most preferred embodiment, the ATF to be used for the process according to the present invention is a modified ATF comprising amino acid substitutions S480Q_G409A_V4071_H69A_1484L and is obtainable from *Lachancea mirantina*.

As used herein, the term "retinyl-acetate producing host cell" is a host cell capable of synthesizing retinol and expressing ATF as defined herein resulting in retinyl acetate with a percentage of at least about 70-90% based on total retinoids produced by said host cell. Optionally, such retinyl acetate producing host cell is furthermore capable of producing carotenoids.

In one embodiment, the retinyl acetate-producing host cell to be used for the process according to the present invention might comprise further modifications, such as modification in endogenous enzyme activities leading to conversion of retinol into FAREs. Particularly, such modifications include reduction or deletion of endogenous lipase activities, particularly activity of one or more endogenous gene(s) encoding enzymes with activity equivalent to *Yarrowia* LIP2 and/or LIP3 and/or LIP4 and/or LIP8, being reduced or abolished, such as polypeptides with at least about 50%, such as 60, 70, 80, 90, 95, 98, or 100% identity to SEQ ID NO:1, 3, 5, 7, or combinations thereof, wherein SEQ ID NO: 1 corresponds to LIP2 obtainable from *Yarrowia lipolytica*, SEQ ID NO:3 corresponds to LIP3 obtainable from *Yarrowia lipolytica*, SEQ ID NO:5 corresponds to LIP8 obtainable from *Yarrowia lipolytica*, SEQ ID NO:7 corresponds to LIP4 obtainable from *Yarrowia lipolytica*. Preferred is a modification in the activity of a lipase corresponding to activity of *Yarrowia* LIP8, such as particularly reduced or abolished activity, more particularly abolished activity, more preferably wherein a polypeptide with at least about 50% identity to SEQ ID NO:5 is abolished.

The term "lipase" is used interchangeably herein with the term "enzyme having lipase activity". It refers to enzymes involved in pre-digestion of triglyceride oils such as e.g. vegetable oil into glycerol and fatty acids that are normally expressed in oleaginous host cells. Suitable enzymes to be modified in a retinyl acetate-producing host cell as defined herein might be selected from endogenous enzymes belonging to EC class 3.1.1.-, including, but not limited to one or more enzyme(s) with activities corresponding to *Yarrowia* LIP2, LIP3, LIP4, or LIP8 activities.

As used herein, an enzyme having "activity corresponding to the respective LIP activity in *Yarrowia*" includes not only the genes originating from *Yarrowia*, e.g. *Yarrowia lipolytica*, such as e.g. *Yarrowia* LIP2, LIP3, LIP4, LIP8 or combinations thereof, but also includes enzymes having equivalent enzymatic activity but are originated from another source organism, particularly retinyl acetate-producing oleaginous host cell, wherein a modification of such equivalent endogenous genes would lead to an increase in retinol to retinyl acetate conversion as defined herein.

As used herein, an enzyme, particularly a lipase as defined herein, having "reduced or abolished" activity means a decrease in its specific activity, i.e. reduced/abolished ability to catalyze formation of a product from a given substrate into glycerol and fatty acids during fermentation, including reduced or abolished activity of the respective (endogenous) gene encoding such lipases. A reduction by 100% is referred herein as abolishment of enzyme activity, achievable e.g. via deletion, insertions, frameshift mutations, missense mutations or premature stop-codons in the endogenous gene encoding said enzyme or blocking of the expression and/or activity of said endogenous gene(s) with known methods.

As used herein, "deletion" of a gene leading to abolishment of gene activity includes all mutations in the nucleic acid sequence that can result in an allele of diminished function, including, but not limited to deletions, insertions, frameshift mutations, missense mutations, and premature stop codons, wherein deleted means that the corresponding gene/protein activity, such as particularly endogenous lipase activity, cannot be detected (any more) in the host cell.

Genetic modifications as defined herein include, but are not limited to, e.g. gene replacement, gene amplification, gene disruption, transfection, transformation using plasmids, viruses, or other vectors. An example of such a genetic modification may for instance affect the interaction with DNA that is mediated by the N-terminal region of enzymes as defined herein or interaction with other effector molecules. In particular, modifications leading to reduced/abolished specific enzyme activity may be carried out in functional, such as functional for the catalytic activity, parts of the proteins. Furthermore, reduction/abolishment of enzyme specific activity might be achieved by contacting said enzymes with specific inhibitors or other substances that specifically interact with them. In order to identify such inhibitors, the respective enzymes, such as e.g. certain endogenous lipases as defined herein, may be expressed and tested for activity in the presence of compounds suspected to inhibit their activity.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

As used herein, an enzyme is "expressed and active in vivo" if mRNA encoding for the protein can be detected by Northern blotting and/or protein is detected by mass spectrometry. With regards to the exogenous lipase activity as defined herein it means ability to improve triglyceride utilization of a host cell comprising modification of endogenous lipase activities as defined herein. With regards to ATFs as defined herein it means ability of a host cell for acetylation of retinol into retinyl acetate.

The terms "sequence identity", "% identity" are used interchangeable herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity.

The enzymes as described herein to be expressed in a suitable host cell to be used in the present invention also encompass enzymes carrying (further) amino acid substitution(s) which do not alter enzyme activity, i.e. which show the same properties with respect to the enzymes defined herein. Such mutations are also called "silent mutations". Examples of silent mutations included in the present invention are host-optimized sequences.

The host cell including but not limited to the retinyl acetate producing host cells as defined herein is cultivated in an aqueous medium in the presence of suitable carbon sources and the lipophilic solvent as defined herein, optionally supplemented with appropriate nutrients under aerobic or anaerobic conditions and as known by the skilled person to enable production of the desired fermentation products, such as e.g. retinyl acetate. The fermentation may be conducted in batch, fed-batch, semi-continuous or continuous mode. Particularly, retinyl acetate fermentations are run in fed-batch stirred tank reactors. Fermentations can be run for 5 to 14 days, such as e.g. for around 118 h. Fermentation products including retinyl acetate accumulated in the second phase solvent as defined herein may be harvested at a suitable moment, e.g. when the tank fills due to addition of the feed. Depending on the host cell, cultivations can vary, as it is known to the skilled person. The desired fermentation products such as e.g. retinyl acetate, alpha-ionone, beta-ionone or the like might be used as ingredients/formulations in the food, feed, pharma or cosmetic industry. Cultivation and isolation of beta-carotene and retinoid-producing host cells selected from *Yarrowia* or *Saccharomyces* is described in e.g. WO2008042338.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code). Thus, for example, strain *Lachancea mirantina* is a synonym of strain *Zygosaccharomyces* sp. IFO 11066, originated from Japan.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in umol substrate consumed or product formed per min per mg of protein. Typically, umol/min is abbreviated by U (=unit). Therefore, the unit definitions for specific activity of umol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity. Analytical methods to evaluate the capability of lipases as defined herein involved in formation of retinyl fatty esters are known in the art and include measurement via HPLC and the like. With regards to activity of LIP2, LIP3, LIP8, LIP4 as defined herein, the skilled person might measure the formation of retinyl fatty esters from conversion of retinol in comparison to the formation of retinyl acetate from conversion of retinol, both measured with a modified and the respective wild-type host cell. Analytical methods to evaluate the capability of a suitable ATF (wild-type or modified) as defined herein for retinyl acetate production, i.e. acetylation of retinol, or enzymes with lipase activity as defined herein are known in the art, such as e.g. described in Example 4 of WO2014096992. In brief, titers of products such as retinyl acetate, retinol, trans-retinal, cis-retinal, beta-carotene and the like can be measured by HPLC.

Optionally, the host cell, such as e.g. *Yarrowia*, particularly retinyl acetate-producing *Yarrowia*, is expressing further enzymes used for biosynthesis of beta-carotene and/or additionally enzymes used for catalyzing conversion of beta-carotene into retinal and/or retinal into retinol. The skilled person knows which genes to be used/expressed for either biosynthesis of beta-carotene and/or bio-conversion of beta-carotene into retinol. Genes and methods to generate carotenoid-producing host cells are known in the art, see e.g. WO2006102342. Depending on the carotenoid to be produced, different genes might be involved.

In a particular embodiment, the host cell as used in a process defined herein might be originated from *Yarrowia lipolytica* as disclosed in WO2019058001 or WO2019057999, thus further genetically modified, wherein the formation of retinyl acetate from beta-carotene is optimized via heterologous expression of beta-carotene oxidases (BCO), retinol dihydrogenase (RDH) and/or acetyl-transferases (ATF). Particularly, a modified retinyl acetate-producing host cell to be used in a process as defined herein might be expressing a BCO originated from *Drosophila melanogaster* or *Danio rerio*, RDH originated from *Fusarium*, and fungal ATF, such as e.g. ATF originated from *Lachancea* or *Saccharomyces*. To enhance the conversion of beta-carotene into retinal into retinol into retinyl acetate in a process as defined herein, said enzymes might comprise one or more mutations leading to improved acetylation of retinol into retinyl acetate.

A host cell comprising the above-described modifications in endogenous gene activities, such as e.g. lipase-activities and or expression of heterologous genes, such as e.g. ATFs, is also referred to as "modified host cell".

As used herein, a "wild-type host cell" means the respective host cell which is wild-type, i.e. non-modified, with respect to the above-mentioned genetic modifications. Thus, in a wild-type host cell the corresponding endogenous enzymes as defined herein are (still) expressed and active in vivo and/or no heterologous enzymes are expressed.

Conversion according to the present invention is defined as specific enzymatic activity, i.e. catalytic activity of enzymes described herein, including but not limited to the enzymatic activity of lipases, in particular enzymes belonging to the EC class 3.1.1.-involved in conversion of retinol into retinyl fatty esters, beta-carotene oxidases (BCOs), retinol dihydrogenases (RDHs), acetyl transferases (ATFs).

Retinoids as used herein include beta-carotene cleavage products also known as apocarotenoids, including but not limited to retinal, retinolic acid, retinol, retinoic methoxide, retinyl acetate, retinyl esters, 4-keto-retinoids, 3 hydroxy-retinoids or combinations thereof. Biosynthesis of retinoids is described in e.g. WO2008042338.

A host cell capable of production of retinoids in e.g. a fermentation process is known as "retinoid-producing host cell". The genes of the vitamin A pathway and methods to generate retinoid-producing host cells are known in the art. As used herein, a "retinol-producing host cell" is a host cell, wherein the respective polypeptides are expressed and active in vivo, leading to production of retinol, e.g. via enzymatic conversion of retinal into retinol. A "retinyl acetate-producing host cell" is the respective host cell capable of acetylation of retinol into retinyl acetate via expression of the respective acetylating enzymes, e.g. ATFs as described herein.

"Retinal" as used herein is known under IUPAC name (2E,4E,6E,8E)-3,7-Dimethyl-9-(2,6,6-trimethylcyclohexen-1-yl) nona-2,4,6,8-tetraenal. It is herein interchangeably referred to as retinaldehyde or vitamin A aldehyde and includes both cis- and trans-isoforms, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

"Vitamin A" as used herein may be any chemical form of vitamin A found in aqueous solutions, in solids and formulations, and includes retinol, retinyl acetate and retinyl esters. It also includes retinoic acid, such as for instance undissociated, in its free acid form or dissociated as an anion. A preferred form of vitamin A is retinyl acetate, wherein the terms "retinyl acetate", "retinol acetate" and "vitamin A acetate" might be used interchangeably (see https://www.cancer.gov/publications/dictionaries/cancer-drug/def/retinyl-acetate?redirect=true).

The terms "triglycerides" and "triglyceride oils" are used interchangeably herein.

"FAREs" or "retinyl fatty esters" as used interchangeably herein includes long chain retinyl esters. These long chain retinyl esters define hydrocarbon esters that consists of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. Long chain retinyl esters include but are not limited to linoleic acid, oleic acid, or palmitic acid.

The following examples are illustrative only and are not intended to limit the scope of the invention in any way. The contents of all references, patent applications, patents, and published patent applications, cited throughout this application are hereby incorporated by reference, in particular WO2020141168, WO2019058001, WO2008042338, WO2014096992, WO2006102342, WO2019057999, WO2016172282.

The invention is particularly directed to the following embodiments (1) to (12):

(1) Fermentative production of isoprenoids with less than 40 carbons as backbone in a two-phase culture system, comprising in situ extraction of said isoprenoids, wherein a suitable host cell is cultivated in the presence of a carbon source and a lipophilic solvent, wherein the lipophilic solvent is different from the carbon source and with a minimal loss of solvent during the fermentation process.

(2) Embodiment (1), wherein the lipophilic solvent and the carbon source are not identical.

(3) Embodiment (1) or (2), wherein the lipophilic solvent comprises isoparaffins or wherein the lipophilic solvent comprises alkanes, particularly iso-alkane or cycloalkanes (4) Embodiment (1), (2) or (3), wherein the fermentation product is selected from the group consisting of apocarotenoids, sesquiterpenes, preferably retinoids, ionones, more preferably retinyl acetate, alpha-ionone, beta-ionone.

(5) Embodiment (1), (2), (3) or (4), wherein the carbon source is selected from linear alkanes, free fatty acids, ethanol, glucose, including triglycerides, particularly vegetable oil, such as e.g. selected from the group consisting of oil originated from corn, soy, olive, sunflower, canola, cottonseed, rapeseed, sesame, safflower, grapeseed or mixtures thereof, including the respective free fatty acids, such as e.g. oleic acid, palmitic acid or linoleic acid.

(6) Embodiment (1), (2), (3), (4) or (5), wherein 20% or less of the solvent is lost during the fermentation.

(7) Embodiment (6), wherein the consumption of the solvent by the host cell is reduced by at least about 50% or wherein the evaporation of the solvent is reduced by at least about 50%.

(8) Embodiment (1), (2), (3), (4), (5), (6) or (7), wherein the formation of by-products or impurities is reduced by at least about 25%, preferably wherein the impurities are selected from retinal, retinol, fatty acid retinyl esters (FAREs) or dihydro-forms such as e.g. dihydro-retinol or dihydro-retinyl acetate, particularly FAREs, rosafluene, phytoene, ergosterol, dihydro-beta-ionone, and other reduced forms.

(9) Embodiment (1), (2), (3), (4), (5), (6), (7) or (8), wherein the host cell is selected from fungal host cells, particularly oleaginous host cells, such as e.g. yeast, preferably selected from *Yarrowia, Rhodosporidium, Lipomyces, Saccharomyces* or *Rhodotorula.*

(10) A process for production of transparent or light yellow <C40 isoprenoids, particularly apocarotenoids, ionones, wherein a suitable host cell, particularly oleaginous yeast, is grown on a suitable carbon source, particularly selected from triglycerides, linear alkanes, free fatty acids, glucose or mixtures thereof, in a two-phase culture system in the presence of a lipophilic solvent comprising isoparaffins, wherein the fermentation product is collected in said solvent and optionally further isolated and/or purified.

(11) Embodiment (10), wherein the fermentation product is retinyl acetate.

(12) Bio-based retinoid form comprising retinol, retinyl acetate with a percentage of retinyl acetate in the range of about 70-90% based on total retinoids, said product being produced by a process according to embodiment (10).

EXAMPLES

Example 1: General Methods and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

Shake plate assay. Typically, 200 μl of 0.25% yeast extract, 0.5% peptone (0.25X YP) is inoculated with 10 μl of freshly grown *Yarrowia* and overlaid with 200 μl of solvent. *Candida rugosa* Lipase (Creative enzymes) was resuspended in PBS and added to the growth media when the carbon source was 2% corn oil. Alternatively, 2% oleic acid was used as a carbon source. The second phase was Drakeol 5, or others listed in table 6 (Example 2). Transformants were purified by steaking to single colonies, grown in 24 well plates (Multitron, 30° C., 800 RPM) in media described above for 4 days at 30° C. The second phase (Drakeol 5, or others listed in table 6) fraction was removed from the shake plate wells and analyzed by UPLC on a normal phase column and/or C4 HPLC, with a photo-diode array detector (see details below).

DNA transformation. Strains were transformed by overnight growth on YPD plate media; 50 μl of cells were scraped from a plate and transformed by incubation in 500 μl with 1 μg transforming DNA, typically linear DNA for integrative transformation, 40% PEG 3550MW, 100 mM lithium acetate, 50 mM Dithiothreitol, 5 mM Tris-Cl pH 8.0, 0.5 mM EDTA for 30 minutes at 40° C. and plated directly to selective media or in the case of dominant antibiotic marker selection the cells were out grown on YPD liquid media for 4 hours at 30° C. before plating on the selective media. URA3 marker recycling was performed using 5-fluororotic acid (FOA). Episomal hygromycin resistance marker (Hyg) plasmids were cured by passage on non-selective media, with identification of Hyg-sensitive colonies by replica plating colonies from non-selective media to hygromycin containing media (100 μg/mL). Selection of the nourseothricin-resistance marker (Nat) was performed on YPD media containing nourseothricin (100 μg/mL).

DNA molecular biology. Plasmid MB9523 containing expression systems for DrBCO, LmATF-S480Q_G409A_V4071_H69A_1484L, and FfRDH (SEQ ID NO:10) was synthesized at Genscript (Piscataway, NJ, USA). Plasmid MB9523 contains the 'URA3' for marker selection in *Yarrowia lipolytica* transformations. For clean gene insertion by random nonhomologous end joining of the gene and marker SfiI plasmid fragment (of MB9523) of interest was purified by gel electrophoresis and Qiagen gel purification column. Clones were verified by sequencing. Typically, genes are synthesized at GenScript (Piscataway, NJ). Plasmids MB9287 (SEQ ID NO:11) and MB9953 (SEQ ID NO:12), containing a Cas9, and guide RNA expression systems to target LIP2, LIP3, and LIP8 in the case of MB9287, and LIP4 in the case of MB9953, were synthesized at Genscript (Piscataway, NJ, USA).

Plasmid list. Plasmid, strains, nucleotide and amino acid sequences that were used are listed in Table 1, 2, 3, 11. In general, all non-modified sequences referred to herein are the same as the accession sequence in the database for reference strain CLIB122 (Dujon B, et al, Nature. 2004 Jul. 1;430 (6995): 35-44).

TABLE 1 list of plasmids used for construction of the strains for overexpression or deletion of the respective genes indicated as "insert". "LmATF1-mut" refers to Lachancea mirantina (LmATF1; SEQ ID NO: 13 in WO2019058001) carrying aa substitutions S480Q_G409A_V407I_H69A_1484L. "DrBCO" refers to BCO originated from Danio rerio (see SEQ ID NO: 18 in WO2020141168); "FfRDH" refers to RDH originated from Fusarium (see SEQ ID NO: 22 in WO2020141168). For more explanation, see text.

| Plasmid | Insert | Marker | SEQ ID NO: |
|---|---|---|---|
| MB7452 | Cas9 | Nat | 9 |
| MB9523 | DrBCO; LmATF1-mut; FfRDH | URA3 | 10 |
| MB9287 | Cas9; LIP2, LIP3 and LIP8 targeting guide RNAs | Hyg | 11 |
| MB9953 | Cas9; LIP4 targeting guide RNAs | Hyg | 12 |

TABLE 2 list of Yarrowia lipolytica strains used. Construction of ML17544 is described in Table 2 of WO2020141168. For more details, see text.

| Strain | Description |
|---|---|
| ML18812 | ML17544 transformed with MB9523 |
| ML18743 | ML18812 with MB9287 lip8, lip2, lip3 deletion |
| ML18743-lip4 | ML18743 with MB9953 lip8, lip2, lip3, lip4 deletion |
| ML13149 | Abienol producing strain from WO2016172282 |
| ML15449 | Beta-ionone producing strain from WO2016172282 |
| ML13716 | Alpha-farnesene producing strain |

TABLE 3

DNA sequences targeted using Cas9 CRISPR for mutation of lipase genes. "Lip gene" means the respective lipase gene from Yarrowia lipolytica. "CRISPR targeting sequence" is the seed sequence used for Cas9 CRISPR targeting. The respective guide RNA expression plasmid for LIP8, LIP2 and LIP3 constructs is MB9287, for LIP4 it is MB9953. For more details, see text.

| Lip gene | CRISPR targeting sequence | SEQ ID NO: |
|---|---|---|
| LIP8 | ACAGCAGGCTGAACGAGGAT | 13 |
| LIP2 | TGGAGGCATGATCAACAGCG | 14 |
| LIP3 | TCACTCCTCAGCCTCCCAAG | 15 |
| LIP4 | GGTGGCCTGGATTCGAGTGG | 16 |
| LIP4 | TTACACCCACTCTATCGGAG | 17 |

Retinoid quantification. Analysis of retinoids were carried out with a C4 reverse phase retinoid method (see below) and C18 as described elsewhere (WO2020141168). The addition of all added intermediates gives the total amount of retinoids.

C4 reverse phase chromatography. For exact determination of discrete retinoids the long run reverse phase system was used. We separated analytes at 230 nm and 325 nm through the Agilent 1290 instrument with YMC Pro C4, 150×3.0 mm 3 μm column (YMC America, Allentown PA) stationary phase, and a 5 μl injection loop volume and column and sample tray controlled at 23° C. with gradients described in Table 4B. Analytes were detected at 230 nm and 325 nm and the peaks identity verified with LCMS. The analytes separated as discrete peaks that were assigned according to Table 4A.

TABLE 4A list of analytes using C4-reverse phase method. The addition of all added intermediates gives the total amount retinoids. "RT" means retention time. For more details, see text.

| Intermediates | RT [min] | λ max [nm] |
|---|---|---|
| trans-retinol | 20.21 | 325 |
| cis-retinol | 20.32 | 325 |
| dihydro-retinol | 20.75 | 290 |
| trans-retinal | 20.89 | 380 |
| cis-retinal | 21.02 | 380 |
| trans-retinyl-acetate | 22.15 | 325 |
| cis-retinyl-acetate | 22.35 | 325 |
| dihydro-retinyl acetate | 22.60 | 290 |
| retinyl esters | 26-30 | 325 |

TABLE 4B

UPLC Method Gradient with solvent A: acetonitrile; solvent B: water; solvent C: water/acetonitrile/methanesulfonic acid 1000:25:1. For more details, see text.

| Time [min] | % A | % B | % C | Flow [ml/min] |
|---|---|---|---|---|
| 0 | 5 | 85 | 10 | 0.5 |
| 20 | 98 | 0 | 2 | 0.5 |
| 35 | 98 | 0 | 2 | 0.5 |
| 35.1 | 5 | 85 | 10 | 0.5 |
| 40 | 5 | 85 | 10 | 0.5 |

Method Calibration. Method is calibrated using high purity retinyl acetate received from DSM Nutritional Products, Kaiseraugst, CH. Retinols and retinal are quantitated against retinyl acetate. Dilutions described in Table 4C are prepared as follows. 40 mg of retinyl acetate is weighed into a 100 ml volumetric flask, and dissolved in ethanol, yielding a 400 μg/mL solution. This solution is sonicated as required to ensure dissolution. 5 ml of this 400 μg/ml solution is diluted into 50 ml (1/10 dilution, final concentration 40 μg/mL), 5 ml into 100 ml (1/20 dilution, final concentration 20 μg/mL), 5 ml of 40 μg/mL into 50 mL (1/10 dilution, final concentration 4 μg/mL), 5 ml of 20 μg/mL into 50 mL (1/10 dilution, 2 μg/mL), using 50/50 methanol/methyl tert-butyl ether (MTBE) as the diluent. All dilutions are done in volumetric flasks. Purity of retinyl acetate is determined by further diluting the 400 μg/mL stock solution 100-fold (using a 2 mL volumetric pipet and a 200 mL volumetric flask) in ethanol. Absorbance of this solution at 325 nm using ethanol is taken as the blank, with adjustment of the initial concentration using the equation (Abs*dilution (100) *molecular weight (328.5)/51180=concentration in mg/mL). Because of quick out-maximization of UV absorbance of retinyl acetate, lower concentrations are better.

TABLE 4C preparation of calibration standards. For more explanation, see text.

| Stock [RA], dilution | Final concentration |
|---|---|
| 20 μg/mL, 1/10 | 2 μg/mL |
| 40 μg/mL, 1/10 | 4 μg/mL |
| 400 μg/mL, 1/20 | 20 μg/mL |
| 400 μg/ml, 1/10 | 40 μg/mL |

Sample preparation. Top second phase layer samples from each strain were diluted at a 25-fold dilution or higher into tetrahydrofuran (THF). Fermentation whole broth was prepared using a 2 mL Precellys (Bertin Corp, Rockville, MD) tube, add 25 μl of well mixed broth and 975 μl of THF. Precellys 3×15×7500 rpm for two cycles with a freeze at −80° C. for 10 minutes between cycles. Cell debris was spun down via centrifugation for 1 minute at 13000 rpm. These samples were diluted 10-fold in THF.

Color measurement. Colors here are defined by the Pantone color scheme for light yellow/translucent (PMS 120-

129) and black/dark (PMS 182-209) described elsewhere at http://www.bcslabel.com/pdf/pms_color_chart.pdf).

Fermentation conditions. Fed-batch fermentations were identical to the previously described conditions except using Drakeol 5 (Penreco, Karns City, PA, USA) or another 2nd phase overlay (listed in Table 5) and stirred tank that was corn oil, glucose or ethanol fed in a bench top reactor with 0.5L to 5L total volume (see WO2016172282). The batch medium carbon source composition and feed medium are listed in Table 5. Feeding was initiated after the initial batch carbon had been consumed, with feed added in a controlled manner to maintain a dissolved oxygen level (DO) setpoint.

Briefly, the fermentations were run in 3.0L flood volume in glass New Brunswick or Eppendorf fermentation systems. The fermentor was batched with an autoclaved 1.6 kg aqueous solution consisting of $MgSO_4 \cdot 7H_2O$ (1.96 g/kg), NaCl (0.20 g/kg), $CaCl_2) \cdot 2H_2O$ (0.33 g/kg), $(NH_4)$ $2SO_4$ (8.18 g/kg), $KH_2PO_4$ (8.47 g/kg), Tastone yeast extract (6.13 g/kg, Marcor, Leominster, MA), DF204 antifoam (8.13 g/kg), thiamine-HCl (0.2 g/kg of a 4 mg/g solution), trace elements stock solution (3.27 g/kg of solution consisting of: citric acid (200 g/kg), $FeSO_4 \cdot 7H_2O$ (27.3 g/kg), $Na_2MoO_4 \cdot 2H_2O$ (19.6 g/kg), $CuSO_4 \cdot 5H_2O$ (18.7 g/kg), $H_3BO_3$ (4.9 g/kg), $MnSO_4 \cdot H_2O$ (21.9 g/kg), $ZnSO_4 \cdot 7H_2O$ (30.2 g/kg)).

After cooling a carbon source was added along with 400 ml Drakeol 5 or other second phase. The fermentation was inoculated with 200 ml overnight shake flask cultures of YP media grown with 250 RPM agitation at 30° C. and the specific carbon sources shown in Table 3. Fermentation parameters were agitation at 1000 RPM, airflow at 2.3LPM for ethanol and 2.3 LPM for oil and mixed fatty acids, pH controlled at 5.5 control with $NH_4OH$, and the temperature set to 30° C. At feed start, the DO setpoint was set at 40%. The DO setpoint was ramped down to 20% in a linear fashion over the following 24 hours. The DO was then maintained at 20% via feed addition for the remainder of the fermentation.

TABLE 5 fermentation feeding protocol. Fermentation $2^{nd}$ phase was always 400 ml in volume. For more explanation, see text.

| Run: | Batch: | Feed: |
|---|---|---|
| Ethanol | 5% glucose (w/v)<br>1% ethanol (w/v) | 100% ethanol (w/v) |

Example 2: Evaluations of Solvents to be Used as Second Phases for Collections of Retinoids Produced in *Yarrowia lipolytica*

To identify optimal second phases for collection of retinoids produced in strain ML18743, various solvents were tested as second phases and as listed in Table 6. Shake plate assays were performed as described in Example 1. These second phases all had a lower density than the growth medium, which together with their hydrophobicity, enabled convenient supernatant sampling from a centrifuged culture sample.

TABLE 6 list of solvents tested as $2^{nd}$ phases with Yarrowia strains ML18743 and 18812 in shake plate assay. "Abbrev." Means abbreviation. For more details, see text.

| Solvent | Manufacturer | description | Abbrev. |
|---|---|---|---|
| n-dodecane | Sigma | $CH_3(CH_2)_{10}CH_3$ | dode |
| Iso-dodecane mix | Acros Organics | Isododecane mixed isomers | dode mix |
| Drakeol 5 | Penreco | Branched mineral oil | Drake 5 |
| Isopar ™ H | Exxon Mobile | Synthetic isoparaffin fluids | Iso H |
| Isopar ™ K | Exxon Mobile | Synthetic isoparaffin fluids | Iso K |
| Isopar ™ L | Exxon Mobile | Synthetic isoparaffin fluids | Iso L |
| Isopar ™ M | Exxon Mobile | Synthetic isoparaffin fluids | Iso M |
| Exxsol ™ D60 | Exxon Mobile | Paraffins/isoparaffins/cycloparaffins | E D60 |
| Exxsol ™ D80 | Exxon Mobile | Paraffins/isoparaffins/cycloparaffins | E D80 |
| Exxsol ™ D95 | Exxon Mobile | Paraffins/isoparaffins/cycloparaffins | E D95 |
| Exxsol ™ D110 | Exxon Mobile | Alkanes/isoalkanes/cyclic | E D110 |

The performance of said $2^{nd}$ phases were tested with regards to growth, loss (consumption, evaporation or other ways of disappearance) of the solvents during the fermentation and the density and viscosity of the cultivation medium, wherein the test was carried out after 4 days of growth period. The results are shown in Table 7.

TABLE 7

Growth, evaporation and density in dependence of the solvent used as $2^{nd}$ phase. Viscosity was measured at 20° C.. For more details, see text.

| Solvent | growth | Loss | Density [g/ml] | Viscosity |
|---|---|---|---|---|
| none | ++ | N/A | N/A | N/A |
| dode | ++ | 100% | 0.75 | 1.34 |
| dode mix | ++ | 20% | 0.75 | 1.3 |
| Drake 5 | ++ | <5% | 0.84 | 6.9 |
| Iso H | ++ | 20% | 0.76 | 1.9 |
| Iso K | ++ | 20% | 0.76 | 1.86 |
| Iso L | ++ | <5% | 0.77 | 2.11 |
| Iso M | ++ | <5% | 0.79 | 4.23 |
| E D60 | ++ | 20% | 0.8 | 1.77 |
| E D80 | ++ | 20% | 0.8 | 2.28 |
| E D95 | ++ | 20% | 0.81 | 2.81 |
| E D110 | ++ | <5% | 0.81 | 4.1 |

None of the second phases listed caused growth inhibition, as compared to cells grown without a second phase, while aromatic second phases such as Exxon Solvesso 150™ and Exxon Solvesso 200™ (not shown) are not favorable to growth. Interestingly, 2nd phase comprising Isopar™ M, Exxsol™ D110 or Drakeol 5 were more or less still present at the end of the fermentation, i.e. did neither evaporate nor were consumed by the host cell. Other second phases, including Exxsol™ D60, Exxsol™ D80, Exxsol™ D95, Isopar™ L, Isopar™ K, Isopar™ H, and dodecane (mixture of isomers) lost approximately 20% of the initial volume during the test period. One second phase, n-dodecane, completely disappeared over the test period, most likely attributable to consumption.

Example 3: Impact of Solvents to be Used as Second Phases on Lipases in *Yarrowia lipolytica* Producing Retinyl Acetate To test the impact of second phases on lipases, we measured the inhibition of heterologous *Candida rugosa* lipase CrLIP (Creative Enzymes, US) by comparing retinoid output from strains grown with each of these second phases (see Table 8). Strain ML18743 and ML18743-lip4 are unable to consume triglyerides without the addition of a lipase, such as CrLIP. To determine the effect of CrLIP inhibition, total retinoid production of the cells grown in oleic was compared to cells grown in corn oil in the presence of CrLIP in a lipase-deletion strain (see Example 1). With the exception of Drakeol 5 and Exxsol™ D60, all the second phases inhibited lipase by at least 20%, with maximum inhibition by Isopar™ L of 40%. In addition, the impact of second phases on fatty acid retinyl esters (FAREs) was measured. Briefly, the percentage of FAREs (% FARE) based on total retinoids was calculated for each of the second phases, and the % FARE was then compared to % FARE with Drakeol 5 as second phase. As shown in Table 8, percentage of FARE could be reduced by using selected 2nd phase solvents as compared to the use of Drakeol 5 as second phase.

TABLE 8

Impact of second phases on lipase inhibition and FARE production. "% FARE" was calculated as a percent of total retinoids for cells grown with the indicated second phase in corn oil together with heterologous CrLIP, and then compared to the % FARE present in cultures with corn oil together with heterologous CrLip and Drakeol 5 as second phase. For more details, see text.

| Solvent | CrLIP inhibition | % FARE compared to % FARE with Drakeol 5 [%] |
|---|---|---|
| Drake 5 | 0% | 100 |
| Iso L | 40% | 73 |
| Iso M | 29% | 56.8 |
| E D60 | 4% | 58.6 |
| E D80 | 21% | 98.5 |
| E D95 | 35% | 28.2 |
| E D110 | 37% | 49.9 |

Example 4: Impact of Solvents to be Used as Second Phases on Color in *Yarrowia lipolytica* Producing Retinyl Acetate In accordance to Example 2, experiments were performed using different solvents as second phases with subsequent color measurement of the fermentation product, i.e. retinyl acetate accumulated in the 2$^{nd}$ phase.

Whereas the color of the fermentation product was dark in the case of Drakeol 5 and the Exxsols (Exxsol™ D60, D80, D95 or D110), a light yellow translucent color was obtained with the Isopars and with the Iso-dodecane mix (Acros Organics). The results are shown in Table 9.

TABLE 9

Color profile in dependence of the solvent used as 2$^{nd}$ phase. Color was measured according to the method described in Example 1. For more details, see text.

| Solvent | Visible color |
|---|---|
| dode | N/A |
| dode mix | Light yellow |
| Drake 5 | Dark/black |
| Iso H | translucent |
| Iso K | translucent |
| Iso L | translucent |
| Iso M | translucent |
| E D60 | Dark/black |
| E D80 | Dark/black |
| E D95 | Dark/black |
| E D110 | Dark/black |

Example 5: Impact of Solvents to be Used as Second Phases on Total Retinoid Production and Purity in *Yarrowia lipolytica*

Fermentation experiments were performed as described in Example 1, using different solvents as second phases with subsequent measurement of retinoids accumulated in the 2$^{nd}$ phase.

As indicated in Table 10, use of Isopar™ K and Isopar™ M as a second phase demonstrated an improvement in total retinoid output when compared to the use of Exxol D110 as a second phase. In addition, use of Isopar™ K and Isopar™ M each improved % retinyl acetate based on total retinoids. Similar results are obtained with other Isopars, i.e. Isopar™ L and H.

TABLE 10

Total retinoids compared to Exxsol ™ D110 and % retinyl acetate based on total retinoids ("purity %") for isopars as second phase solvent. For more details, see text.

| Second Phase | Total Retinoids (% of E D110) | purity % |
|---|---|---|
| E D110 | 100.00 | 70 |
| I K | 150.22 | 90 |
| I M | 156.30 | 90 |

TABLE 11 sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| 1 | MKLSTILFTA CATLAAALPS PITPSEAAVL QKRVYTSTET SHIDQESYNF<br>FEKYARLANI GYCVGPGTKI FKPENCGLQC AHFPNVELIE EFHDPRLIFD |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | VSGYLAVDHA SKQIYLVIRG THSLEDVITD IRIMQAPLTN FDLAANISST |
| | ATCDDCLVHN GFIQSYNNTY NQIGPKLDSV IEQYPDYQIA VTGHSLGGAA |
| | ALLFGINLKV NGHDPLVVTL GQPIVGNAGF ANWVDKLFFG QENPDVSKVS |
| | KDRKLYRITH RGDIVPQVPF WDGYQHCSGE VFIDWPLIHP PLSNVVMCQG |
| | QSNKQCSAGN TLLQQVNVIG NHLQYFVTEG VCGI |
| 2 | atgaagcttt ccaccatcct cttcacagcc tgcgctaccc tggctgccgc |
| | cctcccttcc cccatcactc cttctgaggc cgcagttctc cagaagcgag |
| | tgtacacctc taccgagacc tctcacattg accaggagtc ctacaacttc |
| | tttgagaagt acgcccgact cgcaaacatt ggatattgtg ttggtcccgg |
| | cactaagatc ttcaagccct tcaactgtgg cctgcaatgt gcccacttcc |
| | ccaacgttga gctcatcgag gagttccacg acccccgtct catctttgat |
| | gtttctggtt acctcgctgt tgatcatgcc tccaagcaga tctaccttgt |
| | tattcgagga acccactctc tggaggacgt cataaccgac atccgaatca |
| | tgcaggctcc tctgacgaac tttgatcttg ctgctaacat ctcttctact |
| | gctacttgtg atgactgtct tgtccacaat ggcttcatcc agtcctacaa |
| | caacacctac aatcagatcg gccccaagct cgactctgtg attgagcagt |
| | atcccgacta ccagattgct gtcaccggtc actctctcgg aggagctgca |
| | gcccttctgt toggaatcaa cctcaaggtt aacggccacg atcccctcgt |
| | tgttactctt ggtcagccca ttgtcggtaa cgctggcttt gctaactggg |
| | tcgataaact cttctttggc caggagaacc ccgatgtctc caaggtgtcc |
| | aaagaccgaa agctctaccg aatcacccac cgaggagata tcgtccctca |
| | agtgcccttc tgggacggtt accagcactg ctctggtgag gtctttattg |
| | actggcccct gatccaccct cctctctcca acgttgtcat gtgccagggc |
| | cagagcaata aacagtgctc tgccggtaac actctgctcc agcaggtcaa |
| | tgtgattgga aaccatctgc agtacttcgt caccgagggt gtctgtggta |
| | tctaa |
| 3 | MPLELPSLNA SIVGNTVQNG AVEQFLNIRY ADIPGKFEKP VLKNDWNGAE |
| | IDATKVGPVC PQPRTPENFF SVPDDLWEKV NVDTYQDGLL CDNLIVTRPK |
| | GVSANARLPT VVWIHGGSNI EGSIYNLIYE PQFLVAESVR VGKPIVHVCI |
| | EYRLGLAGFL TKNGKGNWGT WDQYTGCQWV NRHIQDEGGD PLNVTLTGES |
| | AGSVAVHNML IKDSMNGRKL FRNAVMMSGT LETITPQPPK WHARLEEKVA |
| | KVTGKEVADL ASLSDKELLD AQIKLNVAVC MTCDDGDEFE PGWKQHLTPD |
| | WLDKLIISDC LKTDATENYF NHLLEKKMEE RLFQSHFLRL AYGLEPWDHR |
| | GGDIKSACLD VDVLYMENST KENEHGDKLS ARNNGSTSRV YRLAVDEPNP |
| | HNPDQRAHHA VDVLYMFNST KFNEHGDKLS RLFQSHELRL AYGLEPWDHR |
| | NFGVYRNGGY QQLPLSELNK VRPVERYEAL SKMDFGQVGR LSNALSRL |
| 4 | atgcctctcg aactcccctc gctcaacgcc tcgattgtcg gcaacaccgt |
| | tcagaacggc gctgttgagc agtttctcaa catccgatac gccgacattc |
| | ctggcaagtt tgagaagccc gtgctcaaga acgattggaa cggcgcggag |
| | atcgacgcca ccaaggtcgg tcccgtgtgc cccaacccc gcaccccatt |
| | caacttcttc tccgtgccag acgacctctg ggagaaagtc aatgtggaca |
| | cgtaccagga cggtctgctg tgcgacaacc tgattgtgac gcgaccgaag |
| | ggcgtgtctg ccaacgcccg gctgcccact gttgtgtgga tccacggcgg |
| | ctccaatatt gagggcagta tctacaacct catctatgag ccccagttcc |
| | tggtggcaga gtcggtgcga gtaggcaagc cgattgtgca cgtgtgtatc |
| | gagtaccgac tgggtctcgc gggcttcctc accaagaacg gcaagggcaa |
| | ctggggcacg tgggatcagt acacgggctg ccagtgggtc aaccgccaca |
| | ttcaggactt tggaggcgat cctttgaacg tgacattgac cggtgagtct |
| | gccggctctg tagcagtcca taacatgctc atcaaggact ccatgaacgg |
| | ccgaaagttg ttccgaaatg ccgtcatgat gagtggcact ctcgagacca |
| | tcactcctca gcctcccaag tggcatgctc gtttggagga gaaggtggcc |
| | aaggtcactg gcaaggaagt ggccgacctt gcttctctgt ccgataagga |
| | gctgctcgac gcccagatca agctcaatgt ggctgtgtgc atgacttgcg |
| | acgacggcga ctttttcgag cccggatgga agcagcatct gactcctgac |
| | tggctcgaca agctcatcat ctccgattgc aaggacgagg gcatgctgta |
| | tttcctgcca gtcaacgcgc aggacgacga ggagctgttg gcaaaggtgg |
| | ccaagtcgcc cgtgggtaag gagatttccg agctttacgg catcaaggag |
| | ggtggcgata tcaagtctgc gtgtctcgat ctcaagactg acgccacctt |
| | caattacttt aaccatctgc tgttcaagaa gatggaggag gcccgaaaca |
| | acggctccac ttctcgagtt taccgtctgg ccgtcgatga gcccaacccc |
| | cacaaccccg accagcgggc ccaccacgcc gtcgacgtgc tgtacatgtt |
| | caactcgacc aagttcaacg agcacggcga caagctgtct cggctgttcc |
| | agagccactt tttgcggctg gcgtatggcc tggagccctg ggaccatcga |
| | aactttggag tgtacagaaa cggcggctac cagcagctgc cgctgagtga |
| | gttgaacaag gtccgacccg tcgagcggta cgaggcgctg tccaagatgg |
| | actttggcca ggttgggcgt ttgtccaatg cgctttcgcg cctatga |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| 5 | MVSLSARIKD FFSVLLLGAA TITPSTQTAG VSQGFYDFAR DEAHLSNIAY<br>CVNAPITPLN PDFTCGNSCK HFPEIELVKT FGGNFFKTSI TGYLAVDHVK<br>KEKYVVERGT FSLADAITDM QFQLSPELVD VPALNTFSAN DTTAEAQTHC<br>EGCKIHDGES KAFTETWGNI GEDLQKHLDA NPDYQLYVTG HSLGAAMALL<br>GATSIKLKGY DPILINYGQP RVGNKPFAEF INKLWEGEGN GLEITPERKL<br>YRMTHWNDIF VGLPNWEGYT HSNGEVYINN RFINPPLKDV ISCAGGENSK<br>CYRSSESLLS QINLLONHLA YIDYIGYCAL NIGRRELADQ EHYTGPYYYG<br>HRSEEDFKKL GLELSTPQVE N |
| 6 | atggtatccc tctctgctcg aatcaaagac ttttttcgg tcctcctcct<br>cggagctgca accatcactc cctccacaca gaccgcaggc gtgtctcaag<br>ggttctatga ttttgctcgg gactttgccc atctgtccaa cattgcctac<br>tgtgtcaatg ctcccatcac tccactgaac ccggacttca cctgtggcaa<br>ctcgtgcaag cactttccgg aaattgagct tgtgaagaca tttggaggca<br>acttcttcaa gacctccatt acgggctacc tggctgtcga tcatgtcaag<br>aaggagaagt acgttgtctt ccgaggaacc ttttcgctgg cagacgcgat<br>cacggacatg cagttccagc tgtctccttt cctggtcgat gtgcctgccc<br>tgaacacttt ctcagctaat gacaccaccg cagaggccca gacgcactgt<br>gagggctgca aaattcacga cggcttctcc aaggccttta ccgagacctg<br>gggtaacatt ggtgaggatc tgcagaaaca cctggacgct aacccggact<br>accagctgta cgtgactggc cattctctgg gagctgctat ggcccttctt<br>ggagctactt ccatcaagct caagggctac gatcccattc tcatcaacta<br>cggacagccc cgagtcggaa acaagccctt cgctgagttc attaacaagt<br>tgtggtttgg agaaggcaac ggtctggaaa tcacccccga gagaaagctg<br>taccgaatga cccactggaa cgacatcttt gttggcctgc ccaactggga<br>gggatacacc cactctaacg gtgaagtata catcaacaac cggttcatca<br>accctcctct caaggatgtc atctcttgtg ctggaggcga aaactcgaag<br>tgctaccgat cctcgttcag cctgctgtcc cagatcaatc tgctccaaaa<br>ccacctggct tacattgatt acattggata ctgcgctctg aacattggtc<br>gacgagagct tgccgatcag gaacattaca ctggtcctta ttactatggt<br>catcgatctg aggaggactt taagaagttg ggcttggagc tatccacccc<br>acaagttgag aactga |
| 7 | MAGENFTFGQ VISYLASMLY GOVDATSSST RIQATQDLYD FTAKFSRLSN<br>IAYCINAPFT PLRTDFTCGE SCRYFPDLQL DSVEGGNESS ASTTGYIAYD<br>HKKKEKYIVF RGTFSIPDII TDIQFQTAPW LTSLPTHLIP TKEDFEHKQA<br>ILKHYAAENK GLSNLEERQD VVHEDPSLVP KKMDKCENCQ IHDGFAKGEN<br>ETIEHAGPQI EKFLGNNTDY KMFVVGHSLG AAQAQLFATQ FKLLGEDPYM<br>INFGQPRLGN PEFAAYINQL WENDTGLVVN DARRFYRVTH WNDIVVGVPD<br>WLNYTHSIGE VFIDEESVYP KLDKVVVCEG GENPLCHRGT ENLWSRINFL<br>QNHLAYIFYI GLCAFNIGRR DVLNMPQYQG NFSYQHNIDP NYNYDTKVPT<br>RISKSN |
| 8 | atggcagggt tcaacttcac tttcgggcag gtgatttcgt acctggcttc<br>catgctctat ggacaggtgg atgccacttc atcctccact cgaatccagg<br>ccacccagga tctgtacgac ttcacagcca agttttcgcg actctcaaac<br>atcgcgtact gcatcaatgc cccctteacg cctctcagaa cggacttcac<br>ctgcggagaa agctgtcggt acttccccga cctccagctg gactcagtgt<br>ttggtggtaa cttctcctca gcctccacta ccggctacat tgcatacgac<br>cacaagaaga aggaaaagta cattgtgttt cgaggaactt tcagtatccc<br>tgatatcatc acagacattc aatttcagac tgccccttgg ttgacctctc<br>tgcccacgca tctgatccct accaaggagg actttgaaca caagcaggcc<br>atcctgaagc actacgctgc cgaaaacaag ggtctcagca acctggaaga<br>gcgacaggat gttgtgcatg aagaccctag cctggttccc aagaaaatgg<br>acaagtgcga gaactgccag atccatgacg gattcgccaa gggcttcaac<br>gagactatcg agcatgccgg accccagatt gaaaagttcc tgggcaataa<br>caccgactac aagatgtttg ttgttggcca ctctctagga gctgctcagg<br>cccagctgtt tgctacacag ttcaaactgc tgggatttga cccttacatg<br>atcaactttg gacagcctcg acttggaaac cctgagttcg ccgcctacat<br>caaccagctg tggttcaacg atactggtct ggttgtcaat gatgcccgac<br>gattctaccg agtgactcac tggaacgata tcgtcgtggg agtgcccgac<br>tggctcaatt acacccactc tatcggagag gtgttcatag acgaggagag<br>cgtttacccc aagctggaca aggtggtggt gtgcgaggga ggagagaacc<br>ccctgtgcca ccgaggaact ttcaacctgt ggtcacgaat caacttcctg<br>cagaaccatt tggcttatat cttctacatt ggtctgtgtg ctttcaacat<br>tggccgaaga gacgtgctca acatgccaca ataccagggc aacttctcgt<br>accagcacaa catcgacccc aactacaatt acgataccaa ggttcccacc<br>cggatcagta aatcaaacta a |
| 9 | cgcgtggatc gccggtgcgt tgacgttggt gacctccagc cagaggtgcc<br>cggcgccccg ctcgccggcg aactccgtcg cgagccccat caacgcgcgc |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | ccgaccccgt gcccccggtg ctccggggcg acctcgatgt cctcgacggt<br>cagccggcgg ttccacgccg agtacgagat gaccacgaag cccgccaggt<br>cgccgtcgtc cccgtacgcg acgaacgtcc gggagtccgg gtcgccgtcc<br>tccccgtcgt ccgattcgtc gtccgattcg tcgtcgggga acaccttggt<br>caggggcggg tccaccggca cctcccgcag ggtgaagccg tccccggtgg<br>cggtgacgcg gaagacggtg tcggtggtga aggacccatc cagtgcctcg<br>atggcctcgg cgtcccccgg gacactggtg cggtaccggt aagccgtgtc<br>gtcaagagtg gtcattttg tgtctaggtg tttgtgtttg gactgcgatc<br>agtgaagaaa agaagaggaa aaattgtgca agaaattttg ctttcaagac<br>ttggctgatg cagcagggta actctgggac acagacctat gtttgtggtt<br>aaactcaatg cacgtggtac gtgcgtggag cgcttaccca tccaagggtg<br>tggacatgga accgacggtc cgtggagttg tgtaatgtca ttttggcgac<br>tcttgaagca aggctataaa aaaattgtgt ggcttgagtc ttatcgagct<br>cggtcactac aagagttaat cttcctgtct caggcagaca ggtcaggcag<br>ggttactttt gggtgtgctg taactcactg tatggccgtt agtgcgcata<br>gacgttgtac atactggacc gaattgtagc gtgctcaata gggccaataa<br>agctattgta gggatccgaa ttttcagaac ctaatttatc tgttacccgg<br>cctgtggctc gcacagctta aaaatggtca aactttcccc ttcttgtctt<br>tttttcctca cattcatcag gttcttgtct tgatctttca agtgagtatt<br>aattaccgac cttggttctt cattgggaga gcattggaag ccgtggtgca<br>gcaaccacaa aacggttctt ccccttcgat accttcttgc ctgcctttca<br>atacaagtcg gctcgattag cggtggtcgc ccccgccagc ggagaacatg<br>gaactaaccc agaatgagag ctaagtggag aaagaagaga gtcagacgac<br>tcaagcgaaa gcgccgcaag gtccgagctc gatccaaata agcggttttt<br>aacggagatt taacactaaa togaagaact tttcccgttt catttgcgaa<br>tgagctcgtt aacaaaatcc cccagttttt ttatccagct gtaaggattg<br>acattagtaa tgaattattg tttggtatat ttaaatctgt agttcctttc<br>tgtccgtgtc ggcaactgtc gtactcgtga tttacttgta ttgacgaata<br>cttactgtag cgcactctgc tgctactggt cgtaaggatg tgctatttcg<br>gtgtatggtg ggtttttggg gggtcggaac cgaagactgt tacacgggca<br>cggctcgttg tgtacacgca cagagctctt gcgagtcatg ttgtagctag<br>ctcgtcgtgt tcaggaactg ttcgatggtt cggagagagt cgccgcccag<br>aacatacgcg caccgatgtc agcagacagc cttattacaa gtatattcaa<br>gcaagtatat ccgtagggtg cgggtgattt ggatctaagg ttcgtactca<br>acactcacga gcagcttgcc tatgttacat ccttttatca gacataacat<br>aattggagtt tacttacaca cggggtgtac ctgtatgagc accacctaca<br>attgtagcac tggtacttgt acaaagaatt tattcgtacg aatcacaggg<br>acggccgccc tcaccgaacc agcgaatacc tcagcggtcc cctgcagtga<br>ctcaacaaag cgatatgaac atcttgcgat ggtatcctgc tgatagtttt<br>tactgtacaa acacctgtgt agctccttct agcattttta agttattcac<br>acctcaaggg gagggataaa ttaaataaat tccaaaagcg aagatcgaga<br>aactaaatta aaattccaaa aacgaagttg gaacacaacc ccccgaaaaa<br>aaacaacaaa caaaaaaccc aacaaaataa acaaaaacaa aataaatata<br>taactaccag tatctgacta aaagttcaaa tactcgtact tacaacaaat<br>agaaatgagc cggccaaaat tctgcagaaa aaaatttcaa acaagtactg<br>gtataattaa attaaaaaac acatcaaagt atcataacgt tagttatttt<br>atttatttta ataaaagaaa acaacaagat gggctcaaaa ctttcaactt<br>atacgataca taccaaataa caatttagta tttatctaag tgcttttcgt<br>agataatgga atacaaatgg atatccagag tatacacatg gatagtatac<br>actgacacga caattctgta tctctttatg ttaactactg tgaggcatta<br>aatagagctt gatatataaa atgttacatt tcacagtctg aacttttgca<br>gattacctaa tttggtaaga tattaattat gaactgaaag ttgatggcat<br>ccctaaattt gatgaaagat gaaattgtaa atgaggtggt aaaagagcta<br>cagtcgtttt gttttgagat accatcatct ctaacgaaat atctattaaa<br>aatctcagtg tgatcatgag tcattgccat cctggaaaat gtcatcatgg<br>ctgatatttc taactgttta cttgagataa atatatattt acaagaactt<br>cccttgaaat taatttagat ataaaatgtt tgcgggcaag ttactacgag<br>gaataaatta tatctagagg ttccgcttcc tcgctcactg actcgctgcg<br>ctcggtcgtt cggctgcggc gagcggtatc agctcactca aaggcggtaa<br>tacggttatc cacagaatca ggggataacg caggaaagaa catgtgagca<br>aaaggccagc aaaaggccag gaaccgtaaa aaggccgcgt tgctggcgtt<br>tttccatagg ctccgccccc ctgacgagca tcacaaaaat cgacgctcaa<br>gtcagaggtg gcgaaacccg acaggactat aaagatacca ggcgtttccc<br>cctggaagct ccctcgtgcg ctctcctgtt ccgaccctgc cgcttaccgg<br>atacctgtcc gcctttctcc cttcgggaag cgtggcgctt tctcatagct<br>cacgctgtag gtatctcagt tcggtgtagg tcgttcgctc caagctgggc<br>tgtgtgcacg aaccccccgt tcagcccgac cgctgcgcct tatccggtaa<br>ctatcgtctt gagtccaacc cggtaagaca cgacttatcg ccactggcag<br>cagccactgg taacaggatt agcagagcga ggtatgtagg cggtgctaca<br>gagttcttga agtggtggcc taactacggc tacactagaa ggacagtatt<br>tggtatctgc gctctgctga agccagttac cttcggaaaa agagttggta<br>gctcttgatc cggcaaacaa accaccgctg gtagcggtgg tttttttgtt |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | tgcaagcagc agattacgcg cagaaaaaaa ggatctcaag aagatccttt |
| | gatcttttct acggggtctg acgctcagtg gaacgaaaac tcacgttaag |
| | ggattttggt catgagatta tcaaaaagga tcttcaccta gatcctttta |
| | aattaaaaat gaagttttaa atcaatctaa agtatatatg agtaaacttg |
| | gtctgacagt taccaatgct taatcagtga ggcacctatc tcagcgatct |
| | gtctatttcg ttcatccata gttgcctgac tccccgtcgt gtagataact |
| | acgatacggg agggcttacc atctggcccc agtgctgcaa tgataccgcg |
| | agacccacgc tcaccggctc cagatttatc agcaataaac cagccagccg |
| | gaagggccga gcgcagaagt ggtcctgcaa ctttatccgc ctccatccag |
| | tctattaatt gttgccggga agctagagta agtagttcgc cagttaatag |
| | tttgcgcaac gttgttgcca ttgctgcagg catcgtggtg tcacgctcgt |
| | cgtttggtat ggcttcattc agctccggtt cccaacgatc aaggcgagtt |
| | acatgatccc ccatgttgtg caaaaaagcg gttagctcct tcggtcctcc |
| | gatcgttgtc agaagtaagt tggccgcagt gttatcactc atggttatgg |
| | cagcactgca taattctctt actgtcatgc catccgtaag atgcttttct |
| | gtgactggtg agtactcaac caagtcattc tgagaatagt gtatgcggcg |
| | accgagttgc tcttgcccgg cgtcaacacg ggataatacc gcgccacata |
| | gcagaacttt aaaagtgctc atcattggaa aacgttcttc ggggcgaaaa |
| | ctctcaagga tcttaccgct gttgagatcc agttcgatgt aacccactcg |
| | tgcacccaac tgatcttcag catcttttac tttcaccagc gtttctgggt |
| | gagcaaaaac aggaaggcaa aatgccgcaa aaaagggaat aagggcgaca |
| | cggaaatgtt gaatactcat actcttcctt tttcaatatt attgaagcat |
| | ttatcagggt tattgtctca tgagcggata catatttgaa tgtatttaga |
| | aaaataaaca aataggggtt ccgcgcacat ttccccgaaa agtgccacct |
| | gacgtctaag aaaccattat tatcatgaca ttaacctata aaaataggcg |
| | tatcacgagg ccctttcgtc tggcctagga agcgacttcc aatcgctttg |
| | catatccagt accacaccca caggcgtttg tgctactcta ctgatagcaa |
| | tagatgcgtc ataattggtt ggcccgctga gcctccacag gatactattg |
| | cacataccct ggtcatgtgc agatcagctc atttgtggag actctggagt |
| | aacttagacg acgcctggtt caattgccgc aatgtgcgcc cacgcagata |
| | atgtattgag gggtggagcg cctcttgggg acttgctgta cttgtacggg |
| | atattaaacg cactcagcaa gaccatgacg taaaacacac ctactgtacg |
| | atacgtactg taggtattgt actcgtaccc ggtactacaa atagtacgat |
| | actatacgga gtgtatttgt accttgatat acgactggcg gagtgaagag |
| | aaggagttga acaagaccag atggggatat cagccccagt gctttgtatt |
| | acaagtacga gtacttaata gatactgtaa ggctattgat acggatggca |
| | gtaagtcatt gagtaagcaa ttgtggccca gcatctcccc tacgtacttg |
| | taccataccc catggagaca ccaatggtct ttcacgcaca ctgtcgtgtg |
| | ctgtatcgca gaatcgggtg tccaaccaaa tgccgttacc cccacgtcac |
| | agccgataga cagatacacc atcaatacca gcaggttgta tcatgcggtt |
| | ggctgaaggt aagctgattg gtctaaaaac tgtagctgtc ctaattcaac |
| | gagcgctatt tggggccaac cacctcggcc aagcggcctt taatctgcgt |
| | gccccagagg cgtctaatga ggctctggcc gccactgtag gagtgtttct |
| | ctgtgcgcac acgcagtttt gagtttgggc gactttccct ttttcccaat |
| | tgcgtacaca cacagctccg agctaagcgc tgtccttgaa ccttctccct |
| | cttttccctc tttttctctt ccccttcccc tcctccacat taaggccaaa |
| | tcctgaattg caccaactag tacaacgaca acaatggaca agaagtactc |
| | catcggtttg gacattggta ctaactctgt cggctgggcc gtcatcaccg |
| | acgagtacaa ggttccctcc aagaagttca aggtccttgg caacaccgac |
| | cgacactcta tcaagaagaa cctgatcggt gctctgctgt tcgactctgg |
| | cgagactgcc gaggccaccc gactgaagcg aaccgctcga cgccgataca |
| | cccgacgaaa gaaccgaatc tgttacctcc aggagatctt cagcaacgag |
| | atggctaagg tcgacgactc cttcttccac cgactcgagg agtctttcct |
| | ggtcgaagag gataagaagc acgagcgaca ccccatcttc ggcaacattg |
| | ttgatgaggt tgcctaccat gagaagtacc ccaccatcta ccacctccga |
| | aagaagctcg tcgactccac tgacaaggct gacctccgac tcatctacct |
| | tgctctcgcc cacatgatca agttccgagg tcacttcctc attgagggtg |
| | atctcaaccc cgacaactcc gacgttgaca agctgttcat ccagctcgtc |
| | cagacctaca accagctctt tgaggagaac cctatcaacg cttctggtgt |
| | tgacgccaag gccattctct ccgcccgact ctctaagtcc cgacgactcg |
| | agaacctcat tgcccagctg cccggcgaga agaagaacgg cctcttcggt |
| | aacctgattg ctctctctct tggtctgacc cccaacttca agtccaactt |
| | tgacctcgcc gaggacgcca agctccagct gtccaaggac acctacgatg |
| | acgatctgga caacctcctg gcccagatcg gtgaccagta cgccgatctc |
| | ttccttgccg ccaagaacct ctccgacgcc atcctgctct ccgacatcct |
| | ccgagtcaac accgagatta ccaaggctcc tctgtctgcc tctatgatca |
| | agcgatacga cgagcaccac caggatctca ctcttctcaa ggctctcgtc |
| | cgacagcagc tccccgagaa gtacaaggag attttctttg accagtccaa |
| | gaacggttac gctggctaca ttgacggtgg tgcttcccag gaagagtttt |
| | acaagttcat caagcctatt ctggagaaga tggacggtac cgaggagctg |
| | ctcgtcaagc tcaaccgaga ggacctcctt cgaaagcagc gaaccttcga |
| | taacggctcc atcccccacc agatccacct gggtgagctc cacgccattc |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | tccgaagaca agaggacttc taccccttcc taaaggataa ccgagagaag |
| | atcgagaaga ttctcacctt ccgaatcccc tactacgtcg gtcccctcgc |
| | tcgaggtaac tcccgatttg cttggatgac ccgaaagtcc gaggagacta |
| | tcacccccctg gaactttgaa gaggtagtcg acaagggtgc ctccgcccag |
| | tctttcattg agcggatgac caacttcgat aagaacctcc ccaacgagaa |
| | ggtccttccc aagcactctc tcctctacga gtacttcacc gtctacaacg |
| | agctgaccaa ggtcaagtac gttaccgagg gcatgcgaaa gcccgctttc |
| | ctctctggtg agcagaagaa ggccattgtc gacctcctgt tcaagactaa |
| | ccgaaaagtc accgtcaagc agctcaagga agactacttc aagaagattg |
| | agtgcttcga ctccgtcgag atttccggtg tcgaggaccg attcaacgcc |
| | tccctcggca cctaccacga tcttctgaag atcatcaagg acaaggactt |
| | tcttgataac gaggagaacg aggacattct cgaggacatc gtcctcaccc |
| | tcaccctttt cgaggatcga gagatgatcg aggagcgact caagacctac |
| | gcccatctct tcgacgacaa ggtcatgaag caactcaagc gacgacgata |
| | cactggctgg ggccgacttt cccgaaagct catcaacggc atccgagaca |
| | agcagtctgg caagaccatc ctggacttcc tgaagtccga cggtttcgcc |
| | aaccgaaact tcatgcagct catccacgac gactctctta ccttcaaaga |
| | ggatatccag aaggcccagg tttctggcca gggcgactcc ctccacgagc |
| | acattgccaa cctcgccgga tcccccgcca tcaaaaaggg tatcctccag |
| | accgtcaagg ttgtcgacga actcgtgaag gtcatgggcc gacacaagcc |
| | cgagaacatc gttatcgaga tggcccgaga gaaccagacc acccagaagg |
| | gtcagaagaa ctcccgagag cgaatgaagc gaatcgaaga gggtatcaag |
| | gagctcggtt cccagattct caaggagcac cccgtcgaga acacccagct |
| | ccagaacgag aaactctacc tgtactacct ccagaatggc cgagacatgt |
| | acgttgacca ggagctcgac atcaaccgac tctccgacta cgacgtcgac |
| | cacattgttc ctcagtcctt cctcaaggac gactccatcg acaacaaggt |
| | tctgacccga tctgacaaga accgaggtaa gtccgacaac gttccctccg |
| | aagaggtcgt taagaagatg aagaactact ggcgacagct tctcaacgcc |
| | aaactgatca cccagcgaaa gtttgacaac ctcaccaagg ccgagcgagg |
| | tggtctgtcc gagctggaca aggccggctt cattaagcga cagctggtcg |
| | agactcgaca gatcaccaag cacgtcgccc agatcctcga ctcccgaatg |
| | aacaccaagt acgacgagaa cgacaagctc atccgggagg tcaaggtcat |
| | caccctgaag tctaagcttg tctccgactt ccgaaaggac ttccagttct |
| | acaaggtccg agagatcaac aactaccacc acgcccacga cgcctacctc |
| | aacgccgttg ttggtaccgc cctcatcaag aagtatccca agctcgagtc |
| | cgagttcgtt tacggcgact acaaggttta cgatgtccga aagatgattg |
| | ccaagtccga gcaggagatc ggtaaggcca ccgccaagta ctttttctac |
| | tccaacatca tgaatttctt caagaccgag atcactctcg ccaacggtga |
| | gattcgaaag cgacccctga ttgagactaa tggtgagact ggtgagatcg |
| | tctgggataa gggccgagac ttcgccaccg tccgaaaggt cctgtccatg |
| | ccccaggtca acattgtcaa gaagaccgag gtccagaccg gtggcttctc |
| | caaggagtcc attctcccca agcgaaactc cgacaaactc atcgcccgta |
| | agaaggactg ggatccgaag aagtacggtg gtttcgattc tcccaccgtt |
| | gcctactccg tcctcgttgt tgctaaagtc gagaagggta agtctaagaa |
| | actcaagtcc gtgaaggagc tactcggtat caccatcatg gagcgatctt |
| | cttttgagaa gaaccccatt gacttcctcg aggccaaggg ttacaaagag |
| | gtcaagaagg acctgattat caagctgccc aagtactccc tctttgagct |
| | cgagaacggc cgaaagcgaa tgctggcttc cgctggtgag ctgcagaagg |
| | gcaacgagct cgctctgccc tccaagtacg tcaacttcct ctacctggcc |
| | tcccactacg agaagctcaa gggctccccc gaggacaacg agcagaagca |
| | gctgttcgtt gagcagcaca agcactacct cgacgagatc atcgagcaga |
| | tctccgagtt ctccaagcga gtcatcctcg ctgacgccaa ccttgataag |
| | gttctctctg cttacaacaa gcaccgggac aagcccatcc gagagcaggc |
| | cgagaatatc atccacctct tcactctcac caacctcggc gctcctgctg |
| | ccttcaagta cttcgacacc accattgacc gaaagaggta cacctccacc |
| | aaggaagtcc tcgacgccac cctgatccac cagtccatca ccggcctcta |
| | cgaaacccga atcgacctct cccagctcgg cggtgactct cgagccgacc |
| | ccaagaagaa gcgaaaagtc taaatatccg aagatcaaga gcgaagcaag |
| | ttgtaagtcc aggacatgtt tcccgcccac gcgagtgatt tataacacct |
| | ctctttttg acacccgctc gccttgaaat tcatgtcaca taaattatag |
| | tcaacgacgt ttgaataact ttcttgtag ttcgatgatg atcatatgat |
| | tacattaata gtaattactg tatttgatat atatactaat tacaatagta |
| | catattagaa catacaatag ttagtgccgt gaagtggctt aaaataccgc |
| | gagtcgatta cgtaatatta ttacctcttg cccatcgaac gtacaagtac |
| | tcctctgttc tctccttcct ttgctttgtg cacgaagaac tgcggtcagg |
| | tgacacaact ttttccatct cagggtgtgt cgcgtgtgct tcatccaaac |
| | tttagttggg gttcgggttc gcgcgagatg atcacgtgcc ctgatttggt |
| | gtcgtccccc gtcgcgctgc gcacgtgatt tatttatttc cggtggctgc |
| | tgtctacgcg gggccttctc tgcccttctg tttcaacctt cgggcggttc |
| | tcgtaaccag cagtagcaat ccatttcgaa actcaaagag ctaaaaacgt |
| | taaacctcag cagtcgctcg acgaatgggc tgcggttggg aagcccacga |
| | ggcctatagc cagagcctcg agttgacagg agcccagacg ccttttccaa |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | cggcaacttt tatataaaat ggcaatgtat tcatgcaatt gcggccgtgt<br>caggttggag acactggacc acactctcca ttgcttcctg aggagatgga<br>tcattgctag tgcatctacg cgcagcaatc ccgcaagctc gacaaccgta<br>gatgggcttt ggtgggccaa tcaattacgc aacccgcacg ttaaattgta<br>tgaggaagga aggccacggt acaaagtggg tggtcttcac ccagtggttg<br>ttggtggcgt catgcagacc atggccgcca gtgtgctgga attgaatatt<br>taccgttcgt ataatgtatg ctatacgaag ttataccggt ctcgtagtgt<br>tcacgttcag ttcacggtga gcttaaaact atcttcaaga agagatttga<br>gacctgattt atacttgcag caatgtttac ttcttatcgc gatacacgaa<br>tgtgatacgg atcaaagtaa gcaggactac gataagataa cgaatgcggt<br>gcagtccatg tcgattaggt atagatacat ttattttgtg ttatgttaca<br>ttttgggggg atactgtcct acttgtagta cctacttgta gtggcgcgtt<br>aggggcaggg catgctcatg tagagcgcct gccgctcgcc gtccgaggcg<br>gtgccgtcgt acagggcggt gtccaggccg cagagggtga accccatccg<br>ccggta |
| 10 | GCGGAGCCTAGGCCGGCCAGCGTGGCGCGTGGCCATATTGGCCAGCAGCTTACTACAGC<br>TCAGCCAAAGTGGATCATGATGGACGGAAATATCGGACTGGAGGCCAAAAAGGAGGTGC<br>TCAAATACGCACGGGACAAGTCTGCACAGGTGGCATTCGAACCCACGTCTGTCCCCAAA<br>GCCGCTGCTCTTTCCGAGCTCAATCTGCCCGTTTACCCCAACAACTCCATTGCCTTAGC<br>CACCCCCAACACTGCAGAGCTCGAGGCCATGTTCGAGGCATTCCACGAGAAGGGCCGAT<br>TTGACGTTGACGACTGGTTTCCAGTCATAGACGGTCTTGCTCTCGGAGCTGACTTTAGA<br>AACGGAGCCACCATGTTGTCGCACCAACATCGTGGACTCAAAGCTATTCTCGAACAAGG<br>AACTCTGGCCCAGGCAATCCACATGCTACCATACATCCCAACTTTGATCATCAAGGGCG<br>GAGCCAACGGCGTCGTCGTCTTCCAACTCATTGATGATATCGAGTCTGCCATTCATTCA<br>CAGCGTTCTGCTTCCAATAAAACGCCTGGCCTGTTCCAGAAGGGCAACGCTGCGAGTGG<br>AAACACCAAGGTCGGCGTCTACATGCAGTACTTTGAGCCCGAAGAAGTGGGCAGTCAGT<br>CGATTGTAAGCGTGACTGGAGCTGGAGACACTCTGTTTGGAACCCTGGCCATGGAGATT<br>GTCAAGGACGAGTCCTGGTTGAACGATATGGGAGACAAGAAGAGTGCAGTTGTTTCTCG<br>AGCCATGAACAATGCTGTGAAGACTATTCAGAGTAAGGACGCTGTCTGCAAGAGCATCC<br>TTTAAGTGATTTGCCATGCTTTCTCTTCTTCCACGATGTAAATACTTATTTTACACACT<br>ACTGTGCAGTAGCAAATACAGAACAAGAGTTGTCGCCTATTGACAGTACAGTACGAGTA<br>GTGTATGTACAGTAGTTATACAATATCTATGTGAAATTCGTCGGCAGCTTTCGGCTGAT<br>GAACTACGAGTTCTTCGTAATAAATCATCAACGTAATAAGCTTGGTACCAGAGACGGGT<br>TGGCGGCGTATTTGTGTCCCAAAAAACAGCCCCAATTGCCCCAATTGACCCCAAATTGA<br>CCCAGTAGCGGGCCCAACCCCGGCGAGAGCCCCCTTCACCCCACATATCAAACCTCCCC<br>CGGTTCCCACACTTGCCGTTAAGGGCGTAGGGTACTGCAGTCTGGAATCTACGCTTGTT<br>CAGACTTTGTACTAGTTTCTTTGTCTGGCCATCCGGGTAACCCATGCCGGACGCAAAAT<br>AGACTACTGAAAATTTTTTTGCTTTGTGGTTGGGACTTTAGCCAAGGGTATAAAAGACC<br>ACCGTCCCCGAATTACCTTTCCTCTTCTTTTCTCTCTCTCCTTGTCAACTCACACCCGA<br>AATCGTTAAGCATTTCCTTCTGAGTATAAGAATCATTCGCTAGCCACAAAAATGGGTGA<br>TCTCGATGCCCGAGGAACCTCTGCTCACCCCGAGCTCTCTGAGCGACCTTCTATTATGC<br>CTTCTATGTCTGATATTCAGGACCCTTCTGGTGATGACAAGGCTACTCCCCGAGGATCT<br>GCTGCTGGTCTGCCCCAGCTTGAGCTTGCTGGACACGCCCGACGACTTGGCCACCTTGA<br>GAACTTCTTTGCTGTCCAGGCTCGACAGCAGATTTACTCTTCTTTTGCTGTTTTTTGTG<br>AGTTTGACACTGCTTGTTCTCTCGCTCAGCTTGCTTCTGCTGTGCGAAACGTTTGTCTT<br>TCTAACCCCCTTCTCCTTCACACTGTTGAGCCTAAGCACCCTGACATCGCTGGATTCTA<br>CCACTCTGACGAGTACCTTTCCCGACCTTGGCCTCAGCACGATTACATGCGAGTTCTTC<br>GAGAGGTTCACGTCGCTGACGTTGTTATGAACGGACAGAAGGAGCACGCTCACGTTGTT<br>CGAGATGCTGTTGACGTTTTTCAGGCTCACGGAAACCAGGTTACTTCTGAGCTCCTTGA<br>GCTTATGACTCAGATTGAGATTCCTCACGCTTCTCAGACTCGACCCTCTTGGCGACTTC<br>TCTGTTTTCCCCACGGAGAGGCTAACCGATGGCGAACCTTTGCTTTTGTTTCTAACCAC<br>TGTTCTTCTGATGGTCTTTCTGGTCTTAACTTCTTTCGAGATCTCCAGAAGGAGCTTGC<br>TCACGGCCCCACCTCTGGTGCTCCTGGTGCCCCCGGAGCTTCCGGAGTTATTTTCGATT<br>ACGCTCAGGACGCTGCTACCCTGCCCAAGCTGCCCCCTCCCATTGATCAGAAGCTCGAT<br>TACCGACCTTCTAAGAAGGCTCTTCTCGGCCTTCTCGCTGGCAAGTTCGTTCGAGAGAA<br>GCTCGGTTACGTTTCTGCTGCTCCTCCCACTACCCCTACCTCTGACCTTGCTCACCCTG<br>AGGGTCACCAGTACTACTGTTACCTTGTTAACGTTCCCACTTCTTCTGTTGCCCACATT<br>AAGACTCAGGTGCGAGAGAACGTTCCTCACAAGTGTACTCTCACTCCCTTTCTCCAGGC<br>TTGTTGGCTTGTTTCTCTGTTCAAGTACGGTCGAGTTTTTTCTGGTTCTTGGCTTGAGC<br>GATACACCGATGTTCTTGTTGCTATGAACACTCGACAGCTTCTCCCCGAGGACCTTGAG<br>CTTCAGCGACAGTACCGATACGGTTCTAACATTGGAGCTGTTCGATACAACTACCCTAT<br>TGCTCCCCTTGACGTTCGAGATAACGATCAGAAGTTCTGGTCCCTTGTTGAGTCTTACC<br>GACTTGCCCTTTCTGATGCCCGAGATAAGAACGATTACCTTTACGCTCTTGGTGCTCTT<br>ATGCTCCCTGAGATTTACGAGAAGAAGAACGTTGATGCTGTTGTTAACGATACCATTCT<br>TAACCAGCGACGACAGGGAACCCTTCTTTCTAACGTTGGTTACGTTCGAGATGAGCAGC<br>CCACTGCTTTTGCTATTAAGAACCACGTTTTTTCTCAGGGAGTTGGAGCTAACCGAAAC<br>GCTTTTGTTCTTAACATTTGTGCTACCGATCAGGGTGGTCTTAACATCGCTATTTCTAT<br>TGCTAAGGGAACCCTTGCTTCTCGACAGGAGGGACAGGAGCTTTGTGATATTTTTAAGT<br>CTACTCTCCTTCGATTTTAAACGCGTCTATCCGAAGATCAAGAGCGAAGCAAGTTGTAA<br>GTCCAGGACATGTTTCCCGCCCACGCGAGTGATTTATAACACCTCTCTTTTTGACACC<br>CGCTCGCCTTGAAATTCATGTCACATAAATTATAGTCAACGACGTTTGAATAACTTGTC |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
| --- | --- |
| | TTGTAGTTCGATGATGATCATATGATTACATTAATAGTAATTACTGTATCTGTACCTGC |
| | TGTGGACCACGCACGGCGGAACGTACCGTACAAATATTTTCTTGCTCACATGACTCTCT |
| | CTCGGCCGCGCACGCCGGTGGCAAATTGCTCTTGCATTGGCTCTGTCTCTAGACGTCCA |
| | AACCGTCCAAAGTGGCAGGGTGACGTGATGCGACGCACGAAGGAGATGGCCCGGTGGCG |
| | AGGAACCGGACACGGCGAGCCGGCGGGAAAAAAGGCGGAAAACGAAAAGCGAAGGGCAC |
| | AATCTGACGGTGCGGCTGCCACCAACCCAAGGAGGCTATTTTGGGTCGCTTTCCATTTC |
| | ACATTCGCCCTCAATGGCCACTTTGCGGTGGTGAACATGGTTTCTGAAACAACCCCCCA |
| | GAATTAGAGTATATTGATGTGTTTAAGATTGGGTTGCTATTTGGCCATTGTGGGGGAGG |
| | GTAGCGACGTGGAGGACATTCCAGGGCGAATTGAGCCTAGAAAGTGGTACCATTCCAAC |
| | CGTCTCAGTCGTCCGAATTGATCGCTATAACTATCACCTCTCTCACATGTCTACTTCCC |
| | CAACCAACATCCCCAACCTCCCCCACACTAAAGTTCACGCCAATAATGTAGGCACTCTT |
| | TCTGGGTGTGGGACAGCAGAGCAATACGGAGGGGAGATTACACAACGAGCCACAATTGG |
| | GGAGATGGTAGCCATCTCACTCGACCCGTCGACTTTTGGCAACGCTCAATTACCCACCA |
| | AATTTGGGCTGGAGTTGAGGGGACCGTGTTCCAGCGCTGTAGGACCAGCAACACACACG |
| | GTATCAACAGCAACCAACGCCCCCGCTAATGCACCCAGTACTGCGCAGGTGTGGGCCAG |
| | GTGCGTTCCAGATGCGAGTTGGCGAACCCTAAGCCGACAGTGTACTTTTTGGGACGGGC |
| | AGTAGCAATCGTGGGCGTAGACCCCGGTGTATATAAAGGGGTGGAGAGGACGGATTATT |
| | AGCACCAACACACACACTTATACTACATGCTAGCCACAAAAATGCTCTCTTTCTTCTGG |
| | CGAAACGGTATCGAGACTCCCGAGCCCCTCAAGGCTGACGTTTCCGGCTCTATCCCTCC |
| | CTGGCTTCAGGGAACCCTTCTCCGAAACGGTCCTGGTCTGTTCTCCGTTGGCAACACTT |
| | CCTACAAGCACTGGTTCGATGGTATGGCTCTCATTCACTCCTTCACCTTTAAGGATGGT |
| | GAGGTTTTTTACCGATCTAAGTACCTGAAGTCTGAGACTTACAAGAAGAACATCGCTGC |
| | CGACCGAATCGTTGTGTCTGAGTTCGGAACCATGGTGTACCCCGATCCCTGCAAGAACA |
| | TTTTCTCCCGAGCCTTCTCTTACATGATGAACGCCATTCCTGACTTTACCGATAACAAC |
| | CTCATTAACATCATTAAGTACGGTGAGGATTACTACGCCTCCTCTGAGGTCAACTACAT |
| | CAACCAGATTGACCCCCTGACCCTTGAGACTCTCGGACGAACTAACTACCGAAACCACA |
| | TTGCCATCAACCTTGCCACTGCTCACCCTCACTACGACGAGGAGGGTAACACTTACAAC |
| | ATGGGCACTGCTATTATGAACCTCGGTCGACCCAAGTACGTGATTTTCAAGGTGCCCGC |
| | CAACACCTCTGATAAGGAGAACAAGAAGCCTGCCCTCTCTGAGGTGGAGCAGGTTTGCT |
| | CCATTCCCATCCGACCCTCCCTTTACCCTTCTTACTTCCACTCTTTTGGCATGACTGAG |
| | AACTACATCATCTTCGTTGAGCAGGCCTTCAAGCTGGACATCGTCAAGCTGGCTACTGC |
| | TTACTTCCGAGATATTAACTGGGGATCTTGCCTTAAGTTCGACCAGGATGACATTAACG |
| | TGTTCCACCTGGTCAACAAGAAGACTGGTAAGGCTGTGTCCGTGAAGTACTACACTGAC |
| | CCCTTTGTTACCTTCCACCACATCAACGCTTACGAGGACGATGGCCACGTCGTCTTCGA |
| | TCTCATTACTTACAAGGACTCTAAGCTGTACGATATGTTCTACATTCAGAACATGAAGC |
| | AGGACGTCAAGCGATTTATTGAGACTAACAAGGACTTCGCTCAGCCCGTGTGCCAGCGA |
| | TTTGTCCTTCCCGTCAACGTTGATAAGGAGACTCCTCAGGACATCAACCTTGTCAAGCT |
| | GCAGGACACCACTGCCACTGCTGTCCTGAAGGAGGACGGCTCTGTCTACTGCACCCCTG |
| | ACATCATTTTTAAGGGTCTTGAGCTCCCTGCTATCAACTACAAGTTTAACTCTAAGAAG |
| | AACCGATACTTCTACGGCACCCGAGTGGAGTGGTCCCCTTACCCTAACAAGGTCGCTAA |
| | GGTGGACGTTGTTACTCGAACCCACAAGATTTGGACTGAGGAGGAGTGTTACCCTTCTG |
| | AGCCTGTCTTTATTGCCTCCCCTGACGCCGTTGATGAGGATGACGGTGTGATTCTTTCT |
| | TCTGTGGTTTCTTTCAACCCCCAGCGACCCCCTTTCCTGGTTGTCCTCGATGCTAAGTC |
| | CTTCAAGGAGATTGCTCGAGCTACCATCGATGCCTCTATTCACATGGACCTTCACGGCC |
| | TTTTCATCCACGACAAGTCTACCTAAGTTTTTTGATCAATGATCCAATGGCTTTCACAT |
| | ACCCCCCCACGCCTATAATTAAAACACAGAGAAATATAATCTAACTTAATAAATATTAC |
| | GGAGAATCTTTCGAGTGTTCAGCAGAAATATAGCCATTGTAACAAAAGCCGGCTATCGA |
| | CCGCTTTATCGAAGAATATTTCCCGCCCCCCAGTGGCCAAACGATATCGGTCAGAAGGG |
| | GCAGCTCTAAACGAAGAACTGCGGTCAGGTGACACAACTTTTTCCATCTCAGGGTGTGT |
| | CGCGTGTGCTTCATCCAAACTTTAGTTGGGGTTCGGGTTCGCGCGAGATGATCACGTGC |
| | CCTGATTTGGTGTCGTCCCCCGTCGCGCTGCGCACGTGATTTATTTATTTCCGGTGGCT |
| | GCTGTCTACGCGGGGCCTTCTCTGCCCTTCTGTTTCAACCTTCGGGCGGTTCTCGTAAC |
| | CAGCAGTAGCAATCCATTTCGAAACTCAAAGAGCTAAAAACGTTAAACCTCAGCAGTCG |
| | CTCGACGAATGGGCTGCGGTTGGGAAGCCCACGAGGCCTATAGCCAGAGCCTCGAGTTG |
| | ACAGGAGCCCAGACGCCTTTTCCAACGGCAACTTTTATATAAAATGGCAATGTATTCAT |
| | GCAATTGCGGCCGTGTCAGGTTGGAGACACTGGACCACACTCTCCATTGCTTCCTGAGG |
| | AGATGGATCATTGCTAGTGCATCTACGCGCAGCAATCCCGCAAGCTCGACAACCGTAGA |
| | TGGGCTTTGGTGGGCCAATCAATTACGCAACCCGCACGTTAAATTGTATGAGGAAGGAA |
| | GGCCACGGTACAAAGTGGGTGGTCTTCACCCAGTGGTTGTTGGTGGCGTCATGCAGACC |
| | ATGCATTGGGGATAGCACAGGGTTGGGGTGTCTTGTGGACTCAATGGGTGAAAGGAGAT |
| | GGAAAAGGGCGGTGAAAAGTGGTAGAATCGAAATCCCTGACGTCAATTTATAAAGTAAA |
| | ATGCGTTTCTGCCATTTTGCTCCCCTCCTTCTTTCGCAATCGCCTCCCCAAAAGTTGTC |
| | GTGGCAGTACACATGCTTGCATACAATGAAGCTAATCCGGCTTGCTCAGTAGTTGCTAT |
| | ATCCAGGCATGGTGTGAAACCCCTCAAAGTATATATAGGAGCGGTGAGCCCCAGTCTGG |
| | GGTCTTTTCTCTCCATCTCAAAACTACTTTCTCACATGCTAGCCACAAAAATGACCACT |
| | AAGTACACTTCCGTTCACGAGTCTCCCAACGGCCCTGGTGACGCTCGACCCACCGCTTC |
| | CCAGATTATCGACGATTACAACCTTGAGGGAGAGCTTTCTGGCAAGACTGTTCTCGTCA |
| | CCGGCTGTTCCTCTGGTATTGGTGTTGAGACTGCCCGAGCTATTTACCGAACTGGTGCC |
| | ACCCTTTACCTCACTGCCCGAGATGTCGATAAGGCCAAGACCGTTCTTCCCGACCTTGT |
| | TGACACTTCCCGAGTCCACTTTCTCCACCTTGACCTTAACTCTCTGGAGTCTGTTCGAG |
| | GTTTTGCTGAGAACTTCAAGTCTAAGTCCACTCAGCTTCACATTCTCATCGAGAACGCT |
| | GGCGTGATGGCCTGTCCCGAGGGCCGAACCGTCGATGGTTTTGAGACTCAGTTTGGTAT |

TABLE 11-continued

| sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text. | |
|---|---|
| SEQ ID NO: | sequence 5' to 3' |
| | CAACCACCTTGCTCACTTTCTCCTCTTTTACCTCCTCAAGGATACCCTTCTCAACTCTT<br>CTACCCCCGCTTTCAACTCCCGAGTTGTCATCCTCTCTTCTTGTGCTCACCAGGCTGGT<br>TCCGTTCACCTTAACAACCTGTCTCTTGAGGGTGGATACGAGCCTTGGAAGTCTTACGG<br>CCAGTCCAAGACTGCCAACCTTTGGACTGCCCGAGAGATCGAGAAGCGATTTGGTGCTT<br>CCGGTATCCACTCTTGGGCTGTTCACCCCGGTTCCATCGCTACTGAGCTTCAGCGACAC<br>GTTTCCGACGAGCTTAAGCAGAAGTGGGCTGACGATAAGGAGGGTGCCAAGCTGTGGAA<br>GTCCACCGAGCAGGGTGCCGCCACCACTGTCCTTGCTGCTGTTTCCCCTGAGCTTGAGG<br>GTAAGGGCGGTCTTTACCTTGAGGATACCCAGGTTGCCAAGCCCCCTGCCCGAGGAATG<br>TTTGGTGTTGCTGACTGGGCTTACGATGAGGATGGCCCCTCTAAGCTCTGGGCCAAGTC<br>TCTTGAGCTCCTTAAGCTCCAGTAAAGGTTAGACTATGGATATGTAATTTAACTGTGTA<br>TATAGAGAGCGTGCAAGTATGGAGCGCTTGTTCAGCTTGTATGATGGTCAGACGACCTG<br>TCTGATCGAGTATGTATGATACTGCACAACCTGTGTATCCGCATGATCTGTCCAATGGG<br>GCATGTTGTTGTGTTTCTCGATACGGAGATGCTGGGTACAAGTAGCTAATACGATTGAA<br>CTACTTATACTTATATGAGGCTTGAAGAAAGCTGACTTGTGTATGACTTATTCTCAACT<br>ACATCCCCAGTCACAATACCACCACTGCACTACCACTACACACTAGTGGTGTGTTCTGT<br>GGAGCATTCTCACTTTTGGTAAACGACATTGCTTCAAGTGCAGCGGAATCAAAAAGTAT<br>AAAGTGGGCAGCGAGTATACCTGTACAGACTGTAGGCGATAACTCAATCCAATTACCCC<br>CCACAACATGACTGGCCAAACTGATCTCAAGACTTTATTGAAATCAGCAACACCGATTC<br>TCAATGAAGGCACATACTTCTTCTGCAACATTCACTTGACGCCTAAAGTTGGTGAGAAA<br>TGGACCGACAAGACATATTCTGCTATCCACGGACTGTTGCCTGTGTCGGTGGCTACAAT<br>ACGTGAGTCAGAAGGGCTGACGGTGGTGGTTCCCAAGGAAAAGGTCGACGAGTATCTGT<br>CTGACTCGTCATTGCCGCCTTTGGAGTACGACTCCAACTATGAGTGTGCTTGGATCACT<br>TTGACGATACATTCTTCGTTGGAGGCTGTGGGTCTGACAGCTGCGTTTTCGGCGCGGTT<br>GGCCGACAACAATATCAGCTGCAACGTCATTGCTGGCTTTCATCATGATCACATTTTTG<br>TCGGCAAAGGCGACGCCCAGAGAGCCATTGACGTTCTTTCTAATTTGGACCGATAGCCG<br>TATAGTCCAGTCTATCTATAAGTTCAACTAACTCGTAACTATTACCATAACATATACTT<br>CACTGCCCCAGATAAGGTTCCGATAAAAAGTTCTGCAGACTAAATTTATTTCAGTCTCC<br>TCTTCACCACCAAAATGCCCTCCTACGAAGCTCGAGCTAACGTCCACAAGTCCGCCTTT<br>GCCGCTCGAGTGCTCAAGCTCGTGGCAGCCAAGAAAACCAACCTGTGTGCTTCTCTGGA<br>TGTTACCACCACCAAGGAGCTCATTGAGCTTGCCGATAAGGTCGGACCTTATGTGTGCA<br>TGATCAAGACCCATATCGACATCATTGACGACTTCACCTACGCCGGCACTGTGCTCCCC<br>CTCAAGGAACTTGCTCTTAAGCACGGTTTCTTCCTGTTCGAGGACAGAAAGTTCGCAGA<br>TATTGGCAACACTGTCAAGCACCAGTACAAGAACGGTGTCTACCGAATCGCCGAGTGGT<br>CCGATATCACCAACGCCCACGGTGTACCCGGAACCGGAATCATTGCTGGCCTGCGAGCT<br>GGTGCCGAGGAAACTGTCTCTGAACAGAAGAAGGAGGACGTCTCTGACTACGAGAACTC<br>CCAGTACAAGGAGTTCCTGGTCCCCTCTCCCAACGAGAAGCTGGCCAGAGGTCTGCTCA<br>TGCTGGCCGAGCTGTCTTGCAAGGGCTCTCTGGCCACTGGCGAGTACTCCAAGCAGACC<br>ATTGAGCTTGCCCGATCCGACCCCGAGTTTGTGGTTGGCTTCATTGCCCAGAACCGACC<br>TAAGGGCGACTCTGAGGACTGGCTTATTCTGACCCCCGGGGTGGGTCTTGACGACAAGG<br>GAGACGCTCTCGGACAGCAGTACCGAACTGTTGAGGATGTCATGTCTACCGGAACGGAT<br>ATCATAATTGTCGGCCGAGGTCTGTACGGCCAGAACCGAGATCCTATTGAGGAGGCCAA<br>GCGATACCAGAAGGCTGGCTGGGAGGCTTACCAGAAGATTAACTGTTAGAGGTTAGACT<br>ATGGATATGTAATTTAACTGTGTATATAGAGAGCGTGCAAGTATGGAGCGCTTGTTCAG<br>CTTGTATGATGGTCAGACGACCTGTCTGATCGAGTATGTATGATACTGCACAACCTGTG<br>TATCCGCATGATCTGTCCAATGGGGCATGTTGTTGTGTTTCTCGATACGGAGATGCTGG<br>GTACAAGTAGCTAATACGATTGAACTACTTATACTTATATGAGGCTTGAAGAAAGCTGA<br>CTTGTGTATGACTTATTCTCAACTACATCCCCAGTCACAATACCACCACTGCACTACCA<br>CTACACCTCGAGCATGCACACTATTATCACATTACTACATCCAAACCCCTACAGGGGGA<br>GGAGCTCTCCAATCAAATATGTACATTAACTATCTCTCGTAAATCATTGTTATAAGACC<br>GTCCGTGACTGTCTAAATCGGTTCATTCGTTGTAACAAATCAGTGTAACAACTCGTGGT<br>ACGCCCGGTTTGCTTCGCTCACGCTCCCCTAGATTTTCCGTCTAGGACACAACAAGCCC<br>TGGTGGATGACGTTCAACGCCTTCAGCGCGTCTTTTTCCTCAATAACACACGAGATGTT<br>AATTTCGTTGGCTCCCTGAGAAATCATCTCAATGTTAATACCTGCCTGGGCCAGAGTAG<br>AGAAGAACATGCCTGCACATCCGACCATGGCCTTCATTCTCGTTCCGATCAGCGACACA<br>ATGGTCATGCCTCGCTTCACATCTACTGTGCCGTACTTTCGCAGCTCCTCCACAGCCTG<br>CTTGAGGTTGGAGTCGGGAGCATGGAAGGCCATCGACACATGGACCTCAGAAGTGGAGA<br>TGAGATCGACGACAAGTTTCTGCTGGTCGAGAGTAGCAAAGATCTTGTTCAAGAAGCCA<br>TGACTCTTGGTTCGCTTATTCGAATGAACGTTGAGAACGGTGATATTCGATTTGGTAGT<br>GACAGCTGTAGGCTTCTTCTCGTCATCTACAGGAGCAGACACCTGGGGAGTGAATGAGC<br>CAGAGGACAGAGAAGTTAGCGAGTCGGTGGAAGAAGCCAGATCCTGGACATTGTTTTTC<br>GTTTTCAGGTTGCCCGAGCCGTCAGCAGATGGGTAGATGATAGTTCCTCCTCCCAGGGG<br>GTTTTCCACGTTTTTGATTCGGATAGGAATATGGGCCTTAATGACCTGCTCCATGGTGA<br>AGGGGTGGATGACTTCAGATCCGTAGTAGGTCAACTCAGCGGCCTCCTCGGGGGTAATG<br>ATGGGCAGCAGACGGGCAGTGGACACCTTTCTGGGATCGGCAGTGAAGACACCATCGAC<br>TTCTTTCCAGATCTGAAGCTCCTTGGCGTCCAGACCCACAGCCACCAGAGCAGCACACA<br>GATCGGTGTATCCTCGTCCGATCTGGCTTAGGAGGCCTCCCTTGACGGGGCCAAAGAAA<br>CCGGTCAACACGGGCACCATGTTTCCCTTGACAGGAGCAGAGTCCGTGTTAGGAGAGCC<br>GGGAAGAGTGATGATCTCGCCCAGAACACGTCCGAGGTCCGAATAGAACTTGGGATCTT<br>CGGCATTGGTGGTGGTAACTGCGTGAGACAGGTCAAAGTACCGTGCGTTAACACCAGCG<br>TCCCGCATAACTGCAGTCATGTACATGCAACTGAGCTTCTCCCCAATGGCCATGATGGA<br>GTCGAGTGTTCGGGGGGAGATCTCAGAAATGATTTCAGCAGCAGCCAGGATTCGCAACA<br>GCTGGTCGCACTCGCCGTTGATGTCGGCATTGAGGTTTTCGAGCAGTTCGGGGTTCTTG |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | ACGTCACGCTTAGCAGCTGCAAGATGGTCTTCTCGGATAGACTCAATGATGGGGTTGTA<br>GGCGTCTGATCCGAGAAGAGCAGAGTCAGCAGCAGCAATAAGACGGGTGGTGGTTCCCT<br>CGGCCTTGGTGGCCTCTAGATGGCCTCCTTGGCCCCATTCCAGCTGCATTAATGAATCG<br>GCCAACGCGCGGGGAGAGGCGGTTTGCGTATTGGGCGCTCTTCCGCTTCCTCGCTCACT<br>GACTCGCTGCGCTCGGTCGTTCGGCTGCGGCGAGCGGTATCAGCTCACTCAAAGGCGGT<br>AATACGGTTATCCACAGAATCAGGGGATAACGCAGGAAAGAACATGTGAGCAAAAGGCC<br>AGCAAAAGGCCAGGAACCGTAAAAAGGCCGCGTTGCTGGCGTTTTTCCATAGGCTCCGC<br>CCCCCTGACGAGCATCACAAAAATCGACGCTCAAGTCAGAGGTGGCGAAACCCGACAGG<br>ACTATAAAGATACCAGGCGTTTCCCCCTGGAAGCTCCCTCGTGCGCTCTCCTGTTCCGA<br>CCCTGCCGCTTACCGGATACCTGTCCGCCTTTCTCCCTTCGGGAAGCGTGGCGCTTTCT<br>CATAGCTCACGCTGTAGGTATCTCAGTTCGGTGTAGGTCGTTCGCTCCAAGCTGGGCTG<br>TGTGCACGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAACAGGATT<br>AGCAGAGCGAGGTATGTAGGCGGTGCTACAGAGTTCTTGAAGTGGTGGCCTAACTACGG<br>CTACACTAGAAGAACAGTATTTGGTATCTGCGCTCTGCTGAAGCCAGTTACCTTCGGAA<br>AAAGAGTTGGTAGCTCTTGATCCGGCAAACAAACCACCGCTGGTAGCGGTGGTTTTTTT<br>GTTTGCAAGCAGCAGATTACGCGCAGAAAAAAAGGATCTCAAGAAGATCCTTTGATCTT<br>TTCTACGGGGTCTGACGCTCAGTGGAACGAAAACTCACGTTAAGGGATTTTGGTCATGA<br>GATTATCAAAAAGGATCTTCACCTAGATCCTTTTAAATTAAAAATGAAGTTTTAAATCA<br>ATCTAAAGTATATATGAGTAAACTTGGTCTGACAGTTACCAATGCTTAATCAGTGAGGC<br>ACCTATCTCAGCGATCTGTCTATTTCGTTCATCCATAGTTGCCTGACTCCCCGTCGTGT<br>AGATAACTACGATACGGGAGGGCTTACCATCTGGCCCCAGTGCTGCAATGATACCGCGA<br>GAGCCACGCTCACCGGCTCCAGATTTATCAGCAATAAACCAGCCAGCCGGAAGGGCCGA<br>GCGCAGAAGTGGTCCTGCAACTTTATCCGCCTCCATCCAGTCTATTAATTGTTGCCGGG<br>AAGCTAGAGTAAGTAGTTCGCCAGTTAATAGTTTGCGCAACGTTGTTGCCATTGCTACA<br>GGCATCGTGGTGTCACGCTCGTCGTTTGGTATGGCTTCATTCAGCTCCGGTTCCCAACG<br>ATCAAGGCGAGTTACATGATCCCCCATGTTGTGCAAAAAAGCGGTTAGCTCCTTCGGTC<br>CTCCGATCGTTGTCAGAAGTAAGTTGGCCGCAGTGTTATCACTCATGGTTATGGCAGCA<br>CTGCATAATTCTCTTACTGTCATGCCATCCGTAAGATGCTTTTCTGTGACTGGTGAGTA<br>CTCAACCAAGTCATTCTGAGAATAGTGTATGCGGCGACCGAGTTGCTCTTGCCCGGCGT<br>CAATACGGGATAATACCGCGCCACATAGCAGAACTTTAAAAGTGCTCATCATTGGAAAA<br>CGTTCTTCGGGGCGAAAACTCTCAAGGATCTTACCGCTGTTGAGATCCAGTTCGATGTA<br>ACCCACTCGTGCACCCAACTGATCTTCAGCATCTTTTACTTTCACCAGCGTTTCTGGGT<br>GAGCAAAAACAGGAAGGCAAAATGCCGCAAAAAAGGGAATAAGGGCGACACGGAAATGT<br>TGAATACTCATACTCTTCCTTTTTCAATATTATTGAAGCATTTATCAGGGTTATTGTCT<br>CATGAGCGGATACATATTTGAATGTATTTAGAAAAATAAACAAATAGGGGTTCCGCGCA<br>CATTTCCCCGAAAAGTGCCACCTGACGTCTAAGAAACCATTATTATCATGACATTAACC<br>TATAAAAATAGGCGTATCACGAG |
| 11 | GGTTCCGCTTCCTCGCTCACTGACTCGCTGCGCTCGGTCGTTCGGCTGCGGCGAGCGGT<br>ATCAGCTCACTCAAAGGCGGTAATACGGTTATCCACAGAATCAGGGGATAACGCAGGAA<br>AGAACATGTGAGCAAAAGGCCAGCAAAAGGCCAGGAACCGTAAAAAGGCCGCGTTGCTG<br>GCGTTTTTCCATAGGCTCCGCCCCCCTGACGAGCATCACAAAAATCGACGCTCAAGTCA<br>GAGGTGGCGAAACCCGACAGGACTATAAAGATACCAGGCGTTTCCCCCTGGAAGCTCCC<br>TCGTGCGCTCTCCTGTTCCGACCCTGCCGCTTACCGGATACCTGTCCGCCTTTCTCCCT<br>TCGGGAAGCGTGGCGCTTTCTCATAGCTCACGCTGTAGGTATCTCAGTTCGGTGTAGGT<br>CGTTCGCTCCAAGCTGGGCTGTGTGCACGAACCCCCCGTTCAGCCCGACCGCTGCGCCT<br>TATCCGGTAACTATCGTCTTGAGTCCAACCCGGTAAGACACGACTTATCGCCACTGGCA<br>GCAGCCACTGGTAACAGGATTAGCAGAGCGAGGTATGTAGGCGGTGCTACAGAGTTCTT<br>GAAGTGGTGGCCTAACTACGGCTACACTAGAAGGACAGTATTTGGTATCTGCGCTCTGC<br>TGAAGCCAGTTACCTTCGGAAAAAGAGTTGGTAGCTCTTGATCCGGCAAACAAACCACC<br>GCTGGTAGCGGTGGTTTTTTTGTTTGCAAGCAGCAGATTACGCGCAGAAAAAAAGGATC<br>TCAAGAAGATCCTTTGATCTTTTCTACGGGGTCTGACGCTCAGTGGAACGAAAACTCAC<br>GTTAAGGGATTTTGGTCATGAGATTATCAAAAAGGATCTTCACCTAGATCCTTTTAAAT<br>TAAAAATGAAGTTTTAAATCAATCTAAAGTATATATGAGTAAACTTGGTCTGACAGTTA<br>CCAATGCTTAATCAGTGAGGCACCTATCTCAGCGATCTGTCTATTTCGTTCATCCATAG<br>TTGCCTGACTCCCCGTCGTGTAGATAACTACGATACGGGAGGGCTTACCATCTGGCCCC<br>AGTGCTGCAATGATACCGCGAGACCCACGCTCACCGGCTCCAGATTTATCAGCAATAAA<br>CCAGCCAGCCGGAAGGGCCGAGCGCAGAAGTGGTCCTGCAACTTTATCCGCCTCCATCC<br>AGTCTATTAATTGTTGCCGGGAAGCTAGAGTAAGTAGTTCGCCAGTTAATAGTTTGCGC<br>AACGTTGTTGCCATTGCTGCAGGCATCGTGGTGTCACGCTCGTCGTTTGGTATGGCTTC<br>ATTCAGCTCCGGTTCCCAACGATCAAGGCGAGTTACATGATCCCCCATGTTGTGCAAAA<br>AAGCGGTTAGCTCCTTCGGTCCTCCGATCGTTGTCAGAAGTAAGTTGGCCGCAGTGTTA<br>TCACTCATGGTTATGGCAGCACTGCATAATTCTCTTACTGTCATGCCATCCGTAAGATG<br>CTTTTCTGTGACTGGTGAGTACTCAACCAAGTCATTCTGAGAATAGTGTATGCGGCGAC<br>CGAGTTGCTCTTGCCCGGCGTCAACACGGGATAATACCGCGCCACATAGCAGAACTTTA<br>AAAGTGCTCATCATTGGAAAACGTTCTTCGGGGCGAAAACTCTCAAGGATCTTACCGCT<br>GTTGAGATCCAGTTCGATGTAACCCACTCGTGCACCCAACTGATCTTCAGCATCTTTTA<br>CTTTCACCAGCGTTTCTGGGTGAGCAAAAACAGGAAGGCAAAATGCCGCAAAAAAGGGA<br>ATAAGGGCGACACGGAAATGTTGAATACTCATACTCTTCCTTTTTCAATATTATTGAAG<br>CATTTATCAGGGTTATTGTCTCATGAGCGGATACATATTTGAATGTATTTAGAAAAATA<br>AACAAATAGGGGTTCCGCGCACATTTCCCCGAAAAGTGCCACCTGACGTCTAAGAAACC |

TABLE 11-continued

| sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text. | |
|---|---|
| SEQ ID NO: | sequence 5' to 3' |
| | ATTATTATCATGACATTAACCTATAAAAATAGGCGTATCACGAGGCCCTTTCGTCTGGC<br>CTAGGAAGCGACTTCCAATCGCTTTGCATATCCAGTACCACACCCACAGGCGTTTGTGC<br>TACTCTACTGATAGCAATAGATGCGTCATAATTGGTTGGCCCGCTGAGCCTCCACAGGA<br>TACTATTGCACATACCCTGGTCATGTGCAGATCAGCTCATTTGTGGAGACTCTGGAGTA<br>ACTTAGACGACGCCTGGTTCAATTGCCGCAATGTGCGCCCACGCAGATAATGTATTGAG<br>GGGTGGAGCGCCTCTTGGGGACTTGCTGTACTTGTACGGGATATTAAACGCACTCAGCA<br>AGACCATGACGTAAAACACACCTACTGTACGATACGTACTGTAGGTATTGTACTCGTAC<br>CCGGTACTACAAATAGTACGATACTATACGGAGTGTATTTGTACCTTGATATACGACTG<br>GCGGAGTGAAGAGAAGGAGTTGAACAAGACCAGATGGGGATATCAGCCCCAGTGCTTTG<br>TATTACAAGTACGAGTACTTAATAGATACTGTAAGGCTATTGATACGGATGGCAGTAAG<br>TCATTGAGTAAGCAATTGTGGCCCAGCATCTCCCCTACGTACTTGTACCATACCCCATG<br>GAGACACCAATGGTCTTTCACGCACACTGTCGTGTGCTGTATCGCAGAATCGGGTGTCC<br>AACCAAATGCCGTTACCCCCACGTCACAGCCGATAGACAGATACACCATCAATACCAGC<br>AGGTTGTATCATGCGGTTGGCTGAAGGTAAGCTGATTGGTCTAAAAACTGTAGCTGTCC<br>TAATTCAACGAGCGCTATTTGGGGCCAACCACCTCGGCCAAGCGGCCTTTAATCTGCGT<br>GCCCCAGAGGCGTCTAATGAGGCTCTGGCCGCCACTGTAGGAGTGTTTCTCTGTGCGCA<br>CACGCAGTTTTGAGTTTGGGCGACTTTCCCTTTTTCCCAATTGCGTACACACACAGCTC<br>CGAGCTAAGCGCTGTCCTTGAACCTTCTCCCTCTTTTCCCTCTTTTTCTCTTCCCCTTC<br>CCCTCCTCCACATTAAGGCCAAATCCTGAATTGCACCAACTAGTACAACGACAACAATG<br>GACAAGAAGTACTCCATCGGTTTGGACATTGGTACTAACTCTGTCGGCTGGGCCGTCAT<br>CACCGACGAGTACAAGGTTCCCTCCAAGAAGTTCAAGGTCCTTGGCAACACCGACCGAC<br>ACTCTATCAAGAAGAACCTGATCGGTGCTCTGCTGTTCGACTCTGGCGAGACTGCCGAG<br>GCCACCCGACTGAAGCGAACCGCTCGACGCCGATACACCCGACGAAAGAACCGAATCTG<br>TTACCTCCAGGAGATCTTCAGCAACGAGATGGCTAAGGTCGACGACTCCTTCTTCCACC<br>GACTCGAGGAGTCTTTCCTGGTCGAAGAGGATAAGAAGCACGAGCGACACCCCATCTTC<br>GGCAACATTGTTGATGAGGTTGCCTACCATGAGAAGTACCCCACCATCTACCACCTCCG<br>AAAGAAGCTCGTCGACTCCACTGACAAGGCTGACCTCCGACTCATCTACCTTGCTCTCG<br>CCCACATGATCAAGTTCCGAGGTCACTTCCTCATTGAGGGTGATCTCAACCCCGACAAC<br>TCCGACGTTGACAAGCTGTTCATCCAGCTCGTCCAGACCTACAACCAGCTCTTTGAGGA<br>GAACCCTATCAACGCTTCTGGTGTTGACGCCAAGGCCATTCTCTCCGCCCGACTCTCTA<br>AGTCCCGACGACTCGAGAACCTCATTGCCCAGCTGCCCGGCGAGAAGAAGAACGGCCTC<br>TTCGGTAACCTGATTGCTCTCTCTCTTGGTCTGACCCCCAACTTCAAGTCCAACTTTGA<br>CCTCGCCGAGGACGCCAAGCTCCAGCTGTCCAAGGACACCTACGATGACGATCTGGACA<br>ACCTCCTGGCCCAGATCGGTGACCAGTACGCCGATCTCTTCCTTGCCGCCAAGAACCTC<br>TCCGACGCCATCCTGCTCTCCGACATCCTCCGAGTCAACACCGAGATTACCAAGGCTCC<br>TCTGTCTGCCTCTATGATCAAGCGATACGACGAGCACCACCAGGATCTCACTCTTCTCA<br>AGGCTCTCGTCCGACAGCAGCTCCCCGAGAAGTACAAGGAGATTTTCTTTGACCAGTCC<br>AAGAACGGTTACGCTGGCTACATTGACGGTGGTGCTTCCCAGGAAGAGTTTTACAAGTT<br>CATCAAGCCTATTCTGGAGAAGATGGACGGTACCGAGGAGCTGCTCGTCAAGCTCAACC<br>GAGAGGACCTCCTTCGAAAGCAGCGAACCTTCGATAACGGCTCCATCCCCCACCAGATC<br>CACCTGGGTGAGCTCCACGCCATTCTCCGAAGACAAGAGGACTTCTACCCCTTCCTAAA<br>GGATAACCGAGAGAAGATCGAGAAGATTCTCACCTTCCGAATCCCCTACTACGTCGGTC<br>CCCTCGCTCGAGGTAACTCCCGATTTGCTTGGATGACCCGAAAGTCCGAGGAGACTATC<br>ACCCCCTGGAACTTTGAAGAGGTAGTCGACAAGGGTGCCTCCGCCCAGTCTTTCATTGA<br>GCGGATGACCAACTTCGATAAGAACCTCCCCAACGAGAAGGTCCTTCCCAAGCACTCTC<br>TCCTCTACGAGTACTTCACCGTCTACAACGAGCTGACCAAGGTCAAGTACGTTACCGAG<br>GGCATGCGAAAGCCCGCTTTCCTCTCTGGTGAGCAGAAGAAGGCCATTGTCGACCTCCT<br>GTTCAAGACTAACCGAAAAGTCACCGTCAAGCAGCTCAAGGAAGACTACTTCAAGAAGA<br>TTGAGTGCTTCGACTCCGTCGAGATTTCCGGTGTCGAGGACCGATTCAACGCCTCCCTC<br>GGCACCTACCACGATCTTCTGAAGATCATCAAGGACAAGGACTTTCTTGATAACGAGGA<br>GAACGAGGACATTCTCGAGGACATCGTCCTCACCCTCACCCTTTTCGAGGATCGAGAGA<br>TGATCGAGGAGCGACTCAAGACCTACGCCCATCTCTTCGACGACAAGGTCATGAAGCAA<br>CTCAAGCGACGACGATACACTGGCTGGGGCCGACTTTCCCGAAAGCTCATCAACGGCAT<br>CCGAGACAAGCAGTCTGGCAAGACCATCCTGGACTTCCTGAAGTCCGACGGTTTCGCCA<br>ACCGAAACTTCATGCAGCTCATCCACGACGACTCTCTTACCTTCAAAGAGGATATCCAG<br>AAGGCCCAGGTTTCTGGCCAGGGCGACTCCCTCCACGAGCACATTGCCAACCTCGCCGG<br>ATCCCCCGCCATCAAAAAGGGTATCCTCCAGACCGTCAAGGTTGTCGACGAACTCGTGA<br>AGGTCATGGGCCGACACAAGCCCGAGAACATCGTTATCGAGATGGCCCGAGAGAACCAG<br>ACCACCCAGAAGGGTCAGAAGAACTCCCGAGAGCGAATGAAGCGAATCGAAGAGGGTAT<br>CAAGGAGCTCGGTTCCCAGATTCTCAAGGAGCACCCCGTCGAGAACACCCAGCTCCAGA<br>ACGAGAAACTCTACCTGTACTACCTCCAGAATGGCCGAGACATGTACGTTGACCAGGAG<br>CTCGACATCAACCGACTCTCCGACTACGACGTCGACCACATTGTTCCTCAGTCCTTCCT<br>CAAGGACGACTCCATCGACAACAAGGTTCTGACCCGATCTGACAAGAACCGAGGTAAGT<br>CCGACAACGTTCCCTCCGAAGAGGTCGTTAAGAAGATGAAGAACTACTGGCGACAGCTT<br>CTCAACGCCAAACTGATCACCCAGCGAAAGTTTGACAACCTCACCAAGGCCGAGCGAGG<br>TGGTCTGTCCGAGCTGGACAAGGCCGGCTTCATTAAGCGACAGCTGGTCGAGACTCGAC<br>AGATCACCAAGCACGTCGCCCAGATCCTCGACTCCCGAATGAACACCAAGTACGACGAG<br>AACGACAAGCTCATCCGGGAGGTCAAGGTCATCACCCTGAAGTCTAAGCTTGTCTCCGA<br>CTTCCGAAAGGACTTCCAGTTCTACAAGGTCCGAGAGATCAACAACTACCACCACGCCC<br>ACGACGCCTACCTCAACGCCGTTGTTGGTACCGCCCTCATCAAGAAGTATCCCAAGCTC<br>GAGTCCGAGTTCGTTTACGGCGACTACAAGGTTTACGATGTCCGAAAGATGATTGCCAA<br>GTCCGAGCAGGAGATCGGTAAGGCCACCGCCAAGTACTTTTTCTACTCCAACATCATGA |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | ATTTCTTCAAGACCGAGATCACTCTCGCCAACGGTGAGATTCGAAAGCGACCCCTGATT |
| | GAGACTAATGGTGAGACTGGTGAGATCGTCTGGGATAAGGGCCGAGACTTCGCCACCGT |
| | CCGAAAGGTCCTGTCCATGCCCCAGGTCAACATTGTCAAGAAGACCGAGGTCCAGACCG |
| | GTGGCTTCTCCAAGGAGTCCATTCTCCCCAAGCGAAACTCCGACAAACTCATCGCCCGT |
| | AAGAAGGACTGGGATCCGAAGAAGTACGGTGGTTTCGATTCTCCCACCGTTGCCTACTC |
| | CGTCCTCGTTGTTGCTAAAGTCGAGAAGGGTAAGTCTAAGAAACTCAAGTCCGTGAAGG |
| | AGCTACTCGGTATCACCATCATGGAGCGATCTTCTTTTGAGAAGAACCCCATTGACTTC |
| | CTCGAGGCCAAGGGTTACAAAGAGGTCAAGAAGGACCTGATTATCAAGCTGCCCAAGTA |
| | CTCCCTCTTTGAGCTCGAGAACGGCCGAAAGCGAATGCTGGCTTCCGCTGGTGAGCTGC |
| | AGAAGGGCAACGAGCTCGCTCTGCCCTCCAAGTACGTCAACTTCCTCTACCTGGCCTCC |
| | CACTACGAGAAGCTCAAGGGCTCCCCCGAGGACAACGAGCAGAAGCAGCTGTTCGTTGA |
| | GCAGCACAAGCACTACCTCGACGAGATCATCGAGCAGATCTCCGAGTTCTCCAAGCGAG |
| | TCATCCTCGCTGACGCCAACCTTGATAAGGTTCTCTCTGCTTACAACAAGCACCGGGAC |
| | AAGCCCATCCGAGAGCAGGCCGAGAATATCATCCACCTCTTCACTCTCACCAACCTCGG |
| | CGCTCCTGCTGCCTTCAAGTACTTCGACACCACCATTGACCGAAAGAGGTACACCTCCA |
| | CCAAGGAAGTCCTCGACGCCACCCTGATCCACCAGTCCATCACCGGCCTCTACGAAACC |
| | CGAATCGACCTCTCCCAGCTCGGCGGTGACTCTCGAGCCGACCCCAAGAAGAAGCGAAA |
| | AGTCTAAATATCCGAAGATCAAGAGCGAAGCAAGTTGTAAGTCCAGGACATGTTTCCCG |
| | CCCACGCGAGTGATTTATAACACCTCTCTTTTTTGACACCCGCTCGCCTTGAAATTCAT |
| | GTCACATAAATTATAGTCAACGACGTTTGAATAACTTGTCTTGTAGTTCGATGATGATC |
| | ATATGATTACATTAATAGTAATTACTGTATTTGATATATATACTAATTACAATAGTACA |
| | TATTAGAACATACAATAGTTAGTGCCGTGAAGTGGCTTAAAATACCGCGAGTCGATTAC |
| | GTAATATTATTACCTCTTGCCCATCGAACGTACAAGTACTCCTCTGTTCTCTCCTTCCT |
| | TTGCTTTGTGCACGAAGAACTGCGGTCAGGTGACACAACTTTTTCCATCTCAGGGTGTG |
| | TCGCGTGTGCTTCATCCAAACTTTAGTTGGGGTTCGGGTTCGCGCGAGATGATCACGTG |
| | CCCTGATTTGGTGTCGTCCCCCGTCGCGCTGCGCACGTGATTTATTTATTTCCGGTGGC |
| | TGCTGTCTACGCGGGGCCTTCTCTGCCCTTCTGTTTCAACCTTCGGGCGGTTCTCGTAA |
| | CCAGCAGTAGCAATCCATTTCGAAACTCAAAGAGCTAAAAACGTTAAACCTCAGCAGTC |
| | GCTCGACGAATGGGCTGCGGTTGGGAAGCCCACGAGGCCTATAGCCAGAGCCTCGAGTT |
| | GACAGGAGCCCAGACGCCTTTTCCAACGGCAACTTTTATATAAAATGGCAATGTATTCA |
| | TGCAATTGCGGCCGTGTCAGGTTGGAGACACTGGACCACACTCTCCATTGCTTCCTGAG |
| | GAGATGGATCATTGCTAGTGCATCTACGCGCAGCAATCCCGCAAGCTCGACAACCGTAG |
| | ATGGGCTTTGGTGGGCCAATCAATTACGCAACCCGCACGTTAAATTGTATGAGGAAGGA |
| | AGGCCACGGTACAAAGTGGGTGGTCTTCACCCAGTGGTTGTTGGTGGCGTCATGCAGAC |
| | CATGCATTGGGGATAGCACAGGGTTGGGGTGTCTTGTGGACTCAATGGGTGAAAGGAGA |
| | TGGAAAAGGGCGGTGAAAAGTGGTAGAATCGAAATCCCTGACGTCAATTTATAAAGTAA |
| | AATGCGTTTCTGCCATTTTGCTCCCCTCCTTCTTTCGCAATCGCCTCCCCAAAAGTTGT |
| | CGTGGCAGTACACATGCTTGCATACAATGAAGCTAATCCGGCTTGCTCAGTAGTTGCTA |
| | TATCCAGGCATGGTGTGAAACCCCTCAAAGTATATATAGGAGCGGTGAGCCCCAGTCTG |
| | GGGTCTTTTCTCTCCATCTCAAAACTACTTTCTCACAATGGATTTGCTGATGAGTCCGT |
| | GAGGACGAAACGAGTAAGCTCGTCTGGAGGCATGATCAACAGCGGTTTTAGAGCTAGAA |
| | ATAGCAAGTTAAAATAAGGCTAGTCCGTTATCAACTTGAAAAAGTGGCACCGAGTCGGT |
| | GCTTTTGGCCGGCATGGTCCCAGCCTCCTCGCTGGCGCCGGCTGGGCAACATGCTTCGG |
| | CATGGCGAATGGGACTAAACTTCGAGCTAATCCAGTAGCTTACGTTACCCAGGGGCAGG |
| | TCAACTGGCTAGCCACGAGTCTGTCCCAGGTCGCAATTTAGTGTAATAAACAATATATA |
| | TATTGAGTCTAAAGGGAATTGTAGCTATTGTGATTGTGTGATTTTCGTCTTGCTGGTTC |
| | TTATTGTGTCCCATTCGTTTCATCCTGATGAGGACCCCTGGAACCGGTGTTTTCTTAGT |
| | CTCTGCAATCGCTAGTCTTGTTGCTATGACAGTTGCGTCGACACTATTCAGGTCATCTA |
| | TCGGTTATTCTGATATTATAATACCTCCGGATCGATGTACCTGATTTATACTTGCAGCA |
| | ATGTTTACTTCTTATCGTTGGACCCCGTCTTCAATTACACTTCCCAACTGGGAACACCC |
| | CTCTTTATCGACCCATTTTAGGTAATTTACCCTAGCCCATTGTCTCCATAAGGAATATT |
| | ACCCTAACCCACAGTCCAGGGTGCCCAGGTCCTTCTTTGGCCAAATTTTAACTTCGGTC |
| | CTATGGCACAGCGGTAGCGCGTGAGATTGCAAATCTTAAGGTCCCGAGTTCGAATCTCG |
| | GTGGGACCTAGTTGAAAAATACCTCTAATGCGCCGATGGTTTAGTGGTAAAATCCATCG |
| | TTGCCATCGATGGGCCCCCGGTTCGATTCCGGGTCGGCGCAGGTTGACGTACAGCAGGC |
| | TGAACGAGGATGTTTTAGAGCTAGAAATAGCAAGTTAAAATAAGGCTAGTCCGTTATCA |
| | ACTTGAAAAAGTGGCACCGAGTCGGTGCTTTTTTTTTTCGATCGGCCCCAGTTGCAAAA |
| | GTTGACACAACTCTAGATCTGCTTCCAAATATAGAATCATAACAAGGGTTAGGGTGTGA |
| | TTATATAATATTGGTCTTAATTGATGTGCTAGGGCTTTAAAAGTTGGTTAAAATAACGC |
| | TCTAATGCCTTTTTAATATATTGTCTTTTTCAAAATCTCAAATCGGACACTTCTTCGTG |
| | TATGAGACTCCATTTTTTGGCTCCGTCACGTGATATGTATTATCAGCTATAGTGGTGTA |
| | AACAAAGTTTTTTACTAGCTGTAATGGCATTTTGTCGGAGTGGTAAATCGCCTTCTTGT |
| | TGTGCGTTCGAGTTCTGGACTCTGCACTGGGCTACTTTGAAAAATACCTCTAATGCGCC |
| | GATGGTTTAGTGGTAAAATCCATCGTTGCCATCGATGGGCCCCCGGTTCGATTCCGGGT |
| | CGGCGCAGGTTGACGTTCACTCCTCAGCCTCCCAAGGTTTTAGAGCTAGAAATAGCAAG |
| | TTAAAATAAGGCTAGTCCGTTATCAACTTGAAAAAGTGGCACCGAGTCGGTGCTTTTTT |
| | TTTTCGCGATACACGAATGTGATACGGATCAAAGTAAGCAGGACTACGATAAGATAACG |
| | AATGCGGTGCAGTCCATGTCGATTAGGTATAGATACATTTATTTTGTGTTATGTTACAT |
| | TTTGGGGGGATACTGTCCTACTTGTAGTACCTACTTGTAGTGGCGCGTCTATTCCTTTG |
| | CCCTCGGACGAGTGCTGGGGCGTCGGTTTCCACTATCGGCGAGTACTTCTACACAGCCA |
| | TCGGTCCAGACGGCCGCGCTTCTGCGGGCGATTTGTGTACGCCCGACAGTCCCGGCTCC |
| | GGATCGGACGATTGCGTCGCATCGACCCTGCGCCCAAGCTGCATCATCGAAATTGCCGT |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
| --- | --- |
| | CAACCAAGCTCTGATAGAGTTGGTCAAGACCAATGCGGAGCATATACGCCCGGAGCCGC<br>GGCGATCCTGCAAGCTCCGGATGCCTCCGCTCGAAGTAGCGCGTCTGCTGCTCCATACA<br>AGCCAACCACGGCCTCCAGAAGAAGATGTTGGCGACCTCGTATTGGGAATCCCCGAACA<br>TCGCCTCGCTCCAGTCAATGACCGCTGTTATGCGGCCATTGTCCGTCAGGACATTGTTG<br>GAGCCGAAATCCGCGTGCACGAGGTGCCGGACTTCGGGGCAGTCCTCGGCCCAAAGCAT<br>CAGCTCATCGAGAGCCTGCGCGACGGACGCACTGACGGTGTCGTCCATCACAGTTTGCC<br>AGTGATACACATGGGGATCAGCAATCGCGCATATGAAATCACGCCATGTAGTGTATTGA<br>CCGATTCCTTGCGGTCCGAATGGGCCGAACCCGCTCGTCTGGCTAAGATCGGCCGCAGC<br>GATCGCATCCATGGCCTCCGCGACCGGCTGCAGAACAGCGGGCAGTTCGGTTTCAGGCA<br>GGTCTTGCAACGTGACACCCTGTGCACGGCGGGAGATGCAATAGGTCAGGCTCTCGCTG<br>AATTCCCCAATGTCAAGCACTTCCGGAATCGGGAGCGCGGCCGATGCAAAGTGCCGATA<br>AACATAACGATCTTTGTAGAAACCATCGGCGCAGCTATTTACCCGCAGGACATATCCAC<br>GCCCTCCTACATCGAAGCTGAAAGCACGAGATTCTTCGCCCTCCGAGAGCTGCATCAGG<br>TCGGAGACGCTGTCGAACTTTTCGATCAGAAACTTCTCGACAGACGTCGCGGTGAGTTC<br>AGGCTTTTTCATATGGGTACCTGAGAACATTTTTGTGTCTAGGTGTTTGTGTTTGGACT<br>GCGATCAGTGAAGAAAAGAAGAGGAAAAATTGTGCAAGAAATTTTGCTTTCAAGACTTG<br>GCTGATGCAGCAGGGTAACTCTGGGACACAGACCTATGTTTGTGGTTAAACTCAATGCA<br>CGTGGTACGTGCGTGGAGCGCTTACCCATCCAAGGGTGTGGACATGGAACCGACGGTCC<br>GTGGAGTTGTGTAATGTCATTTTGGCGACTCTTGAAGCAAGGCTATAAAAAAATTGTGT<br>GGCTTGAGTCTTATCGAGCTCGGTCACTACAAGAGTTAATCTTCCTGTCTCAGGCAGAC<br>AGGTCAGGCAGGGTTACTTTTGGGTGTGCTGTAACTCACTGTATGGCCGTTAGTGCGCA<br>TAGACGTTGTACATACTGGACCGAATTGTAGCGTGCTCAATAGGGCCAATAAAGCTATT<br>GTAGGGATCCGAATTTTCAGAACCTAATTTATCTGTTACCCGGCCTGTGGCTCGCACAG<br>CTTAAAAATGGTCAAACTTTCCCCTTCTTGTCTTTTTTTCCTCACATTCATCAGGTTCT<br>TGTCTTGATCTTTCAAGTGAGTATTAATTACCGACCTTGGTTCTTCATTGGGAGAGCAT<br>TGGAAGCCGTGGTGCAGCAACCACAAAACGGTTCTTCCCCTTCGATACCTTCTTGCCTG<br>CCTTTCAATACAAGTCGGCTCGATTAGCGGTGGTCGCCCCCGCCAGCGGAGAACATGGA<br>ACTAACCCAGAATGAGAGCTAAGTGGAGAAAGAAGAGAGTCAGACGACTCAAGCGAAAG<br>CGCCGCAAGGTCCGAGCTCGATCCAAATAAGCGGTTTTTAACGGAGATTTAACACTAAA<br>TCGAAGAACTTTTCCCGTTTCATTTGCGAATGAGCTCGTTAACAAAATCCCCCAGTTTT<br>TTTATCCAGCTGTAAGGATTGACATTAGTAATGAATTATTGTTTGGTATATTTAAATCT<br>GTAGTTCCTTTCTGTCCGTGTCGGCAACTGTCGTACTCGTGATTTACTTGTATTGACGA<br>ATACTTACTGTAGCGCACTCTGCTGCTACTGGTCGTAAGGATGTGCTATTTCGGTGTAT<br>GGTGGGTTTTTTGGGGGTCGGAACCGAAGACTGTTACACGGGCACGGCTCGTTGTGTAC<br>ACGCACAGAGCTCTTGCGAGTCATGTTGTAGCTAGCTCGTCGTGTTCAGGAACTGTTCG<br>ATGGTTCGGAGAGAGTCGCCGCCCAGAACATACGCGCACCGATGTCAGCAGACAGCCTT<br>ATTACAAGTATATTCAAGCAAGTATATCCGTAGGGTGCGGGTGATTTGGATCTAAGGTT<br>CGTACTCAACACTCACGAGCAGCTTGCCTATGTTACATCCTTTTATCAGACATAACATA<br>ATTGGAGTTTACTTACACACGGGGTGTACCTGTATGAGCACCACCTACAATTGTAGCAC<br>TGGTACTTGTACAAAGAATTTATTCGTACGAATCACAGGGACGGCCGCCCTCACCGAAC<br>CAGCGAATACCTCAGCGGTCCCCTGCAGTGACTCAACAAAGCGATATGAACATCTTGCG<br>ATGGTATCCTGCTGATAGTTTTTACTGTACAAACACCTGTGTAGCTCCTTCTAGCATTT<br>TTAAGTTATTCACACCTCAAGGGGAGGGATAAATTAAATAAATTCCAAAAGCGAAGATC<br>GAGAAACTAAATTAAAATTCCAAAAACGAAGTTGGAACACAACCCCCCGAAAAAAAACA<br>ACAAACAAAAAACCCAACAAAATAAACAAAAACAAAATAAATATATAACTACCAGTATC<br>TGACTAAAAGTTCAAATACTCGTACTTACAACAAATAGAAATGAGCCGGCCAAAATTCT<br>GCAGAAAAAAATTTCAAACAAGTACTGGTATAATTAAATTAAAAAACACATCAAAGTAT<br>CATAACGTTAGTTATTTTATTTTATTTAATAAAAGAAAACAACAAGATGGGCTCAAAAC<br>TTTCAACTTATACGATACATACCAAATAACAATTTAGTATTTATCTAAGTGCTTTTCGT<br>AGATAATGGAATACAAATGGATATCCAGAGTATACACATGGATAGTATACACTGACACG<br>ACAATTCTGTATCTCTTTATGTTAACTACTGTGAGGCATTAAATAGAGCTTGATATATA<br>AAATGTTACATTTCACAGTCTGAACTTTTGCAGATTACCTAATTTGGTAAGATATTAAT<br>TATGAACTGAAAGTTGATGGCATCCCTAAATTTGATGAAAGATGAAATTGTAAATGAGG<br>TGGTAAAAGAGCTACAGTCGTTTTGTTTTGAGATACCATCATCTCTAACGAAATATCTA<br>TTAAAAATCTCAGTGTGATCATGAGTCATTGCCATCCTGGAAAATGTCATCATGGCTGA<br>TATTTCTAACTGTTTACTTGAGATAAATATATATTTACAAGAACTTCCCTTGAAATTAA<br>TTTAGATATAAAATGTTTGCGGGCAAGTTACTACGAGGAATAAATTATATCTAGA |
| 12 | GGTTCCGCTTCCTCGCTCACTGACTCGCTGCGCTCGGTCGTTCGGCTGCGGCGAGCGGT<br>ATCAGCTCACTCAAAGGCGGTAATACGGTTATCCACAGAATCAGGGGATAACGCAGGAA<br>AGAACATGTGAGCAAAAGGCCAGCAAAAGGCCAGGAACCGTAAAAAGGCCGCGTTGCTG<br>GCGTTTTTCCATAGGCTCCGCCCCCCTGACGAGCATCACAAAAATCGACGCTCAAGTCA<br>GAGGTGGCGAAACCCGACAGGACTATAAAGATACCAGGCGTTTCCCCCTGGAAGCTCCC<br>TCGTGCGCTCTCCTGTTCCGACCCTGCCGCTTACCGGATACCTGTCCGCCTTTCTCCCT<br>TCGGGAAGCGTGGCGCTTTCTCATAGCTCACGCTGTAGGTATCTCAGTTCGGTGTAGGT<br>CGTTCGCTCCAAGCTGGGCTGTGTGCACGAACCCCCCGTTCAGCCCGACCGCTGCGCCT<br>TATCCGGTAACTATCGTCTTGAGTCCAACCCGGTAAGACACGACTTATCGCCACTGGCA<br>GCAGCCACTGGTAACAGGATTAGCAGAGCGAGGTATGTAGGCGGTGCTACAGAGTTCTT<br>GAAGTGGTGGCCTAACTACGGCTACACTAGAAGGACAGTATTTGGTATCTGCGCTCTGC<br>TGAAGCCAGTTACCTTCGGAAAAAGAGTTGGTAGCTCTTGATCCGGCAAACAAACCACC<br>GCTGGTAGCGGTGGTTTTTTTGTTTGCAAGCAGCAGATTACGCGCAGAAAAAAAGGATC<br>TCAAGAAGATCCTTTGATCTTTTCTACGGGGTCTGACGCTCAGTGGAACGAAAACTCAC |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | GTTAAGGGATTTTGGTCATGAGATTATCAAAAAGGATCTTCACCTAGATCCTTTTAAAT |
| | TAAAAATGAAGTTTTAAATCAATCTAAAGTATATATGAGTAAACTTGGTCTGACAGTTA |
| | CCAATGCTTAATCAGTGAGGCACCTATCTCAGCGATCTGTCTATTTCGTTCATCCATAG |
| | TTGCCTGACTCCCCGTCGTGTAGATAACTACGATACGGGAGGGCTTACCATCTGGCCCC |
| | AGTGCTGCAATGATACCGCGAGACCCACGCTCACCGGCTCCAGATTTATCAGCAATAAA |
| | CCAGCCAGCCGGAAGGGCCGAGCGCAGAAGTGGTCCTGCAACTTTATCCGCCTCCATCC |
| | AGTCTATTAATTGTTGCCGGGAAGCTAGAGTAAGTAGTTCGCCAGTTAATAGTTTGCGC |
| | AACGTTGTTGCCATTGCTGCAGGCATCGTGGTGTCACGCTCGTCGTTTGGTATGGCTTC |
| | ATTCAGCTCCGGTTCCCAACGATCAAGGCGAGTTACATGATCCCCCATGTTGTGCAAAA |
| | AAGCGGTTAGCTCCTTCGGTCCTCCGATCGTTGTCAGAAGTAAGTTGGCCGCAGTGTTA |
| | TCACTCATGGTTATGGCAGCACTGCATAATTCTCTTACTGTCATGCCATCCGTAAGATG |
| | CTTTTCTGTGACTGGTGAGTACTCAACCAAGTCATTCTGAGAATAGTGTATGCGGCGAC |
| | CGAGTTGCTCTTGCCCGGCGTCAACACGGGATAATACCGCGCCACATAGCAGAACTTTA |
| | AAAGTGCTCATCATTGGAAAACGTTCTTCGGGGCGAAAACTCTCAAGGATCTTACCGCT |
| | GTTGAGATCCAGTTCGATGTAACCCACTCGTGCACCCAACTGATCTTCAGCATCTTTTA |
| | CTTTCACCAGCGTTTCTGGGTGAGCAAAAACAGGAAGGCAAAATGCCGCAAAAAAGGGA |
| | ATAAGGGCGACACGGAAATGTTGAATACTCATACTCTTCCTTTTTCAATATTATTGAAG |
| | CATTTATCAGGGTTATTGTCTCATGAGCGGATACATATTTGAATGTATTTAGAAAAATA |
| | AACAAATAGGGGTTCCGCGCACATTTCCCCGAAAAGTGCCACCTGACGTCTAAGAAACC |
| | ATTATTATCATGACATTAACCTATAAAAATAGGCGTATCACGAGGCCCTTTCGTCTGGC |
| | CTAGGAAGCGACTTCCAATCGCTTTGCATATCCAGTACCACACCCACAGGCGTTTGTGC |
| | TACTCTACTGATAGCAATAGATGCGTCATAATTGGTTGGCCCGCTGAGCCTCCACAGGA |
| | TACTATTGCACATACCCTGGTCATGTGCAGATCAGCTCATTTGTGGAGACTCTGGAGTA |
| | ACTTAGACGACGCCTGGTTCAATTGCCGCAATGTGCGCCCACGCAGATAATGTATTGAG |
| | GGGTGGAGCGCCTCTTGGGGACTTGCTGTACTTGTACGGGATATTAAACGCACTCAGCA |
| | AGACCATGACGTAAAACACACCTACTGTACGATACGTACTGTAGGTATTGTACTCGTAC |
| | CCGGTACTACAAATAGTACGATACTATACGGAGTGTATTTGTACCTTGATATACGACTG |
| | GCGGAGTGAAGAGAAGGAGTTGAACAAGACCAGATGGGGATATCAGCCCCAGTGCTTTG |
| | TATTACAAGTACGAGTACTTAATAGATACTGTAAGGCTATTGATACGGATGGCAGTAAG |
| | TCATTGAGTAAGCAATTGTGGCCCAGCATCTCCCCTACGTACTTGTACCATACCCCATG |
| | GAGACACCAATGGTCTTTCACGCACACTGTCGTGTGCTGTATCGCAGAATCGGGTGTCC |
| | AACCAAATGCCGTTACCCCCACGTCACAGCCGATAGACAGATACACCATCAATACCAGC |
| | AGGTTGTATCATGCGGTTGGCTGAAGGTAAGCTGATTGGTCTAAAAACTGTAGCTGTCC |
| | TAATTCAACGAGCGCTATTTGGGGCCAACCACCTCGGCCAAGCGGCCTTTAATCTGCGT |
| | GCCCCAGAGGCGTCTAATGAGGCTCTGGCCGCCACTGTAGGAGTGTTTCTCTGTGCGCA |
| | CACGCAGTTTTGAGTTTGGGCGACTTTCCCTTTTTCCCAATTGCGTACACACACAGCTC |
| | CGAGCTAAGCGCTGTCCTTGAACCTTCTCCCTCTTTTCCCTCTTTTTCTCTTCCCCTTC |
| | CCCTCCTCCACATTAAGGCCAAATCCTGAATTGCACCAACTAGTACAACGACAACAATG |
| | GACAAGAAGTACTCCATCGGTTTGGACATTGGTACTAACTCTGTCGGCTGGGCCGTCAT |
| | CACCGACGAGTACAAGGTTCCCTCCAAGAAGTTCAAGGTCCTTGGCAACACCGACCGAC |
| | ACTCTATCAAGAAGAACCTGATCGGTGCTCTGCTGTTCGACTCTGGCGAGACTGCCGAG |
| | GCCACCCGACTGAAGCGAACCGCTCGACGCCGATACACCCGACGAAAGAACCGAATCTG |
| | TTACCTCCAGGAGATCTTCAGCAACGAGATGGCTAAGGTCGACGACTCCTTCTTCCACC |
| | GACTCGAGGAGTCTTTCCTGGTCGAAGAGGATAAGAAGCACGAGCGACACCCCATCTTC |
| | GGCAACATTGTTGATGAGGTTGCCTACCATGAGAAGTACCCCACCATCTACCACCTCCG |
| | AAAGAAGCTCGTCGACTCCACTGACAAGGCTGACCTCCGACTCATCTACCTTGCTCTCG |
| | CCCACATGATCAAGTTCCGAGGTCACTTCCTCATTGAGGGTGATCTCAACCCCGACAAC |
| | TCCGACGTTGACAAGCTGTTCATCCAGCTCGTCCAGACCTACAACCAGCTCTTTGAGGA |
| | GAACCCTATCAACGCTTCTGGTGTTGACGCCAAGGCCATTCTCTCCGCCCGACTCTCTA |
| | AGTCCCGACGACTCGAGAACCTCATTGCCCAGCTGCCCGGCGAGAAGAAGAACGGCCTC |
| | TTCGGTAACCTGATTGCTCTCTCTCTTGGTCTGACCCCCAACTTCAAGTCCAACTTTGA |
| | CCTCGCCGAGGACGCCAAGCTCCAGCTGTCCAAGGACACCTACGATGACGATCTGGACA |
| | ACCTCCTGGCCCAGATCGGTGACCAGTACGCCGATCTCTTCCTTGCCGCCAAGAACCTC |
| | TCCGACGCCATCCTGCTCTCCGACATCCTCCGAGTCAACACCGAGATTACCAAGGCTCC |
| | TCTGTCTGCCTCTATGATCAAGCGATACGACGAGCACCACCAGGATCTCACTCTTCTCA |
| | AGGCTCTCGTCCGACAGCAGCTCCCCGAGAAGTACAAGGAGATTTTCTTTGACCAGTCC |
| | AAGAACGGTTACGCTGGCTACATTGACGGTGGTGCTTCCCAGGAAGAGTTTTACAAGTT |
| | CATCAAGCCTATTCTGGAGAAGATGGACGGTACCGAGGAGCTGCTCGTCAAGCTCAACC |
| | GAGAGGACCTCCTTCGAAAGCAGCGAACCTTCGATAACGGCTCCATCCCCCACCAGATC |
| | CACCTGGGTGAGCTCCACGCCATTCTCCGAAGACAAGAGGACTTCTACCCCTTCCTAAA |
| | GGATAACCGAGAGAAGATCGAGAAGATTCTCACCTTCCGAATCCCCTACTACGTCGGTC |
| | CCCTCGCTCGAGGTAACTCCCGATTTGCTTGGATGACCCGAAAGTCCGAGGAGACTATC |
| | ACCCCCTGGAACTTTGAAGAGGTAGTCGACAAGGGTGCCTCCGCCCAGTCTTTCATTGA |
| | GCGGATGACCAACTTCGATAAGAACCTCCCCAACGAGAAGGTCCTTCCCAAGCACTCTC |
| | TCCTCTACGAGTACTTCACCGTCTACAACGAGCTGACCAAGGTCAAGTACGTTACCGAG |
| | GGCATGCGAAAGCCCGCTTTCCTCTCTGGTGAGCAGAAGAAGGCCATTGTCGACCTCCT |
| | GTTCAAGACTAACCGAAAAGTCACCGTCAAGCAGCTCAAGGAAGACTACTTCAAGAAGA |
| | TTGAGTGCTTCGACTCCGTCGAGATTTCCGGTGTCGAGGACCGATTCAACGCCTCCCTC |
| | GGCACCTACCACGATCTTCTGAAGATCATCAAGGACAAGGACTTTCTTGATAACGAGGA |
| | GAACGAGGACATTCTCGAGGACATCGTCCTCACCCTCACCCTTTTCGAGGATCGAGAGA |
| | TGATCGAGGAGCGACTCAAGACCTACGCCCATCTCTTCGACGACAAGGTCATGAAGCAA |
| | CTCAAGCGACGACGATACACTGGCTGGGGCCGACTTTCCCGAAAGCTCATCAACGGCAT |

TABLE 11-continued sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text.

| SEQ ID NO: | sequence 5' to 3' |
|---|---|
| | CCGAGACAAGCAGTCTGGCAAGACCATCCTGGACTTCCTGAAGTCCGACGGTTTCGCCA |
| | ACCGAAACTTCATGCAGCTCATCCACGACGACTCTCTTACCTTCAAAGAGGATATCCAG |
| | AAGGCCCAGGTTTCTGGCCAGGGCGACTCCCTCCACGAGCACATTGCCAACCTCGCCGG |
| | ATCCCCCGCCATCAAAAAGGGTATCCTCCAGACCGTCAAGGTTGTCGACGAACTCGTGA |
| | AGGTCATGGGCCGACACAAGCCCGAGAACATCGTTATCGAGATGGCCCGAGAGAACCAG |
| | ACCACCCAGAAGGGTCAGAAGAACTCCCGAGAGCGAATGAAGCGAATCGAAGAGGGTAT |
| | CAAGGAGCTCGGTTCCCAGATTCTCAAGGAGCACCCCGTCGAGAACACCCAGCTCCAGA |
| | ACGAGAAACTCTACCTGTACTACCTCCAGAATGGCCGAGACATGTACGTTGACCAGGAG |
| | CTCGACATCAACCGACTCTCCGACTACGACGTCGACCACATTGTTCCTCAGTCCTTCCT |
| | CAAGGACGACTCCATCGACAACAAGGTTCTGACCCGATCTGACAAGAACCGAGGTAAGT |
| | CCGACAACGTTCCCTCCGAAGAGGTCGTTAAGAAGATGAAGAACTACTGGCGACAGCTT |
| | CTCAACGCCAAACTGATCACCCAGCGAAAGTTTGACAACCTCACCAAGGCCGAGCGAGG |
| | TGGTCTGTCCGAGCTGGACAAGGCCGGCTTCATTAAGCGACAGCTGGTCGAGACTCGAC |
| | AGATCACCAAGCACGTCGCCCAGATCCTCGACTCCCGAATGAACACCAAGTACGACGAG |
| | AACGACAAGCTCATCCGGGAGGTCAAGGTCATCACCCTGAAGTCTAAGCTTGTCTCCGA |
| | CTTCCGAAAGGACTTCCAGTTCTACAAGGTCCGAGAGATCAACAACTACCACCACGCCC |
| | ACGACGCCTACCTCAACGCCGTTGTTGGTACCGCCCTCATCAAGAAGTATCCCAAGCTC |
| | GAGTCCGAGTTCGTTTACGGCGACTACAAGGTTTACGATGTCCGAAAGATGATTGCCAA |
| | GTCCGAGCAGGAGATCGGTAAGGCCACCGCCAAGTACTTTTTCTACTCCAACATCATGA |
| | ATTTCTTCAAGACCGAGATCACTCTCGCCAACGGTGAGATTCGAAAGCGACCCCTGATT |
| | GAGACTAATGGTGAGACTGGTGAGATCGTCTGGGATAAGGGCCGAGACTTCGCCACCGT |
| | CCGAAAGGTCCTGTCCATGCCCCAGGTCAACATTGTCAAGAAGACCGAGGTCCAGACCG |
| | GTGGCTTCTCCAAGGAGTCCATTCTCCCCAAGCGAAACTCCGACAAACTCATCGCCCGT |
| | AAGAAGGACTGGGATCCGAAGAAGTACGGTGGTTTCGATTCTCCCACCGTTGCCTACTC |
| | CGTCCTCGTTGTTGCTAAAGTCGAGAAGGGTAAGTCTAAGAAACTCAAGTCCGTGAAGG |
| | AGCTACTCGGTATCACCATCATGGAGCGATCTTCTTTTGAGAAGAACCCCATTGACTTC |
| | CTCGAGGCCAAGGGTTACAAAGAGGTCAAGAAGGACCTGATTATCAAGCTGCCCAAGTA |
| | CTCCCTCTTTGAGCTCGAGAACGGCCGAAAGCGAATGCTGGCTTCCGCTGGTGAGCTGC |
| | AGAAGGGCAACGAGCTCGCTCTGCCCTCCAAGTACGTCAACTTCCTCTACCTGGCCTCC |
| | CACTACGAGAAGCTCAAGGGCTCCCCCGAGGACAACGAGCAGAAGCAGCTGTTCGTTGA |
| | GCAGCACAAGCACTACCTCGACGAGATCATCGAGCAGATCTCCGAGTTCTCCAAGCGAG |
| | TCATCCTCGCTGACGCCAACCTTGATAAGGTTCTCTCTGCTTACAACAAGCACCGGGAC |
| | AAGCCCATCCGAGAGCAGGCCGAGAATATCATCCACCTCTTCACTCTCACCAACCTCGG |
| | CGCTCCTGCTGCCTTCAAGTACTTCGACACCACCATTGACCGAAAGAGGTACACCTCCA |
| | CCAAGGAAGTCCTCGACGCCACCCTGATCCACCAGTCCATCACCGGCCTCTACGAAACC |
| | CGAATCGACCTCTCCCAGCTCGGCGGTGACTCTCGAGCCGACCCCAAGAAGAAGCGAAA |
| | AGTCTAAATATCCGAAGATCAAGAGCGAAGCAAGTTGTAAGTCCAGGACATGTTTCCCG |
| | CCCACGCGAGTGATTTATAACACCTCTCTTTTTTGACACCCGCTCGCCTTGAAATTCAT |
| | GTCACATAAATTATAGTCAACGACGTTTGAATAACTTGTCTTGTAGTTCGATGATGATC |
| | ATATGATTACATTAATAGTAATTACTGTATTTGATATATATACTAATTACAATAGTACA |
| | TATTAGAACATACAATAGTTAGTGCCGTGAAGTGGCTTAAAATACCGCGAGTCGATTAC |
| | GTAATATTATTACCTCTTGCCCATCGAACGTACAAGTACTCCTCTGTTCTCTCCTTCCT |
| | TTGCTTTGTGCACGAAGAACTGCGGTCAGGTGACACAACTTTTTCCATCTCAGGGTGTG |
| | TCGCGTGTGCTTCATCCAAACTTTAGTTGGGGTTCGGGTTCGCGCGAGATGATCACGTG |
| | CCCTGATTTGGTGTCGTCCCCCGTCGCGCTGCGCACGTGATTTATTTATTTCCGGTGGC |
| | TGCTGTCTACGCGGGGCCTTCTCTGCCCTTCTGTTTCAACCTTCGGGCGGTTCTCGTAA |
| | CCAGCAGTAGCAATCCATTTCGAAACTCAAAGAGCTAAAAACGTTAAACCTCAGCAGTC |
| | GCTCGACGAATGGGCTGCGGTTGGGAAGCCCACGAGGCCTATAGCCAGAGCCTCGAGTT |
| | GACAGGAGCCCAGACGCCTTTTCCAACGGCAACTTTTATATAAAATGGCAATGTATTCA |
| | TGCAATTGCGGCCGTGTCAGGTTGGAGACACTGGACCACACTCTCCATTGCTTCCTGAG |
| | GAGATGGATCATTGCTAGTGCATCTACGCGCAGCAATCCCGCAAGCTCGACAACCGTAG |
| | ATGGGCTTTGGTGGGCCAATCAATTACGCAACCCGCACGTTAAATTGTATGAGGAAGGA |
| | AGGCCACGGTACAAAGTGGGTGGTCTTCACCCAGTGGTTGTTGGTGGCGTCATGCAGAC |
| | CATGCATTGGGGATAGCACAGGGTTGGGGTGTCTTGTGGACTCAATGGGTGAAAGGAGA |
| | TGGAAAAGGGCGGTGAAAAGTGGTAGAATCGAAATCCCTGACGTCAATTTATAAAGTAA |
| | AATGCGTTTCTGCCATTTTGCTCCCCTCCTTCTTTCGCAATCGCCTCCCCAAAAGTTGT |
| | CGTGGCAGTACACATGCTTGCATACAATGAAGCTAATCCGGCTTGCTCAGTAGTTGCTA |
| | TATCCAGGCATGGTGTGAAACCCCTCAAAGTATATATAGGAGCGGTGAGCCCCAGTCTG |
| | GGGTCTTTTCTCTCCATCTCAAAACTACTTTCTCACAATGACGAGACTGATGAGTCCGT |
| | GAGGACGAAACGAGTAAGCTCGTCGGTGGCCTGGATTCGAGTGGGTTTTAGAGCTAGAA |
| | ATAGCAAGTTAAAATAAGGCTAGTCCGTTATCAACTTGAAAAAGTGGCACCGAGTCGGT |
| | GCTTTTGGCCGGCATGGTCCCAGCCTCCTCGCTGGCGCCGGCTGGGCAACATGCTTCGG |
| | CATGGCGAATGGGACTAAACTTCGAGCTAATCCAGTAGCTTACGTTACCCAGGGGCAGG |
| | TCAACTGGCTAGCCACGAGTCTGTCCCAGGTCGCAATTTAGTGTAATAAACAATATATA |
| | TATTGAGTCTAAAGGGAATTGTAGCTATTGTGATTGTGTGATTTTCGTCTTGCTGGTTC |
| | TTATTGTGTCCCATTCGTTTCATCCTGATGAGGACCCCTGGAACCGGTGTTTTCTTAGT |
| | CTCTGCAATCGCTAGTCTTGTTGCTATGACAGTTGCGTCGACACTATTCAGGTCATCTA |
| | TCGGTTATTCTGATATTATAATACCTCCGGATCGATGTACCTGATTTATACTTGCAGCA |
| | ATGTTTACTTCTTATCGTTGGACCCCGTCTTCAATTACACTTCCCAACTGGGAACACCC |
| | CTCTTTATCGACCCATTTTAGGTAATTTACCCTAGCCCATTGTCTCCATAAGGAATATT |
| | ACCCTAACCCACAGTCCAGGGTGCCCAGGTCCTTCTTTGGCCAAATTTTAACTTCGGTC |
| | CTATGGCACAGCGGTAGCGCGTGAGATTGCAAATCTTAAGGTCCCGAGTTCGAATCTCG |

TABLE 11-continued

| sequences. SEQ ID NOs: 2, 4, 6, 8 refer to the polynucleotides expressing LIP2, LIP3, LIP4, LIP8, respectively, according to SEQ ID NOS: 1, 3, 5, 7. For more details, see text. | |
|---|---|
| SEQ ID NO: | sequence 5' to 3' |
| | GTGGGACCTAGTTGAAAAATACCTCTAATGCGCCGATGGTTTAGTGGTAAAATCCATCG<br>TTGCCATCGATGGGCCCCCGGTTCGATTCCGGGTCGGCGCAGGTTGACGTTTACACCCA<br>CTCTATCGGAGGTTTTAGAGCTAGAAATAGCAAGTTAAAATAAGGCTAGTCCGTTATCA<br>ACTTGAAAAAGTGGCACCGAGTCGGTGCTTTTTTTTTTCGCGATACACGAATGTGATAC<br>GGATCAAAGTAAGCAGGACTACGATAAGATAACGAATGCGGTGCAGTCCATGTCGATTA<br>GGTATAGATACATTTATTTTGTGTTATGTTACATTTTGGGGGGATACTGTCCTACTTGT<br>AGTACCTACTTGTAGTGGCGCGTCTATTCCTTTGCCCTCGGACGAGTGCTGGGGCGTCG<br>GTTTCCACTATCGGCGAGTACTTCTACACAGCCATCGGTCCAGACGGCCGCGCTTCTGC<br>GGGCGATTTGTGTACGCCCGACAGTCCCGGCTCCGGATCGGACGATTGCGTCGCATCGA<br>CCCTGCGCCCAAGCTGCATCATCGAAATTGCCGTCAACCAAGCTCTGATAGAGTTGGTC<br>AAGACCAATGCGGAGCATATACGCCCGGAGCCGCGGCGATCCTGCAAGCTCCGGATGCC<br>TCCGCTCGAAGTAGCGCGTCTGCTGCTCCATACAAGCCAACCACGGCCTCCAGAAGAAG<br>ATGTTGGCGACCTCGTATTGGGAATCCCCGAACATCGCCTCGCTCCAGTCAATGACCGC<br>TGTTATGCGGCCATTGTCCGTCAGGACATTGTTGGAGCCGAAATCCGCGTGCACGAGGT<br>GCCGGACTTCGGGGCAGTCCTCGGCCCAAAGCATCAGCTCATCGAGAGCCTGCGCGACG<br>GACGCACTGACGGTGTCGTCCATCACAGTTTGCCAGTGATACACATGGGGATCAGCAAT<br>CGCGCATATGAAATCACGCCATGTAGTGTATTGACCGATTCCTTGCGGTCCGAATGGGC<br>CGAACCCGCTCGTCTGGCTAAGATCGGCCGCAGCGATCGCATCCATGGCCTCCGCGACC<br>GGCTGCAGAACAGCGGGCAGTTCGGTTTCAGGCAGGTCTTGCAACGTGACACCCTGTGC<br>ACGGCGGGAGATGCAATAGGTCAGGCTCTCGCTGAATTCCCCAATGTCAAGCACTTCCG<br>GAATCGGGAGCGCGGCCGATGCAAAGTGCCGATAAACATAACGATCTTTGTAGAAACCA<br>TCGGCGCAGCTATTTACCCGCAGGACATATCCACGCCCTCCTACATCGAAGCTGAAAGC<br>ACGAGATTCTTCGCCCTCCGAGAGCTGCATCAGGTCGGAGACGCTGTCGAACTTTTCGA<br>TCAGAAACTTCTCGACAGACGTCGCGGTGAGTTCAGGCTTTTTCATATGGGTACCTGAG<br>AACATTTTTGTGTCTAGGTGTTTGTGTTTGGACTGCGATCAGTGAAGAAAAGAAGAGGA<br>AAAATTGTGCAAGAAATTTTGCTTTCAAGACTTGGCTGATGCAGCAGGGTAACTCTGGG<br>ACACAGACCTATGTTTGTGGTTAAACTCAATGCACGTGGTACGTGCGTGGAGCGCTTAC<br>CCATCCAAGGGTGTGGACATGGAACCGACGGTCCGTGGAGTTGTGTAATGTCATTTTGG<br>CGACTCTTGAAGCAAGGCTATAAAAAAATTGTGTGGCTTGAGTCTTATCGAGCTCGGTC<br>ACTACAAGAGTTAATCTTCCTGTCTCAGGCAGACAGGTCAGGCAGGGTTACTTTTGGGT<br>GTGCTGTAACTCACTGTATGGCCGTTAGTGCGCATAGACGTTGTACATACTGGACCGAA<br>TTGTAGCGTGCTCAATAGGGCCAATAAAGCTATTGTAGGGATCCGAATTTTCAGAACCT<br>AATTTATCTGTTACCCGGCCTGTGGCTCGCACAGCTTAAAAATGGTCAAACTTTCCCCT<br>TCTTGTCTTTTTTTCCTCACATTCATCAGGTTCTTGTCTTGATCTTTCAAGTGAGTATT<br>AATTACCGACCTTGGTTCTTCATTGGGAGAGCATTGGAAGCCGTGGTGCAGCAACCACA<br>AAACGGTTCTTCCCCTTCGATACCTTCTTGCCTGCCTTTCAATACAAGTCGGCTCGATT<br>AGCGGTGGTCGCCCCCGCCAGCGGAGAACATGGAACTAACCCAGAATGAGAGCTAAGTG<br>GAGAAAGAAGAGAGTCAGACGACTCAAGCGAAAGCGCCGCAAGGTCCGAGCTCGATCCA<br>AATAAGCGGTTTTTAACGGAGATTTAACACTAAATCGAAGAACTTTTCCCGTTTCATTT<br>GCGAATGAGCTCGTTAACAAAATCCCCCAGTTTTTTATCCAGCTGTAAGGATTGACAT<br>TAGTAATGAATTATTGTTTGGTATATTTAAATCTGTAGTTCCTTTCTGTCCGTGTCGGC<br>AACTGTCGTACTCGTGATTTACTTGTATTGACGAATACTTACTGTAGCGCACTCTGCTG<br>CTACTGGTCGTAAGGATGTGCTATTTCGGTGTATGGTGGGTTTTTGGGGGTCGGAACC<br>GAAGACTGTTACACGGGCACGGCTCGTTGTGTACACGCACAGAGCTCTTGCGAGTCATG<br>TTGTAGCTAGCTCGTCGTGTTCAGGAACTGTTCGATGGTTCGGAGAGAGTCGCCGCCCA<br>GAACATACGCGCACCGATGTCAGCAGACAGCCTTATTACAAGTATATTCAAGCAAGTAT<br>ATCCGTAGGGTGCGGGTGATTTGGATCTAAGGTTCGTACTCAACACTCACGAGCAGCTT<br>GCCTATGTTACATCCTTTTATCAGACATAACATAATTGGAGTTTACTTACACACGGGGT<br>GTACCTGTATGAGCACCACCTACAATTGTAGCACTGGTACTTGTACAAAGAATTTATTC<br>GTACGAATCACAGGGACGGCCGCCCTCACCGAACCAGCGAATACCTCAGCGGTCCCCTG<br>CAGTGACTCAACAAAGCGATATGAACATCTTGCGATGGTATCCTGCTGATAGTTTTTAC<br>TGTACAAACACCTGTGTAGCTCCTTCTAGCATTTTTAAGTTATTCACACCTCAAGGGGA<br>GGGATAAATTAAATAAATTCCAAAAGCGAAGATCGAGAAACTAAATTAAAATTCCAAAA<br>ACGAAGTTGGAACACAACCCCCCGAAAAAAAACAACAAACAAAAAACCCAACAAAATAA<br>ACAAAAACAAAATAAATATATAACTACCAGTATCTGACTAAAAGTTCAAATACTCGTAC<br>TTACAACAAATAGAAATGAGCCGGCCAAAATTCTGCAGAAAAAAATTTCAAACAAGTAC<br>TGGTATAATTAAATTAAAAAACACATCAAAGTATCATAACGTTAGTTATTTTATTTTAT<br>TTAATAAAAGAAAACAACAAGATGGGCTCAAAACTTTCAACTTATACGATACATACCAA<br>ATAACAATTTAGTATTTATCTAAGTGCTTTTCGTAGATAATGGAATACAAATGGATATC<br>CAGAGTATACACATGGATAGTATACACTGACACGACAATTCTGTATCTCTTTATGTTAA<br>CTACTGTGAGGCATTAAATAGAGCTTGATATATAAAATGTTACATTTCACAGTCTGAAC<br>TTTTGCAGATTACCTAATTTGGTAAGATATTAATTATGAACTGAAAGTTGATGGCATCC<br>CTAAATTTGATGAAAGATGAAATTGTAAATGAGGTGGTAAAAGAGCTACAGTCGTTTTG<br>TTTTGAGATACCATCATCTCTAACGAAATATCTATTAAAAATCTCAGTGTGATCATGAG<br>TCATTGCCATCCTGGAAAATGTCATCATGGCTGATATTTCTAACTGTTTACTTGAGATA<br>AATATATATTTACAAGAACTTCCCTTGAAATTAATTTAGATATAAAATGTTTGCGGGCA<br>AGTTACTACGAGGAATAAATTATATCTAGA |

The invention claimed is:

1. A process for fermentative production of isoprenoids with less than 40 carbons as backbone in a two-phase culture system, comprising in situ extraction of said isoprenoids, wherein the process comprises cultivating a suitable host cell in the presence of a carbon source and a lipophilic solvent, wherein the lipophilic solvent is different from the carbon source, and wherein the lipophilic solvent comprises isoparaffins wherein the host cell is a fungal cell.

2. The process according to claim 1, wherein the lipophilic solvent further comprises a cycloalkane and/or a straight chain alkane.

3. The process according to claim 1, wherein the fermentation product is selected from the group consisting of apocarotenoids and sesquiterpenes.

4. The process according to claim 1, wherein the carbon source is selected from linear alkanes, free fatty acids, ethanol, glucose, and triglycerides.

5. The process according to claim 1 further comprising detecting one or more impurities produced by the process, wherein the impurities are selected from the group consisting of retinal, retinol, fatty acid retinyl esters (FAREs), dihydro-retinol, dihydro-retinyl acetate, dihydro FAREs, rosafluene, phytoene, ergosterol, and dihydro-beta-ionone.

6. The process according to claim 1, wherein the fermentation product comprises retinyl acetate, and wherein the process further comprises isolating the lipophilic solvent comprising the fermentation product.

7. The process according to claim 3, wherein the fermentation product is selected from the group consisting of retinoids and ionones.

8. The process according to claim 3, wherein the fermentation product is selected from the group consisting of retinyl acetate, alpha-ionone, and beta-ionone.

9. The process according to claim 4, wherein the carbon source comprises oleic acid, palmitic acid, linoleic acid, or oil originated from corn, soy, olive, sunflower, canola, cottonseed, rapeseed, sesame, safflower, grapeseed or mixtures thereof.

10. The process according to claim 1, wherein the host cell is selected from *Yarrowia, Rhodosporidium, Lipomyces, Saccharomyces* and *Rhodotorula.*

11. The process according to claim 6 further comprising isolating the fermentation product and measuring the color of the fermentation product.

12. The process according to claim 1, wherein the isoparaffin is a terminally methylated form of a straight chain alkane.

13. The process according to claim 1, wherein the isoparffin is a synthetic isoparaffinic hydrocarbon fluid comprising branched-chain isomers, which contain six to twenty six carbons, and were produced by the chemically coupling of smaller alkane precursors and hydrogenation to remove unsaturation and trace aromatics.

* * * * *

SEQUENCE LISTING

<160> NUMBER OF SEQ ID NOS: 17

<210> SEQ ID NO 1
<211> LENGTH: 334
<212> TYPE: PRT
<213> ORGANISM: Yarrowia lipolytica

<400> SEQUENCE: 1

```
Met Lys Leu Ser Thr Ile Leu Phe Thr Ala Cys Ala Thr Leu Ala Ala
1               5                   10                  15

Ala Leu Pro Ser Pro Ile Thr Pro Ser Glu Ala Ala Val Leu Gln Lys
            20                  25                  30

Arg Val Tyr Thr Ser Thr Glu Thr Ser His Ile Asp Gln Glu Ser Tyr
        35                  40                  45

Asn Phe Phe Glu Lys Tyr Ala Arg Leu Ala Asn Ile Gly Tyr Cys Val
    50                  55                  60

Gly Pro Gly Thr Lys Ile Phe Lys Pro Phe Asn Cys Gly Leu Gln Cys
65                  70                  75                  80

Ala His Phe Pro Asn Val Glu Leu Ile Glu Glu Phe His Asp Pro Arg
                85                  90                  95

Leu Ile Phe Asp Val Ser Gly Tyr Leu Ala Val Asp His Ala Ser Lys
            100                 105                 110

Gln Ile Tyr Leu Val Ile Arg Gly Thr His Ser Leu Glu Asp Val Ile
        115                 120                 125

Thr Asp Ile Arg Ile Met Gln Ala Pro Leu Thr Asn Phe Asp Leu Ala
    130                 135                 140

Ala Asn Ile Ser Ser Thr Ala Thr Cys Asp Asp Cys Leu Val His Asn
145                 150                 155                 160

Gly Phe Ile Gln Ser Tyr Asn Asn Thr Tyr Asn Gln Ile Gly Pro Lys
                165                 170                 175

Leu Asp Ser Val Ile Glu Gln Tyr Pro Asp Tyr Gln Ile Ala Val Thr
            180                 185                 190

Gly His Ser Leu Gly Gly Ala Ala Ala Leu Leu Phe Gly Ile Asn Leu
        195                 200                 205

Lys Val Asn Gly His Asp Pro Leu Val Val Thr Leu Gly Gln Pro Ile
    210                 215                 220

Val Gly Asn Ala Gly Phe Ala Asn Trp Val Asp Lys Leu Phe Phe Gly
225                 230                 235                 240

Gln Glu Asn Pro Asp Val Ser Lys Val Ser Lys Asp Arg Lys Leu Tyr
                245                 250                 255

Arg Ile Thr His Arg Gly Asp Ile Val Pro Gln Val Pro Phe Trp Asp
            260                 265                 270

Gly Tyr Gln His Cys Ser Gly Glu Val Phe Ile Asp Trp Pro Leu Ile
        275                 280                 285

His Pro Pro Leu Ser Asn Val Val Met Cys Gln Gly Gln Ser Asn Lys
    290                 295                 300

Gln Cys Ser Ala Gly Asn Thr Leu Leu Gln Gln Val Asn Val Ile Gly
305                 310                 315                 320

Asn His Leu Gln Tyr Phe Val Thr Glu Gly Val Cys Gly Ile
                325                 330
```

<210> SEQ ID NO 2
<211> LENGTH: 1005
<212> TYPE: DNA
<213> ORGANISM: Yarrowia lipolytica

<400> SEQUENCE: 2

```
atgaagcttt ccaccatcct cttcacagcc tgcgctaccc tggctgccgc cctcccttcc      60
cccatcactc cttctgaggc cgcagttctc cagaagcgag tgtacacctc taccgagacc     120
tctcacattg accaggagtc ctacaacttc tttgagaagt acgcccgact cgcaaacatt     180
ggatattgtg ttggtcccgg cactaagatc ttcaagccct tcaactgtgg cctgcaatgt     240
gcccacttcc ccaacgttga gctcatcgag gagttccacg acccccgtct catctttgat     300
gtttctggtt acctcgctgt tgatcatgcc tccaagcaga tctaccttgt tattcgagga     360
acccactctc tggaggacgt cataaccgac atccgaatca tgcaggctcc tctgacgaac     420
tttgatcttg ctgctaacat ctcttctact gctacttgtg atgactgtct tgtccacaat     480
ggcttcatcc agtcctacaa caacacctac aatcagatcg gccccaagct cgactctgtg     540
attgagcagt atcccgacta ccagattgct gtcaccggtc actctctcgg aggagctgca     600
gcccttctgt tcggaatcaa cctcaaggtt aacggccacg atcccctcgt tgttactctt     660
ggtcagccca ttgtcggtaa cgctggcttt gctaactggg tcgataaact cttctttggc     720
caggagaacc ccgatgtctc caaggtgtcc aaagaccgaa agctctaccg aatcacccac     780
cgaggagata tcgtccctca agtgcccttc tgggacggtt accagcactg ctctggtgag     840
gtctttattg actggcccct gatccaccct cctctctcca acgttgtcat gtgccagggc     900
cagagcaata aacagtgctc tgccggtaac actctgctcc agcaggtcaa tgtgattgga     960
aaccatctgc agtacttcgt caccgagggt gtctgtggta tctaa                    1005
```

<210> SEQ ID NO 3
<211> LENGTH: 498
<212> TYPE: PRT
<213> ORGANISM: Yarrowia lipolytica

<400> SEQUENCE: 3

```
Met Pro Leu Glu Leu Pro Ser Leu Asn Ala Ser Ile Val Gly Asn Thr
1               5                   10                  15

Val Gln Asn Gly Ala Val Glu Gln Phe Leu Asn Ile Arg Tyr Ala Asp
            20                  25                  30

Ile Pro Gly Lys Phe Glu Lys Pro Val Leu Lys Asn Asp Trp Asn Gly
        35                  40                  45

Ala Glu Ile Asp Ala Thr Lys Val Gly Pro Val Cys Pro Gln Pro Arg
    50                  55                  60

Thr Pro Phe Asn Phe Phe Ser Val Pro Asp Asp Leu Trp Glu Lys Val
65                  70                  75                  80

Asn Val Asp Thr Tyr Gln Asp Gly Leu Leu Cys Asp Asn Leu Ile Val
                85                  90                  95

Thr Arg Pro Lys Gly Val Ser Ala Asn Ala Arg Leu Pro Thr Val Val
            100                 105                 110

Trp Ile His Gly Gly Ser Asn Ile Glu Gly Ser Ile Tyr Asn Leu Ile
        115                 120                 125

Tyr Glu Pro Gln Phe Leu Val Ala Glu Ser Val Arg Val Gly Lys Pro
    130                 135                 140

Ile Val His Val Cys Ile Glu Tyr Arg Leu Gly Leu Ala Gly Phe Leu
145                 150                 155                 160

Thr Lys Asn Gly Lys Gly Asn Trp Gly Thr Trp Asp Gln Tyr Thr Gly
                165                 170                 175

Cys Gln Trp Val Asn Arg His Ile Gln Asp Phe Gly Gly Asp Pro Leu
            180                 185                 190
```

```
Asn Val Thr Leu Thr Gly Glu Ser Ala Gly Ser Val Ala Val His Asn
        195                 200                 205

Met Leu Ile Lys Asp Ser Met Asn Gly Arg Lys Leu Phe Arg Asn Ala
    210                 215                 220

Val Met Met Ser Gly Thr Leu Glu Thr Ile Thr Pro Gln Pro Pro Lys
225                 230                 235                 240

Trp His Ala Arg Leu Glu Glu Lys Val Ala Lys Val Thr Gly Lys Glu
                245                 250                 255

Val Ala Asp Leu Ala Ser Leu Ser Asp Lys Glu Leu Leu Asp Ala Gln
            260                 265                 270

Ile Lys Leu Asn Val Ala Val Cys Met Thr Cys Asp Asp Gly Asp Phe
        275                 280                 285

Phe Glu Pro Gly Trp Lys Gln His Leu Thr Pro Asp Trp Leu Asp Lys
    290                 295                 300

Leu Ile Ile Ser Asp Cys Lys Asp Glu Gly Met Leu Tyr Phe Leu Pro
305                 310                 315                 320

Val Asn Ala Gln Asp Asp Glu Glu Leu Leu Ala Lys Val Ala Lys Ser
                325                 330                 335

Pro Val Gly Lys Glu Ile Ser Glu Leu Tyr Gly Ile Lys Glu Gly Gly
            340                 345                 350

Asp Ile Lys Ser Ala Cys Leu Asp Leu Lys Thr Asp Ala Thr Phe Asn
        355                 360                 365

Tyr Phe Asn His Leu Leu Phe Lys Lys Met Glu Glu Ala Arg Asn Asn
    370                 375                 380

Gly Ser Thr Ser Arg Val Tyr Arg Leu Ala Val Asp Glu Pro Asn Pro
385                 390                 395                 400

His Asn Pro Asp Gln Arg Ala His His Ala Val Asp Val Leu Tyr Met
                405                 410                 415

Phe Asn Ser Thr Lys Phe Asn Glu His Gly Asp Lys Leu Ser Arg Leu
            420                 425                 430

Phe Gln Ser His Phe Leu Arg Leu Ala Tyr Gly Leu Glu Pro Trp Asp
        435                 440                 445

His Arg Asn Phe Gly Val Tyr Arg Asn Gly Gly Tyr Gln Gln Leu Pro
    450                 455                 460

Leu Ser Glu Leu Asn Lys Val Arg Pro Val Glu Arg Tyr Glu Ala Leu
465                 470                 475                 480

Ser Lys Met Asp Phe Gly Gln Val Gly Arg Leu Ser Asn Ala Leu Ser
                485                 490                 495

Arg Leu


<210> SEQ ID NO 4
<211> LENGTH: 1497
<212> TYPE: DNA
<213> ORGANISM: Yarrowia lipolytica

<400> SEQUENCE: 4

atgcctctcg aactcccctc gctcaacgcc tcgattgtcg gcaacaccgt tcagaacggc      60

gctgttgagc agtttctcaa catccgatac gccgacattc ctggcaagtt tgagaagccc     120

gtgctcaaga acgattggaa cggcgcggag atcgacgcca ccaaggtcgg tcccgtgtgc     180

ccccaacccc gcaccccatt caacttcttc tccgtgccag acgacctctg ggagaaagtc     240

aatgtggaca cgtaccagga cggtctgctg tgcgacaacc tgattgtgac gcgaccgaag     300

ggcgtgtctg ccaacgcccg gctgcccact gttgtgtgga tccacggcgg ctccaatatt     360
```

```
gagggcagta tctacaacct catctatgag ccccagttcc tggtggcaga gtcggtgcga    420

gtaggcaagc cgattgtgca cgtgtgtatc gagtaccgac tgggtctcgc gggcttcctc    480

accaagaacg gcaagggcaa ctggggcacg tgggatcagt acacgggctg ccagtgggtc    540

aaccgccaca ttcaggactt tggaggcgat cctttgaacg tgacattgac cggtgagtct    600

gccggctctg tagcagtcca taacatgctc atcaaggact ccatgaacgg ccgaaagttg    660

ttccgaaatg ccgtcatgat gagtggcact ctcgagacca tcactcctca gcctcccaag    720

tggcatgctc gtttggagga gaaggtggcc aaggtcactg gcaaggaagt ggccgacctt    780

gcttctctgt ccgataagga gctgctcgac gcccagatca agctcaatgt ggctgtgtgc    840

atgacttgcg acgacggcga ctttttcgag cccggatgga agcagcatct gactcctgac    900

tggctcgaca agctcatcat ctccgattgc aaggacgagg gcatgctgta tttcctgcca    960

gtcaacgcgc aggacgacga ggagctgttg gcaaaggtgg ccaagtcgcc cgtgggtaag   1020

gagatttccg agctttacgg catcaaggag ggtggcgata tcaagtctgc gtgtctcgat   1080

ctcaagactg acgccacctt caattacttt aaccatctgc tgttcaagaa gatggaggag   1140

gcccgaaaca acggctccac ttctcgagtt taccgtctgg ccgtcgatga gcccaacccc   1200

cacaaccccg accagcgggc ccaccacgcc gtcgacgtgc tgtacatgtt caactcgacc   1260

aagttcaacg agcacggcga caagctgtct cggctgttcc agagccactt tttgcggctg   1320

gcgtatggcc tggagccctg ggaccatcga aactttggag tgtacagaaa cggcggctac   1380

cagcagctgc cgctgagtga gttgaacaag gtccgacccg tcgagcggta cgaggcgctg   1440

tccaagatgg actttggcca ggttgggcgt ttgtccaatg cgctttcgcg cctatga      1497
```

```
<210> SEQ ID NO 5
<211> LENGTH: 371
<212> TYPE: PRT
<213> ORGANISM: Yarrowia lipolytica

<400> SEQUENCE: 5

Met Val Ser Leu Ser Ala Arg Ile Lys Asp Phe Phe Ser Val Leu Leu
1               5                   10                  15

Leu Gly Ala Ala Thr Ile Thr Pro Ser Thr Gln Thr Ala Gly Val Ser
            20                  25                  30

Gln Gly Phe Tyr Asp Phe Ala Arg Asp Phe Ala His Leu Ser Asn Ile
        35                  40                  45

Ala Tyr Cys Val Asn Ala Pro Ile Thr Pro Leu Asn Pro Asp Phe Thr
    50                  55                  60

Cys Gly Asn Ser Cys Lys His Phe Pro Glu Ile Glu Leu Val Lys Thr
65                  70                  75                  80

Phe Gly Gly Asn Phe Phe Lys Thr Ser Ile Thr Gly Tyr Leu Ala Val
                85                  90                  95

Asp His Val Lys Lys Glu Lys Tyr Val Val Phe Arg Gly Thr Phe Ser
            100                 105                 110

Leu Ala Asp Ala Ile Thr Asp Met Gln Phe Gln Leu Ser Pro Phe Leu
        115                 120                 125

Val Asp Val Pro Ala Leu Asn Thr Phe Ser Ala Asn Asp Thr Thr Ala
    130                 135                 140

Glu Ala Gln Thr His Cys Glu Gly Cys Lys Ile His Asp Gly Phe Ser
145                 150                 155                 160

Lys Ala Phe Thr Glu Thr Trp Gly Asn Ile Gly Glu Asp Leu Gln Lys
                165                 170                 175
```

```
His Leu Asp Ala Asn Pro Asp Tyr Gln Leu Tyr Val Thr Gly His Ser
            180                 185                 190

Leu Gly Ala Ala Met Ala Leu Leu Gly Ala Thr Ser Ile Lys Leu Lys
        195                 200                 205

Gly Tyr Asp Pro Ile Leu Ile Asn Tyr Gly Gln Pro Arg Val Gly Asn
    210                 215                 220

Lys Pro Phe Ala Glu Phe Ile Asn Lys Leu Trp Phe Gly Glu Gly Asn
225                 230                 235                 240

Gly Leu Glu Ile Thr Pro Glu Arg Lys Leu Tyr Arg Met Thr His Trp
                245                 250                 255

Asn Asp Ile Phe Val Gly Leu Pro Asn Trp Glu Gly Tyr Thr His Ser
            260                 265                 270

Asn Gly Glu Val Tyr Ile Asn Asn Arg Phe Ile Asn Pro Pro Leu Lys
        275                 280                 285

Asp Val Ile Ser Cys Ala Gly Gly Glu Asn Ser Lys Cys Tyr Arg Ser
    290                 295                 300

Ser Phe Ser Leu Leu Ser Gln Ile Asn Leu Leu Gln Asn His Leu Ala
305                 310                 315                 320

Tyr Ile Asp Tyr Ile Gly Tyr Cys Ala Leu Asn Ile Gly Arg Arg Glu
                325                 330                 335

Leu Ala Asp Gln Glu His Tyr Thr Gly Pro Tyr Tyr Tyr Gly His Arg
            340                 345                 350

Ser Glu Glu Asp Phe Lys Lys Leu Gly Leu Glu Leu Ser Thr Pro Gln
        355                 360                 365

Val Glu Asn
    370


<210> SEQ ID NO 6
<211> LENGTH: 1116
<212> TYPE: DNA
<213> ORGANISM: Yarrowia lipolytica

<400> SEQUENCE: 6

atggtatccc tctctgctcg aatcaaagac ttttttttcgg tcctcctcct cggagctgca      60

accatcactc cctccacaca gaccgcaggc gtgtctcaag ggttctatga ttttgctcgg     120

gactttgccc atctgtccaa cattgcctac tgtgtcaatg ctcccatcac tccactgaac     180

ccggacttca cctgtggcaa ctcgtgcaag cactttccgg aaattgagct tgtgaagaca     240

tttggaggca acttcttcaa gacctccatt acgggctacc tggctgtcga tcatgtcaag     300

aaggagaagt acgttgtctt ccgaggaacc ttttcgctgg cagacgcgat cacggacatg     360

cagttccagc tgtctccttt cctggtcgat gtgcctgccc tgaacacttt ctcagctaat     420

gacaccaccg cagaggccca gacgcactgt gagggctgca aaattcacga cggcttctcc     480

aaggccttta ccgagacctg ggtaacatt ggtgaggatc tgcagaaaca cctggacgct     540

aacccggact accagctgta cgtgactggc cattctctgg gagctgctat ggcccttctt     600

ggagctactt ccatcaagct caagggctac gatcccattc tcatcaacta cggacagccc     660

cgagtcggaa acaagccctt cgctgagttc attaacaagt tgtggtttgg agaaggcaac     720

ggtctggaaa tcacccccga gagaaagctg taccgaatga cccactggaa cgacatcttt     780

gttggcctgc ccaactggga gggatacacc cactctaacg gtgaagtata catcaacaac     840

cggttcatca accctcctct caaggatgtc atctcttgtg ctggaggcga aaactcgaag     900

tgctaccgat cctcgttcag cctgctgtcc cagatcaatc tgctccaaaa ccacctggct     960
```

```
tacattgatt acattggata ctgcgctctg aacattggtc gacgagagct tgccgatcag   1020

gaacattaca ctggtcctta ttactatggt catcgatctg aggaggactt taagaagttg   1080

ggcttggagc tatccacccc acaagttgag aactga                             1116


<210> SEQ ID NO 7
<211> LENGTH: 406
<212> TYPE: PRT
<213> ORGANISM: Yarrowia lipolytica

<400> SEQUENCE: 7

Met Ala Gly Phe Asn Phe Thr Phe Gly Gln Val Ile Ser Tyr Leu Ala
1               5                   10                  15

Ser Met Leu Tyr Gly Gln Val Asp Ala Thr Ser Ser Ser Thr Arg Ile
            20                  25                  30

Gln Ala Thr Gln Asp Leu Tyr Asp Phe Thr Ala Lys Phe Ser Arg Leu
        35                  40                  45

Ser Asn Ile Ala Tyr Cys Ile Asn Ala Pro Phe Thr Pro Leu Arg Thr
    50                  55                  60

Asp Phe Thr Cys Gly Glu Ser Cys Arg Tyr Phe Pro Asp Leu Gln Leu
65                  70                  75                  80

Asp Ser Val Phe Gly Gly Asn Phe Ser Ser Ala Ser Thr Thr Gly Tyr
                85                  90                  95

Ile Ala Tyr Asp His Lys Lys Lys Glu Lys Tyr Ile Val Phe Arg Gly
            100                 105                 110

Thr Phe Ser Ile Pro Asp Ile Ile Thr Asp Ile Gln Phe Gln Thr Ala
        115                 120                 125

Pro Trp Leu Thr Ser Leu Pro Thr His Leu Ile Pro Thr Lys Glu Asp
    130                 135                 140

Phe Glu His Lys Gln Ala Ile Leu Lys His Tyr Ala Ala Glu Asn Lys
145                 150                 155                 160

Gly Leu Ser Asn Leu Glu Glu Arg Gln Asp Val Val His Glu Asp Pro
                165                 170                 175

Ser Leu Val Pro Lys Lys Met Asp Lys Cys Glu Asn Cys Gln Ile His
            180                 185                 190

Asp Gly Phe Ala Lys Gly Phe Asn Glu Thr Ile Glu His Ala Gly Pro
        195                 200                 205

Gln Ile Glu Lys Phe Leu Gly Asn Asn Thr Asp Tyr Lys Met Phe Val
    210                 215                 220

Val Gly His Ser Leu Gly Ala Ala Gln Ala Gln Leu Phe Ala Thr Gln
225                 230                 235                 240

Phe Lys Leu Leu Gly Phe Asp Pro Tyr Met Ile Asn Phe Gly Gln Pro
                245                 250                 255

Arg Leu Gly Asn Pro Glu Phe Ala Ala Tyr Ile Asn Gln Leu Trp Phe
            260                 265                 270

Asn Asp Thr Gly Leu Val Val Asn Asp Ala Arg Arg Phe Tyr Arg Val
        275                 280                 285

Thr His Trp Asn Asp Ile Val Val Gly Val Pro Asp Trp Leu Asn Tyr
    290                 295                 300

Thr His Ser Ile Gly Glu Val Phe Ile Asp Glu Glu Ser Val Tyr Pro
305                 310                 315                 320

Lys Leu Asp Lys Val Val Val Cys Glu Gly Gly Glu Asn Pro Leu Cys
                325                 330                 335

His Arg Gly Thr Phe Asn Leu Trp Ser Arg Ile Asn Phe Leu Gln Asn
```

```
            340                 345                 350

His Leu Ala Tyr Ile Phe Tyr Ile Gly Leu Cys Ala Phe Asn Ile Gly
        355                 360                 365

Arg Arg Asp Val Leu Asn Met Pro Gln Tyr Gln Gly Asn Phe Ser Tyr
    370                 375                 380

Gln His Asn Ile Asp Pro Asn Tyr Asn Tyr Asp Thr Lys Val Pro Thr
385                 390                 395                 400

Arg Ile Ser Lys Ser Asn
                405


<210> SEQ ID NO 8
<211> LENGTH: 1221
<212> TYPE: DNA
<213> ORGANISM: Yarrowia lipolytica

<400> SEQUENCE: 8

atggcagggt tcaacttcac tttcgggcag gtgatttcgt acctggcttc catgctctat     60

ggacaggtgg atgccacttc atcctccact cgaatccagg ccacccagga tctgtacgac    120

ttcacagcca agttttcgcg actctcaaac atcgcgtact gcatcaatgc cccccttcacg    180

cctctcagaa cggacttcac ctgcggagaa agctgtcggt acttccccga cctccagctg    240

gactcagtgt ttggtggtaa cttctcctca gcctccacta ccggctacat tgcatacgac    300

cacaagaaga aggaaaagta cattgtgttt cgaggaactt tcagtatccc tgatatcatc    360

acagacattc aatttcagac tgccccttgg ttgacctctc tgcccacgca tctgatccct    420

accaaggagg actttgaaca caagcaggcc atcctgaagc actacgctgc cgaaaacaag    480

ggtctcagca acctggaaga gcgacaggat gttgtgcatg aagaccctag cctggttccc    540

aagaaaatgg acaagtgcga gaactgccag atccatgacg gattcgccaa gggcttcaac    600

gagactatcg agcatgccgg accccagatt gaaaagttcc tgggcaataa caccgactac    660

aagatgtttg ttgttggcca ctctctagga gctgctcagg cccagctgtt tgctacacag    720

ttcaaactgc tgggatttga cccttacatg atcaactttg gacagcctcg acttggaaac    780

cctgagttcg ccgcctacat caaccagctg tggttcaacg atactggtct ggttgtcaat    840

gatgcccgac gattctaccg agtgactcac tggaacgata tcgtcgtggg agtgcccgac    900

tggctcaatt acacccactc tatcggagag gtgttcatag acgaggagag cgtttacccc    960

aagctggaca aggtggtggt gtgcgaggga ggagagaacc ccctgtgcca ccgaggaact   1020

ttcaacctgt ggtcacgaat caacttcctg cagaaccatt tggcttatat cttctacatt   1080

ggtctgtgtg ctttcaacat tggccgaaga gacgtgctca acatgccaca ataccagggc   1140

aacttctcgt accagcacaa catcgacccc aactacaatt acgataccaa ggttcccacc   1200

cggatcagta aatcaaacta a                                              1221


<210> SEQ ID NO 9
<211> LENGTH: 11606
<212> TYPE: DNA
<213> ORGANISM: Artificial Sequence
<220> FEATURE:
<223> OTHER INFORMATION: expression plasmid

<400> SEQUENCE: 9

cgcgtggatc gccggtgcgt tgacgttggt gacctccagc cagaggtgcc cggcgccccg     60

ctcgccggcg aactccgtcg cgagccccat caacgcgcgc ccgaccccgt gcccccggtg    120

ctccggggcg acctcgatgt cctcgacggt cagccggcgg ttccacgccg agtacgagat    180
```

```
gaccacgaag cccgccaggt cgccgtcgtc cccgtacgcg acgaacgtcc gggagtccgg    240
gtcgccgtcc tccccgtcgt ccgattcgtc gtccgattcg tcgtcgggga acaccttggt    300
caggggcggg tccaccggca cctcccgcag ggtgaagccg tccccggtgg cggtgacgcg    360
gaagacggtg tcggtggtga aggacccatc cagtgcctcg atggcctcgg cgtcccccgg    420
gacactggtg cggtaccggt aagccgtgtc gtcaagagtg gtcatttttg tgtctaggtg    480
tttgtgtttg gactgcgatc agtgaagaaa agaagaggaa aaattgtgca agaaattttg    540
ctttcaagac ttggctgatg cagcagggta actctgggac acagacctat gtttgtggtt    600
aaactcaatg cacgtggtac gtgcgtggag cgcttaccca tccaagggtg tggacatgga    660
accgacggtc cgtggagttg tgtaatgtca ttttggcgac tcttgaagca aggctataaa    720
aaaattgtgt ggcttgagtc ttatcgagct cggtcactac aagagttaat cttcctgtct    780
caggcagaca ggtcaggcag ggttactttt gggtgtgctg taactcactg tatggccgtt    840
agtgcgcata gacgttgtac atactggacc gaattgtagc gtgctcaata gggccaataa    900
agctattgta gggatccgaa ttttcagaac ctaatttatc tgttacccgg cctgtggctc    960
gcacagctta aaaatggtca aactttcccc ttcttgtctt tttttcctca cattcatcag   1020
gttcttgtct tgatctttca agtgagtatt aattaccgac cttggttctt cattgggaga   1080
gcattggaag ccgtggtgca gcaaccacaa aacggttctt ccccttcgat accttcttgc   1140
ctgcctttca atacaagtcg gctcgattag cggtggtcgc ccccgccagc ggagaacatg   1200
gaactaaccc agaatgagag ctaagtggag aaagaagaga gtcagacgac tcaagcgaaa   1260
gcgccgcaag gtccgagctc gatccaaata agcggttttt aacggagatt taacactaaa   1320
tcgaagaact tttcccgttt catttgcgaa tgagctcgtt aacaaaatcc cccagttttt   1380
ttatccagct gtaaggattg acattagtaa tgaattattg tttggtatat ttaaatctgt   1440
agttcctttc tgtccgtgtc ggcaactgtc gtactcgtga tttacttgta ttgacgaata   1500
cttactgtag cgcactctgc tgctactggt cgtaaggatg tgctatttcg gtgtatggtg   1560
ggtttttgg gggtcggaac cgaagactgt tacacgggca cggctcgttg tgtacacgca    1620
cagagctctt gcgagtcatg ttgtagctag ctcgtcgtgt tcaggaactg ttcgatggtt   1680
cggagagagt cgccgcccag aacatacgcg caccgatgtc agcagacagc cttattacaa   1740
gtatattcaa gcaagtatat ccgtagggtg cgggtgattt ggatctaagg ttcgtactca   1800
acactcacga gcagcttgcc tatgttacat ccttttatca gacataacat aattggagtt   1860
tacttacaca cggggtgtac ctgtatgagc accacctaca attgtagcac tggtacttgt   1920
acaaagaatt tattcgtacg aatcacaggg acggccgccc tcaccgaacc agcgaatacc   1980
tcagcggtcc cctgcagtga ctcaacaaag cgatatgaac atcttgcgat ggtatcctgc   2040
tgatagtttt tactgtacaa acacctgtgt agctccttct agcattttta agttattcac   2100
acctcaaggg gagggataaa ttaaataaat tccaaaagcg aagatcgaga aactaaatta   2160
aaattccaaa aacgaagttg gaacacaacc ccccgaaaaa aaacaacaaa caaaaaaccc   2220
aacaaaataa acaaaaacaa aataaatata taactaccag tatctgacta aaagttcaaa   2280
tactcgtact tacaacaaat agaaatgagc cggccaaaat tctgcagaaa aaaatttcaa   2340
acaagtactg gtataattaa attaaaaaac acatcaaagt atcataacgt tagttatttt   2400
attttattta ataaaagaaa acaacaagat gggctcaaaa ctttcaactt atacgataca   2460
taccaaataa caatttagta tttatctaag tgcttttcgt agataatgga atacaaatgg   2520
```

```
atatccagag tatacacatg gatagtatac actgacacga caattctgta tctctttatg   2580
ttaactactg tgaggcatta aatagagctt gatatataaa atgttacatt tcacagtctg   2640
aacttttgca gattacctaa tttggtaaga tattaattat gaactgaaag ttgatggcat   2700
ccctaaattt gatgaaagat gaaattgtaa atgaggtggt aaaagagcta cagtcgtttt   2760
gttttgagat accatcatct ctaacgaaat atctattaaa aatctcagtg tgatcatgag   2820
tcattgccat cctggaaaat gtcatcatgg ctgatatttc taactgttta cttgagataa   2880
atatatattt acaagaactt cccttgaaat taatttagat ataaaatgtt tgcgggcaag   2940
ttactacgag gaataaatta tatctagagg ttccgcttcc tcgctcactg actcgctgcg   3000
ctcggtcgtt cggctgcggc gagcggtatc agctcactca aaggcggtaa tacggttatc   3060
cacagaatca ggggataacg caggaaagaa catgtgagca aaaggccagc aaaaggccag   3120
gaaccgtaaa aaggccgcgt tgctggcgtt tttccatagg ctccgccccc ctgacgagca   3180
tcacaaaaat cgacgctcaa gtcagaggtg gcgaaacccg acaggactat aaagatacca   3240
ggcgtttccc cctggaagct ccctcgtgcg ctctcctgtt ccgaccctgc cgcttaccgg   3300
atacctgtcc gcctttctcc cttcgggaag cgtggcgctt tctcatagct cacgctgtag   3360
gtatctcagt tcggtgtagg tcgttcgctc caagctgggc tgtgtgcacg aaccccccgt   3420
tcagcccgac cgctgcgcct tatccggtaa ctatcgtctt gagtccaacc cggtaagaca   3480
cgacttatcg ccactggcag cagccactgg taacaggatt agcagagcga ggtatgtagg   3540
cggtgctaca gagttcttga agtggtggcc taactacggc tacactagaa ggacagtatt   3600
tggtatctgc gctctgctga agccagttac cttcggaaaa agagttggta gctcttgatc   3660
cggcaaacaa accaccgctg gtagcggtgg tttttttgtt tgcaagcagc agattacgcg   3720
cagaaaaaaa ggatctcaag aagatccttt gatcttttct acggggtctg acgctcagtg   3780
gaacgaaaac tcacgttaag ggattttggt catgagatta tcaaaaagga tcttcaccta   3840
gatcctttta aattaaaaat gaagttttaa atcaatctaa agtatatatg agtaaacttg   3900
gtctgacagt taccaatgct taatcagtga ggcacctatc tcagcgatct gtctatttcg   3960
ttcatccata gttgcctgac tccccgtcgt gtagataact acgatacggg agggcttacc   4020
atctggcccc agtgctgcaa tgataccgcg agacccacgc tcaccggctc cagatttatc   4080
agcaataaac cagccagccg gaagggccga gcgcagaagt ggtcctgcaa ctttatccgc   4140
ctccatccag tctattaatt gttgccggga agctagagta agtagttcgc cagttaatag   4200
tttgcgcaac gttgttgcca ttgctgcagg catcgtggtg tcacgctcgt cgtttggtat   4260
ggcttcattc agctccggtt cccaacgatc aaggcgagtt acatgatccc ccatgttgtg   4320
caaaaaagcg gttagctcct tcggtcctcc gatcgttgtc agaagtaagt tggccgcagt   4380
gttatcactc atggttatgg cagcactgca taattctctt actgtcatgc catccgtaag   4440
atgcttttct gtgactggtg agtactcaac caagtcattc tgagaatagt gtatgcggcg   4500
accgagttgc tcttgcccgg cgtcaacacg ggataatacc gcgccacata gcagaacttt   4560
aaaagtgctc atcattggaa aacgttcttc ggggcgaaaa ctctcaagga tcttaccgct   4620
gttgagatcc agttcgatgt aacccactcg tgcacccaac tgatcttcag catcttttac   4680
tttcaccagc gtttctgggt gagcaaaaac aggaaggcaa aatgccgcaa aaaagggaat   4740
aagggcgaca cggaaatgtt gaatactcat actcttcctt tttcaatatt attgaagcat   4800
ttatcagggt tattgtctca tgagcggata catatttgaa tgtatttaga aaaataaaca   4860
aataggggtt ccgcgcacat ttccccgaaa agtgccacct gacgtctaag aaaccattat   4920
```

```
tatcatgaca ttaacctata aaaataggcg tatcacgagg ccctttcgtc tggcctagga   4980
agcgacttcc aatcgctttg catatccagt accacaccca caggcgtttg tgctactcta   5040
ctgatagcaa tagatgcgtc ataattggtt ggcccgctga gcctccacag gatactattg   5100
cacataccct ggtcatgtgc agatcagctc atttgtggag actctggagt aacttagacg   5160
acgcctggtt caattgccgc aatgtgcgcc cacgcagata atgtattgag gggtggagcg   5220
cctcttgggg acttgctgta cttgtacggg atattaaacg cactcagcaa gaccatgacg   5280
taaaacacac ctactgtacg atacgtactg taggtattgt actcgtaccc ggtactacaa   5340
atagtacgat actatacgga gtgtatttgt accttgatat acgactggcg gagtgaagag   5400
aaggagttga acaagaccag atggggatat cagccccagt gctttgtatt acaagtacga   5460
gtacttaata gatactgtaa ggctattgat acggatggca gtaagtcatt gagtaagcaa   5520
ttgtggccca gcatctcccc tacgtacttg taccataccc catggagaca ccaatggtct   5580
ttcacgcaca ctgtcgtgtg ctgtatcgca gaatcgggtg tccaaccaaa tgccgttacc   5640
cccacgtcac agccgataga cagatacacc atcaatacca gcaggttgta tcatgcggtt   5700
ggctgaaggt aagctgattg gtctaaaaac tgtagctgtc ctaattcaac gagcgctatt   5760
tggggccaac cacctcggcc aagcggcctt taatctgcgt gccccagagg cgtctaatga   5820
ggctctggcc gccactgtag gagtgtttct ctgtgcgcac acgcagtttt gagtttgggc   5880
gactttccct ttttcccaat tgcgtacaca cacagctccg agctaagcgc tgtccttgaa   5940
ccttctccct cttttccctc tttttctctt ccccttcccc tcctccacat taaggccaaa   6000
tcctgaattg caccaactag tacaacgaca acaatggaca agaagtactc catcggtttg   6060
gacattggta ctaactctgt cggctgggcc gtcatcaccg acgagtacaa ggttccctcc   6120
aagaagttca aggtccttgg caacaccgac cgacactcta tcaagaagaa cctgatcggt   6180
gctctgctgt tcgactctgg cgagactgcc gaggccaccc gactgaagcg aaccgctcga   6240
cgccgataca cccgacgaaa gaaccgaatc tgttacctcc aggagatctt cagcaacgag   6300
atggctaagg tcgacgactc cttcttccac cgactcgagg agtctttcct ggtcgaagag   6360
gataagaagc acgagcgaca ccccatcttc ggcaacattg ttgatgaggt tgcctaccat   6420
gagaagtacc ccaccatcta ccacctccga aagaagctcg tcgactccac tgacaaggct   6480
gacctccgac tcatctacct tgctctcgcc cacatgatca agttccgagg tcacttcctc   6540
attgagggtg atctcaaccc cgacaactcc gacgttgaca agctgttcat ccagctcgtc   6600
cagacctaca accagctctt tgaggagaac cctatcaacg cttctggtgt tgacgccaag   6660
gccattctct ccgcccgact ctctaagtcc cgacgactcg agaacctcat tgcccagctg   6720
cccggcgaga agaagaacgg cctcttcggt aacctgattg ctctctctct tggtctgacc   6780
cccaacttca agtccaactt tgacctcgcc gaggacgcca agctccagct gtccaaggac   6840
acctacgatg acgatctgga caacctcctg gcccagatcg gtgaccagta cgccgatctc   6900
ttccttgccg ccaagaacct ctccgacgcc atcctgctct ccgacatcct ccgagtcaac   6960
accgagatta ccaaggctcc tctgtctgcc tctatgatca agcgatacga cgagcaccac   7020
caggatctca ctcttctcaa ggctctcgtc cgacagcagc tccccgagaa gtacaaggag   7080
attttctttg accagtccaa gaacggttac gctggctaca ttgacggtgg tgcttcccag   7140
gaagagtttt acaagttcat caagcctatt ctggagaaga tggacggtac cgaggagctg   7200
ctcgtcaagc tcaaccgaga ggacctcctt cgaaagcagc gaaccttcga taacggctcc   7260
```

```
atcccccacc agatccacct gggtgagctc cacgccattc tccgaagaca agaggacttc   7320
taccccttcc taaaggataa ccgagagaag atcgagaaga ttctcacctt ccgaatcccc   7380
tactacgtcg gtcccctcgc tcgaggtaac tcccgatttg cttggatgac ccgaaagtcc   7440
gaggagacta tcacccccctg gaactttgaa gaggtagtcg acaagggtgc ctccgcccag   7500
tctttcattg agcggatgac caacttcgat aagaacctcc ccaacgagaa ggtccttccc   7560
aagcactctc tcctctacga gtacttcacc gtctacaacg agctgaccaa ggtcaagtac   7620
gttaccgagg gcatgcgaaa gcccgctttc ctctctggtg agcagaagaa ggccattgtc   7680
gacctcctgt tcaagactaa ccgaaaagtc accgtcaagc agctcaagga agactacttc   7740
aagaagattg agtgcttcga ctccgtcgag atttccggtg tcgaggaccg attcaacgcc   7800
tccctcggca cctaccacga tcttctgaag atcatcaagg acaaggactt tcttgataac   7860
gaggagaacg aggacattct cgaggacatc gtcctcaccc tcaccctttt cgaggatcga   7920
gagatgatcg aggagcgact caagacctac gcccatctct tcgacgacaa ggtcatgaag   7980
caactcaagc gacgacgata cactggctgg ggccgacttt cccgaaagct catcaacggc   8040
atccgagaca agcagtctgg caagaccatc ctggacttcc tgaagtccga cggtttcgcc   8100
aaccgaaact tcatgcagct catccacgac gactctctta ccttcaaaga ggatatccag   8160
aaggcccagg tttctggcca gggcgactcc ctccacgagc acattgccaa cctcgccgga   8220
tcccccgcca tcaaaaaggg tatcctccag accgtcaagg ttgtcgacga actcgtgaag   8280
gtcatgggcc gacacaagcc cgagaacatc gttatcgaga tggcccgaga gaaccagacc   8340
acccagaagg gtcagaagaa ctcccgagag cgaatgaagc gaatcgaaga gggtatcaag   8400
gagctcggtt cccagattct caaggagcac cccgtcgaga acacccagct ccagaacgag   8460
aaactctacc tgtactacct ccagaatggc cgagacatgt acgttgacca ggagctcgac   8520
atcaaccgac tctccgacta cgacgtcgac cacattgttc ctcagtcctt cctcaaggac   8580
gactccatcg acaacaaggt tctgacccga tctgacaaga accgaggtaa gtccgacaac   8640
gttccctccg aagaggtcgt taagaagatg aagaactact ggcgacagct tctcaacgcc   8700
aaactgatca cccagcgaaa gtttgacaac ctcaccaagg ccgagcgagg tggtctgtcc   8760
gagctggaca aggccggctt cattaagcga cagctggtcg agactcgaca gatcaccaag   8820
cacgtcgccc agatcctcga ctcccgaatg aacaccaagt acgacgagaa cgacaagctc   8880
atccgggagg tcaaggtcat caccctgaag tctaagcttg tctccgactt ccgaaaggac   8940
ttccagttct acaaggtccg agagatcaac aactaccacc acgcccacga cgcctacctc   9000
aacgccgttg ttggtaccgc cctcatcaag aagtatccca agctcgagtc cgagttcgtt   9060
tacggcgact acaaggttta cgatgtccga aagatgattg ccaagtccga gcaggagatc   9120
ggtaaggcca ccgccaagta ctttttctac tccaacatca tgaatttctt caagaccgag   9180
atcactctcg ccaacggtga gattcgaaag cgacccctga ttgagactaa tggtgagact   9240
ggtgagatcg tctgggataa gggccgagac ttcgccaccg tccgaaaggt cctgtccatg   9300
ccccaggtca acattgtcaa gaagaccgag gtccagaccg gtggcttctc caaggagtcc   9360
attctcccca agcgaaactc cgacaaactc atcgcccgta agaaggactg ggatccgaag   9420
aagtacggtg gtttcgattc tcccaccgtt gcctactccg tcctcgttgt tgctaaagtc   9480
gagaagggta agtctaagaa actcaagtcc gtgaaggagc tactcggtat caccatcatg   9540
gagcgatctt cttttgagaa gaaccccatt gacttcctcg aggccaaggg ttacaaagag   9600
gtcaagaagg acctgattat caagctgccc aagtactccc tctttgagct cgagaacggc   9660
```

cgaaagcgaa tgctggcttc cgctggtgag ctgcagaagg gcaacgagct cgctctgccc 9720
tccaagtacg tcaacttcct ctacctggcc tcccactacg agaagctcaa gggctccccc 9780
gaggacaacg agcagaagca gctgttcgtt gagcagcaca agcactacct cgacgagatc 9840
atcgagcaga tctccgagtt ctccaagcga gtcatcctcg ctgacgccaa ccttgataag 9900
gttctctctg cttacaacaa gcaccgggac aagcccatcc gagagcaggc cgagaatatc 9960
atccacctct tcactctcac caacctcggc gctcctgctg ccttcaagta cttcgacacc 10020
accattgacc gaaagaggta cacctccacc aaggaagtcc tcgacgccac cctgatccac 10080
cagtccatca ccggcctcta cgaaacccga atcgacctct cccagctcgg cggtgactct 10140
cgagccgacc ccaagaagaa gcgaaaagtc taaatatccg aagatcaaga gcgaagcaag 10200
ttgtaagtcc aggacatgtt tcccgcccac gcgagtgatt tataacacct ctctttttg 10260 acacccgctc gccttgaaat tcatgtcaca taaattatag tcaacgacgt ttgaataact 10320
tgtcttgtag ttcgatgatg atcatatgat tacattaata gtaattactg tatttgatat 10380
atatactaat tacaatagta catattagaa catacaatag ttagtgccgt gaagtggctt 10440
aaaataccgc gagtcgatta cgtaatatta ttacctcttg cccatcgaac gtacaagtac 10500
tcctctgttc tctccttcct ttgctttgtg cacgaagaac tgcggtcagg tgacacaact 10560
ttttccatct cagggtgtgt cgcgtgtgct tcatccaaac tttagttggg gttcgggttc 10620
gcgcgagatg atcacgtgcc ctgatttggt gtcgtccccc gtcgcgctgc gcacgtgatt 10680
tatttatttc cggtggctgc tgtctacgcg gggccttctc tgcccttctg tttcaacctt 10740
cgggcggttc tcgtaaccag cagtagcaat ccatttcgaa actcaaagag ctaaaaacgt 10800
taaacctcag cagtcgctcg acgaatgggc tgcggttggg aagcccacga ggcctatagc 10860
cagagcctcg agttgacagg agcccagacg ccttttccaa cggcaacttt tatataaaat 10920
ggcaatgtat tcatgcaatt gcggccgtgt caggttggag acactggacc acactctcca 10980
ttgcttcctg aggagatgga tcattgctag tgcatctacg cgcagcaatc ccgcaagctc 11040
gacaaccgta gatgggcttt ggtgggccaa tcaattacgc aacccgcacg ttaaattgta 11100
tgaggaagga aggccacggt acaaagtggg tggtcttcac ccagtggttg ttggtggcgt 11160
catgcagacc atggccgcca gtgtgctgga attgaatatt taccgttcgt ataatgtatg 11220
ctatacgaag ttataccggt ctcgtagtgt tcacgttcag ttcacggtga gcttaaaact 11280
atcttcaaga agagatttga gacctgattt atacttgcag caatgtttac ttcttatcgc 11340
gatacacgaa tgtgatacgg atcaaagtaa gcaggactac gataagataa cgaatgcggt 11400
gcagtccatg tcgattaggt atagatacat ttattttgtg ttatgttaca ttttgggggg 11460
atactgtcct acttgtagta cctacttgta gtggcgcgtt aggggcaggg catgctcatg 11520
tagagcgcct gccgctcgcc gtccgaggcg gtgccgtcgt acagggcggt gtccaggccg 11580
cagagggtga accccatccg ccggta 11606

<210> SEQ ID NO 10
<211> LENGTH: 14006
<212> TYPE: DNA
<213> ORGANISM: Artificial Sequence
<220> FEATURE:
<223> OTHER INFORMATION: expression plasmid

<400> SEQUENCE: 10
gcggagccta ggccggccag cgtggcgcgt ggccatattg gccagcagct tactacagct 60

```
cagccaaagt ggatcatgat ggacggaaat atcggactgg aggccaaaaa ggaggtgctc    120
aaatacgcac gggacaagtc tgcacaggtg gcattcgaac ccacgtctgt ccccaaagcc    180
gctgctcttt ccgagctcaa tctgcccgtt taccccaaca actccattgc cttagccacc    240
cccaacactg cagagctcga ggccatgttc gaggcattcc acgagaaggg ccgatttgac    300
gttgacgact ggtttccagt catagacggt cttgctctcg gagctgactt tagaaacgga    360
gccaccatgt tgtcgcacca acatcgtgga ctcaaagcta ttctcgaaca aggaactctg    420
gcccaggcaa tccacatgct accatacatc ccaactttga tcatcaaggg cggagccaac    480
ggcgtcgtcg tcttccaact cattgatgat atcgagtctg ccattcattc acagcgttct    540
gcttccaata aaacgcctgg cctgttccag aagggcaacg ctgcgagtgg aaacaccaag    600
gtcggcgtct acatgcagta ctttgagccc gaagaagtgg gcagtcagtc gattgtaagc    660
gtgactggag ctggagacac tctgtttgga accctggcca tggagattgt caaggacgag    720
tcctggttga acgatatggg agacaagaag agtgcagttg tttctcgagc catgaacaat    780
gctgtgaaga ctattcagag taaggacgct gtctgcaaga gcatccttta agtgatttgc    840
catgctttct cttcttccac gatgtaaata cttattttac acactactgt gcagtagcaa    900
atacagaaca agagttgtcg cctattgaca gtacagtacg agtagtgtat gtacagtagt    960
tatacaatat ctatgtgaaa ttcgtcggca gctttcggct gatgaactac gagttcttcg   1020
taataaatca tcaacgtaat aagcttggta ccagagacgg gttggcggcg tatttgtgtc   1080
ccaaaaaaca gccccaattg ccccaattga ccccaaattg acccagtagc gggcccaacc   1140
ccggcgagag ccccccttcac cccacatatc aaacctcccc cggttcccac acttgccgtt   1200
aagggcgtag ggtactgcag tctggaatct acgcttgttc agactttgta ctagtttctt   1260
tgtctggcca tccgggtaac ccatgccgga cgcaaaatag actactgaaa atttttttgc   1320
tttgtggttg ggactttagc caagggtata aaagaccacc gtccccgaat tacctttcct   1380
cttcttttct ctctctcctt gtcaactcac acccgaaatc gttaagcatt tccttctgag   1440
tataagaatc attcgctagc cacaaaaatg ggtgatctcg atgcccgagg aacctctgct   1500
caccccgagc tctctgagcg accttctatt atgccttcta tgtctgatat tcaggaccct   1560
tctggtgatg acaaggctac tccccgagga tctgctgctg gtctgcccca gcttgagctt   1620
gctggacacg cccgacgact tggccacctt gagaacttct ttgctgtcca ggctcgacag   1680
cagatttact cttcttttgc tgttttttgt gagtttgaca ctgcttgttc tctcgctcag   1740
cttgcttctg ctgtgcgaaa cgtttgtctt tctaacccccc ttctccttca cactgttgag   1800
cctaagcacc ctgacatcgc tggattctac cactctgacg agtacctttc ccgaccttgg   1860
cctcagcacg attacatgcg agttcttcga gaggttcacg tcgctgacgt tgttatgaac   1920
ggacagaagg agcacgctca cgttgttcga gatgctgttg acgtttttca ggctcacgga   1980
aaccaggtta cttctgagct ccttgagctt atgactcaga ttgagattcc tcacgcttct   2040
cagactcgac cctcttggcg acttctctgt tttccccacg gagaggctaa ccgatggcga   2100
acctttgctt ttgtttctaa ccactgttct tctgatggtc tttctggtct taacttcttt   2160
cgagatctcc agaaggagct tgctcacggc cccacctctg gtgctcctgg tgcccccgga   2220
gcttccggag ttattttcga ttacgctcag gacgctgcta ccctgcccaa gctgcccccct   2280
cccattgatc agaagctcga ttaccgacct tctaagaagg ctcttctcgg ccttctcgct   2340
ggcaagttcg ttcgagagaa gctcggttac gtttctgctg ctcctcccac taccccctacc   2400
tctgaccttg ctcaccctga gggtcaccag tactactgtt accttgttaa cgttcccact   2460
```

```
tcttctgttg cccacattaa gactcaggtg cgagagaacg ttcctcacaa gtgtactctc   2520
actccctttc tccaggcttg ttggcttgtt tctctgttca agtacggtcg agttttttct   2580
ggttcttggc ttgagcgata caccgatgtt cttgttgcta tgaacactcg acagcttctc   2640
cccgaggacc ttgagcttca gcgacagtac cgatacggtt ctaacattgg agctgttcga   2700
tacaactacc ctattgctcc ccttgacgtt cgagataacg atcagaagtt ctggtccctt   2760
gttgagtctt accgacttgc cctttctgat gcccgagata agaacgatta cctttacgct   2820
cttggtgctc ttatgctccc tgagatttac gagaagaaga acgttgatgc tgttgttaac   2880
gataccattc ttaaccagcg acgacaggga accccttcttt ctaacgttgg ttacgttcga   2940
gatgagcagc ccactgcttt tgctattaag aaccacgttt tttctcaggg agttggagct   3000
aaccgaaacg cttttgttct taacatttgt gctaccgatc agggtggtct taacatcgct   3060
atttctattg ctaagggaac ccttgcttct cgacaggagg gacaggagct ttgtgatatt   3120
tttaagtcta ctctccttcg attttaaacg cgtctatccg aagatcaaga gcgaagcaag   3180
ttgtaagtcc aggacatgtt tcccgcccac gcgagtgatt tataacacct ctcttttttg   3240
acacccgctc gccttgaaat tcatgtcaca taaattatag tcaacgacgt ttgaataact   3300
tgtcttgtag ttcgatgatg atcatatgat tacattaata gtaattactg tatctgtacc   3360
tgctgtggac cacgcacggc ggaacgtacc gtacaaatat tttcttgctc acatgactct   3420
ctctcggccg cgcacgccgg tggcaaattg ctcttgcatt ggctctgtct ctagacgtcc   3480
aaaccgtcca aagtggcagg gtgacgtgat gcgacgcacg aaggagatgg cccggtggcg   3540
aggaaccgga cacggcgagc cggcgggaaa aaaggcggaa aacgaaaagc gaagggcaca   3600
atctgacggt gcggctgcca ccaacccaag gaggctattt tgggtcgctt tccatttcac   3660
attcgccctc aatggccact ttgcggtggt gaacatggtt tctgaaacaa ccccccagaa   3720
ttagagtata ttgatgtgtt taagattggg ttgctatttg gccattgtgg gggagggtag   3780
cgacgtggag gacattccag ggcgaattga gcctagaaag tggtaccatt ccaaccgtct   3840
cagtcgtccg aattgatcgc tataactatc acctctctca catgtctact tccccaacca   3900
acatccccaa cctcccccac actaaagttc acgccaataa tgtaggcact ctttctgggt   3960
gtgggacagc agagcaatac ggaggggaga ttacacaacg agccacaatt ggggagatgg   4020
tagccatctc actcgacccg tcgacttttg gcaacgctca attacccacc aaatttgggc   4080
tggagttgag gggaccgtgt tccagcgctg taggaccagc aacacacacg gtatcaacag   4140
caaccaacgc ccccgctaat gcacccagta ctgcgcaggt gtgggccagg tgcgttccag   4200
atgcgagttg gcgaacccta agccgacagt gtactttttg ggacgggcag tagcaatcgt   4260
gggcgtagac cccggtgtat ataaaggggt ggagaggacg gattattagc accaacacac   4320
acacttatac tacatgctag ccacaaaaat gctctctttc ttctggcgaa acggtatcga   4380
gactcccgag cccctcaagg ctgacgtttc cggctctatc cctccctggc ttcagggaac   4440
ccttctccga aacggtcctg gtctgttctc cgttggcaac acttcctaca agcactggtt   4500
cgatggtatg gctctcattc actccttcac ctttaaggat ggtgaggttt tttaccgatc   4560
taagtacctg aagtctgaga cttacaagaa gaacatcgct gccgaccgaa tcgttgtgtc   4620
tgagttcgga accatggtgt accccgatcc ctgcaagaac attttctccc gagccttctc   4680
ttacatgatg aacgccattc ctgactttac cgataacaac ctcattaaca tcattaagta   4740
cggtgaggat tactacgcct cctctgaggt caactacatc aaccagattg accccctgac   4800
```

```
ccttgagact ctcggacgaa ctaactaccg aaaccacatt gccatcaacc ttgccactgc   4860
tcaccctcac tacgacgagg agggtaacac ttacaacatg ggcactgcta ttatgaacct   4920
cggtcgaccc aagtacgtga ttttcaaggt gcccgccaac acctctgata aggagaacaa   4980
gaagcctgcc ctctctgagg tggagcaggt ttgctccatt cccatccgac cctcccttta   5040
cccttcttac ttccactctt ttggcatgac tgagaactac atcatcttcg ttgagcaggc   5100
cttcaagctg gacatcgtca agctggctac tgcttacttc cgagatatta actggggatc   5160
ttgccttaag ttcgaccagg atgacattaa cgtgttccac ctggtcaaca agaagactgg   5220
taaggctgtg tccgtgaagt actacactga ccccttttgtt accttccacc acatcaacgc   5280
ttacgaggac gatggccacg tcgtcttcga tctcattact tacaaggact ctaagctgta   5340
cgatatgttc tacattcaga acatgaagca ggacgtcaag cgatttattg agactaacaa   5400
ggacttcgct cagcccgtgt gccagcgatt tgtccttccc gtcaacgttg ataaggagac   5460
tcctcaggac atcaaccttg tcaagctgca ggacaccact gccactgctg tcctgaagga   5520
ggacggctct gtctactgca cccctgacat catttttaag ggtcttgagc tccctgctat   5580
caactacaag tttaactcta agaagaaccg atacttctac ggcacccgag tggagtggtc   5640
cccttaccct aacaaggtcg ctaaggtgga cgttgttact cgaacccaca agatttggac   5700
tgaggaggag tgttaccctt ctgagcctgt ctttattgcc tcccctgacg ccgttgatga   5760
ggatgacggt gtgattcttt cttctgtggt ttctttcaac ccccagcgac cccctttcct   5820
ggttgtcctc gatgctaagt ccttcaagga gattgctcga gctaccatcg atgcctctat   5880
tcacatggac cttcacggcc ttttcatcca cgacaagtct acctaagttt tttgatcaat   5940
gatccaatgg ctttcacata cccccccacg cctataatta aaacacagag aaatataatc   6000
taacttaata aatattacgg agaatctttc gagtgttcag cagaaatata gccattgtaa   6060
caaaagccgg ctatcgaccg ctttatcgaa gaatatttcc cgccccccag tggccaaacg   6120
atatcggtca gaaggggcag ctctaaacga agaactgcgg tcaggtgaca caactttttc   6180
catctcaggg tgtgtcgcgt gtgcttcatc caaactttag ttggggttcg ggttcgcgcg   6240
agatgatcac gtgccctgat ttggtgtcgt cccccgtcgc gctgcgcacg tgatttattt   6300
atttccggtg gctgctgtct acgcggggcc ttctctgccc ttctgtttca accttcgggc   6360
ggttctcgta accagcagta gcaatccatt tcgaaactca aagagctaaa aacgttaaac   6420
ctcagcagtc gctcgacgaa tgggctgcgg ttgggaagcc cacgaggcct atagccagag   6480
cctcgagttg acaggagccc agacgccttt tccaacggca acttttatat aaaatggcaa   6540
tgtattcatg caattgcggc cgtgtcaggt tggagacact ggaccacact ctccattgct   6600
tcctgaggag atggatcatt gctagtgcat ctacgcgcag caatcccgca agctcgacaa   6660
ccgtagatgg gctttggtgg gccaatcaat tacgcaaccc gcacgttaaa ttgtatgagg   6720
aaggaaggcc acggtacaaa gtgggtggtc ttcacccagt ggttgttggt ggcgtcatgc   6780
agaccatgca ttggggatag cacagggttg gggtgtcttg tggactcaat gggtgaaagg   6840
agatggaaaa gggcggtgaa aagtggtaga atcgaaatcc ctgacgtcaa tttataaagt   6900
aaaatgcgtt tctgccattt tgctcccctc cttctttcgc aatcgcctcc ccaaaagttg   6960
tcgtggcagt acacatgctt gcatacaatg aagctaatcc ggcttgctca gtagttgcta   7020
tatccaggca tggtgtgaaa cccctcaaag tatatatagg agcggtgagc cccagtctgg   7080
ggtcttttct ctccatctca aaactacttt ctcacatgct agccacaaaa atgaccacta   7140
agtacacttc cgttcacgag tctcccaacg gccctggtga cgctcgaccc accgcttccc   7200
```

```
agattatcga cgattacaac cttgagggag agctttctgg caagactgtt ctcgtcaccg   7260
gctgttcctc tggtattggt gttgagactg cccgagctat ttaccgaact ggtgccaccc   7320
tttacctcac tgcccgagat gtcgataagg ccaagaccgt tcttcccgac cttgttgaca   7380
cttcccgagt ccactttctc caccttgacc ttaactctct ggagtctgtt cgaggttttg   7440
ctgagaactt caagtctaag tccactcagc ttcacattct catcgagaac gctggcgtga   7500
tggcctgtcc cgagggccga accgtcgatg gttttgagac tcagtttggt atcaaccacc   7560
ttgctcactt tctcctcttt tacctcctca aggataccct tctcaactct tctacccccg   7620
ctttcaactc ccgagttgtc atcctctctt cttgtgctca ccaggctggt tccgttcacc   7680
ttaacaacct gtctcttgag ggtggatacg agccttggaa gtcttacggc cagtccaaga   7740
ctgccaacct ttggactgcc cgagagatcg agaagcgatt tggtgcttcc ggtatccact   7800
cttgggctgt tcaccccggt tccatcgcta ctgagcttca gcgacacgtt tccgacgagc   7860
ttaagcagaa gtgggctgac gataaggagg gtgccaagct gtggaagtcc accgagcagg   7920
gtgccgccac cactgtcctt gctgctgttt cccctgagct tgagggtaag ggcggtcttt   7980
accttgagga tacccaggtt gccaagcccc ctgcccgagg aatgtttggt gttgctgact   8040
gggcttacga tgaggatggc ccctctaagc tctgggccaa gtctcttgag ctccttaagc   8100
tccagtaaag gttagactat ggatatgtaa tttaactgtg tatatagaga gcgtgcaagt   8160
atggagcgct tgttcagctt gtatgatggt cagacgacct gtctgatcga gtatgtatga   8220
tactgcacaa cctgtgtatc cgcatgatct gtccaatggg gcatgttgtt gtgtttctcg   8280
atacggagat gctgggtaca agtagctaat acgattgaac tacttatact tatatgaggc   8340
ttgaagaaag ctgacttgtg tatgacttat tctcaactac atccccagtc acaataccac   8400
cactgcacta ccactacaca ctagtggtgt gttctgtgga gcattctcac ttttggtaaa   8460
cgacattgct tcaagtgcag cggaatcaaa aagtataaag tgggcagcga gtatacctgt   8520
acagactgta ggcgataact caatccaatt accccccaca acatgactgg ccaaactgat   8580
ctcaagactt tattgaaatc agcaacaccg attctcaatg aaggcacata cttcttctgc   8640
aacattcact tgacgcctaa agttggtgag aaatggaccg acaagacata ttctgctatc   8700
cacggactgt tgcctgtgtc ggtggctaca atacgtgagt cagaagggct gacggtggtg   8760
gttcccaagg aaaaggtcga cgagtatctg tctgactcgt cattgccgcc tttggagtac   8820
gactccaact atgagtgtgc ttggatcact ttgacgatac attcttcgtt ggaggctgtg   8880
ggtctgacag ctgcgttttc ggcgcggttg gccgacaaca atatcagctg caacgtcatt   8940
gctggctttc atcatgatca cattttttgtc ggcaaaggcg acgcccagag agccattgac   9000
gttctttcta atttggaccg atagccgtat agtccagtct atctataagt tcaactaact   9060
cgtaactatt accataacat atacttcact gccccagata aggttccgat aaaaagttct   9120
gcagactaaa tttatttcag tctcctcttc accaccaaaa tgccctccta cgaagctcga   9180
gctaacgtcc acaagtccgc ctttgccgct cgagtgctca agctcgtggc agccaagaaa   9240
accaacctgt gtgcttctct ggatgttacc accaccaagg agctcattga gcttgccgat   9300
aaggtcggac cttatgtgtg catgatcaag acccatatcg acatcattga cgacttcacc   9360
tacgccggca ctgtgctccc cctcaaggaa cttgctctta agcacggttt cttcctgttc   9420
gaggacagaa agttcgcaga tattggcaac actgtcaagc accagtacaa gaacggtgtc   9480
taccgaatcg ccgagtggtc cgatatcacc aacgcccacg gtgtacccgg aaccggaatc   9540
```

```
attgctggcc tgcgagctgg tgccgaggaa actgtctctg aacagaagaa ggaggacgtc   9600
tctgactacg agaactccca gtacaaggag ttcctggtcc cctctcccaa cgagaagctg   9660
gccagaggtc tgctcatgct ggccgagctg tcttgcaagg gctctctggc cactggcgag   9720
tactccaagc agaccattga gcttgcccga tccgaccccg agtttgtggt tggcttcatt   9780
gcccagaacc gacctaaggg cgactctgag gactggctta ttctgacccc cggggtgggt   9840
cttgacgaca agggagacgc tctcggacag cagtaccgaa ctgttgagga tgtcatgtct   9900
accggaacgg atatcataat tgtcggccga ggtctgtacg gccagaaccg agatcctatt   9960
gaggaggcca agcgatacca gaaggctggc tgggaggctt accagaagat taactgttag  10020
aggttagact atggatatgt aatttaactg tgtatataga gagcgtgcaa gtatggagcg  10080
cttgttcagc ttgtatgatg gtcagacgac ctgtctgatc gagtatgtat gatactgcac  10140
aacctgtgta tccgcatgat ctgtccaatg gggcatgttg ttgtgtttct cgatacggag  10200
atgctgggta caagtagcta atacgattga actacttata cttatatgag gcttgaagaa  10260
agctgacttg tgtatgactt attctcaact acatccccag tcacaatacc accactgcac  10320
taccactaca cctcgagcat gcacactatt atcacattac tacatccaaa cccctacagg  10380
gggaggagct ctccaatcaa atatgtacat taactatctc tcgtaaatca ttgttataag  10440
accgtccgtg actgtctaaa tcggttcatt cgttgtaaca aatcagtgta acaactcgtg  10500
gtacgcccgg tttgcttcgc tcacgctccc ctagattttc cgtctaggac acaacaagcc  10560
ctggtggatg acgttcaacg ccttcagcgc gtctttttcc tcaataacac acgagatgtt  10620
aatttcgttg gctccctgag aaatcatctc aatgttaata cctgcctggg ccagagtaga  10680
gaagaacatg cctgcacatc cgaccatggc cttcattctc gttccgatca gcgacacaat  10740
ggtcatgcct cgcttcacat ctactgtgcc gtactttcgc agctcctcca cagcctgctt  10800
gaggttggag tcgggagcat ggaaggccat cgacacatgg acctcagaag tggagatgag  10860
atcgacgaca agtttctgct ggtcgagagt agcaaagatc ttgttcaaga agccatgact  10920
cttggttcgc ttattcgaat gaacgttgag aacggtgata ttcgatttgg tagtgacagc  10980
tgtaggcttc ttctcgtcat ctacaggagc agacacctgg ggagtgaatg agccagagga  11040
cagagaagtt agcgagtcgg tggaagaagc cagatcctgg acattgtttt tcgttttcag  11100
gttgcccgag ccgtcagcag atgggtagat gatagttcct cctcccaggg ggttttccac  11160
gtttttgatt cggataggaa tatgggcctt aatgacctgc tccatggtga aggggtggat  11220
gacttcagat ccgtagtagg tcaactcagc ggcctcctcg gggtaatga tgggcagcag  11280
acgggcagtg gacacctttc tgggatcggc agtgaagaca ccatcgactt ctttccagat  11340
ctgaagctcc ttggcgtcca gacccacagc caccagagca gcacacagat cggtgtatcc  11400
tcgtccgatc tggcttagga ggcctccctt gacggggcca aagaaaccgg tcaacacggg  11460
caccatgttt cccttgacag gagcagagtc cgtgttagga gagccgggaa gagtgatgat  11520
ctcgcccaga acacgtccga ggtccgaata gaacttggga tcttcggcat tggtggtggt  11580
aactgcgtga gacaggtcaa agtaccgtgc gttaacacca gcgtcccgca taactgcagt  11640
catgtacatg caactgagct tctccccaat ggccatgatg gagtcgagtg ttcgggggga  11700
gatctcagaa atgatttcag cagcagccag gattcgcaac agctggtcgc actcgccgtt  11760
gatgtcggca ttgaggtttt cgagcagttc ggggttcttg acgtcacgct tagcagctgc  11820
aagatggtct tctcggatag actcaatgat ggggttgtag gcgtctgatc cgagaagagc  11880
agagtcagca gcagcaataa gacgggtggt ggttccctcg gccttggtgg cctctagatg  11940
```

```
gcctccttgg ccccattcca gctgcattaa tgaatcggcc aacgcgcggg gagaggcggt  12000

ttgcgtattg ggcgctcttc cgcttcctcg ctcactgact cgctgcgctc ggtcgttcgg  12060

ctgcggcgag cggtatcagc tcactcaaag gcggtaatac ggttatccac agaatcaggg  12120

gataacgcag gaaagaacat gtgagcaaaa ggccagcaaa aggccaggaa ccgtaaaaag  12180

gccgcgttgc tggcgttttt ccataggctc cgcccccctg acgagcatca caaaaatcga  12240

cgctcaagtc agaggtggcg aaacccgaca ggactataaa gataccaggc gtttccccct  12300

ggaagctccc tcgtgcgctc tcctgttccg accctgccgc ttaccggata cctgtccgcc  12360

tttctccctt cgggaagcgt ggcgctttct catagctcac gctgtaggta tctcagttcg  12420

gtgtaggtcg ttcgctccaa gctgggctgt gtgcacgaac cccccgttca gcccgaccgc  12480

tgcgccttat ccggtaacta tcgtcttgag tccaacccgg taagacacga cttatcgcca  12540

ctggcagcag ccactggtaa caggattagc agagcgaggt atgtaggcgg tgctacagag  12600

ttcttgaagt ggtggcctaa ctacggctac actagaagaa cagtatttgg tatctgcgct  12660

ctgctgaagc cagttacctt cggaaaaaga gttggtagct cttgatccgg caaacaaacc  12720

accgctggta gcggtggttt ttttgtttgc aagcagcaga ttacgcgcag aaaaaaagga  12780

tctcaagaag atcctttgat cttttctacg gggtctgacg ctcagtggaa cgaaaactca  12840

cgttaaggga ttttggtcat gagattatca aaaaggatct tcacctagat ccttttaaat  12900

taaaaatgaa gttttaaatc aatctaaagt atatatgagt aaacttggtc tgacagttac  12960

caatgcttaa tcagtgaggc acctatctca gcgatctgtc tatttcgttc atccatagtt  13020

gcctgactcc ccgtcgtgta gataactacg atacgggagg gcttaccatc tggccccagt  13080

gctgcaatga taccgcgaga gccacgctca ccggctccag atttatcagc aataaaccag  13140

ccagccggaa gggccgagcg cagaagtggt cctgcaactt tatccgcctc catccagtct  13200

attaattgtt gccgggaagc tagagtaagt agttcgccag ttaatagttt gcgcaacgtt  13260

gttgccattg ctacaggcat cgtggtgtca cgctcgtcgt ttggtatggc ttcattcagc  13320

tccggttccc aacgatcaag gcgagttaca tgatccccca tgttgtgcaa aaaagcggtt  13380

agctccttcg gtcctccgat cgttgtcaga agtaagttgg ccgcagtgtt atcactcatg  13440

gttatggcag cactgcataa ttctcttact gtcatgccat ccgtaagatg cttttctgtg  13500

actggtgagt actcaaccaa gtcattctga gaatagtgta tgcggcgacc gagttgctct  13560

tgcccggcgt caatacggga taataccgcg ccacatagca gaactttaaa agtgctcatc  13620

attggaaaac gttcttcggg gcgaaaactc tcaaggatct taccgctgtt gagatccagt  13680

tcgatgtaac ccactcgtgc acccaactga tcttcagcat cttttacttt caccagcgtt  13740

tctgggtgag caaaaacagg aaggcaaaat gccgcaaaaa agggaataag ggcgacacgg  13800

aaatgttgaa tactcatact cttccttttt caatattatt gaagcattta tcagggttat  13860

tgtctcatga gcggatacat atttgaatgt atttagaaaa ataaacaaat aggggttccg  13920

cgcacatttc cccgaaaagt gccacctgac gtctaagaaa ccattattat catgacatta  13980

acctataaaa ataggcgtat cacgag                                      14006
```

<210> SEQ ID NO 11
<211> LENGTH: 13802
<212> TYPE: DNA
<213> ORGANISM: Artificial Sequence
<220> FEATURE:
<223> OTHER INFORMATION: expression plasmid

<400> SEQUENCE: 11

```
ggttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctgca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaaca   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctggcctag gaagcgactt ccaatcgctt tgcatatcca   2040
gtaccacacc cacaggcgtt tgtgctactc tactgatagc aatagatgcg tcataattgg   2100
ttggcccgct gagcctccac aggatactat tgcacatacc ctggtcatgt gcagatcagc   2160
tcatttgtgg agactctgga gtaacttaga cgacgcctgg ttcaattgcc gcaatgtgcg   2220
cccacgcaga taatgtattg aggggtggag cgcctcttgg ggacttgctg tacttgtacg   2280
ggatattaaa cgcactcagc aagaccatga cgtaaaacac acctactgta cgatacgtac   2340
```

```
tgtaggtatt gtactcgtac ccggtactac aaatagtacg atactatacg gagtgtattt   2400

gtaccttgat atacgactgg cggagtgaag agaaggagtt gaacaagacc agatggggat   2460

atcagcccca gtgctttgta ttacaagtac gagtacttaa tagatactgt aaggctattg   2520

atacggatgg cagtaagtca ttgagtaagc aattgtggcc cagcatctcc cctacgtact   2580

tgtaccatac cccatggaga caccaatggt ctttcacgca cactgtcgtg tgctgtatcg   2640

cagaatcggg tgtccaacca aatgccgtta cccccacgtc acagccgata gacagataca   2700

ccatcaatac cagcaggttg tatcatgcgg ttggctgaag gtaagctgat tggtctaaaa   2760

actgtagctg tcctaattca acgagcgcta tttggggcca accacctcgg ccaagcggcc   2820

tttaatctgc gtgccccaga ggcgtctaat gaggctctgg ccgccactgt aggagtgttt   2880

ctctgtgcgc acacgcagtt ttgagtttgg gcgactttcc ctttttccca attgcgtaca   2940

cacacagctc cgagctaagc gctgtccttg aaccttctcc ctcttttccc tctttttctc   3000

ttccccttcc cctcctccac attaaggcca aatcctgaat tgcaccaact agtacaacga   3060

caacaatgga caagaagtac tccatcggtt tggacattgg tactaactct gtcggctggg   3120

ccgtcatcac cgacgagtac aaggttccct ccaagaagtt caaggtcctt ggcaacaccg   3180

accgacactc tatcaagaag aacctgatcg gtgctctgct gttcgactct ggcgagactg   3240

ccgaggccac ccgactgaag cgaaccgctc gacgccgata cacccgacga aagaaccgaa   3300

tctgttacct ccaggagatc ttcagcaacg agatggctaa ggtcgacgac tccttcttcc   3360

accgactcga ggagtctttc ctggtcgaag aggataagaa gcacgagcga caccccatct   3420

tcggcaacat tgttgatgag gttgcctacc atgagaagta ccccaccatc taccacctcc   3480

gaaagaagct cgtcgactcc actgacaagg ctgacctccg actcatctac cttgctctcg   3540

cccacatgat caagttccga ggtcacttcc tcattgaggg tgatctcaac cccgacaact   3600

ccgacgttga caagctgttc atccagctcg tccagaccta caaccagctc tttgaggaga   3660

accctatcaa cgcttctggt gttgacgcca aggccattct ctccgcccga ctctctaagt   3720

cccgacgact cgagaacctc attgcccagc tgcccggcga gaagaagaac ggcctcttcg   3780

gtaacctgat tgctctctct cttggtctga cccccaactt caagtccaac tttgacctcg   3840

ccgaggacgc caagctccag ctgtccaagg acacctacga tgacgatctg gacaacctcc   3900

tggcccagat cggtgaccag tacgccgatc tcttccttgc cgccaagaac ctctccgacg   3960

ccatcctgct ctccgacatc ctccgagtca acaccgagat taccaaggct cctctgtctg   4020

cctctatgat caagcgatac gacgagcacc accaggatct cactcttctc aaggctctcg   4080

tccgacagca gctccccgag aagtacaagg agattttctt tgaccagtcc aagaacggtt   4140

acgctggcta cattgacggt ggtgcttccc aggaagagtt ttacaagttc atcaagccta   4200

ttctggagaa gatggacggt accgaggagc tgctcgtcaa gctcaaccga gaggacctcc   4260

ttcgaaagca gcgaaccttc gataacggct ccatccccca ccagatccac ctgggtgagc   4320

tccacgccat tctccgaaga caagaggact tctacccctt cctaaaggat aaccgagaga   4380

agatcgagaa gattctcacc ttccgaatcc cctactacgt cggtcccctc gctcgaggta   4440

actcccgatt tgcttggatg acccgaaagt ccgaggagac tatcaccccc tggaactttg   4500

aagaggtagt cgacaagggt gcctccgccc agtctttcat tgagcggatg accaacttcg   4560

ataagaacct ccccaacgag aaggtccttc ccaagcactc tctcctctac gagtacttca   4620

ccgtctacaa cgagctgacc aaggtcaagt acgttaccga gggcatgcga aagcccgctt   4680
```

```
tcctctctgg tgagcagaag aaggccattg tcgacctcct gttcaagact aaccgaaaag   4740
tcaccgtcaa gcagctcaag gaagactact tcaagaagat tgagtgcttc gactccgtcg   4800
agatttccgg tgtcgaggac cgattcaacg cctccctcgg cacctaccac gatcttctga   4860
agatcatcaa ggacaaggac tttcttgata acgaggagaa cgaggacatt ctcgaggaca   4920
tcgtcctcac cctcaccctt ttcgaggatc gagagatgat cgaggagcga ctcaagacct   4980
acgcccatct cttcgacgac aaggtcatga agcaactcaa gcgacgacga tacactggct   5040
ggggccgact ttcccgaaag ctcatcaacg gcatccgaga caagcagtct ggcaagacca   5100
tcctggactt cctgaagtcc gacggtttcg ccaaccgaaa cttcatgcag ctcatccacg   5160
acgactctct taccttcaaa gaggatatcc agaaggccca ggtttctggc cagggcgact   5220
ccctccacga gcacattgcc aacctcgccg gatcccccgc catcaaaaag ggtatcctcc   5280
agaccgtcaa ggttgtcgac gaactcgtga aggtcatggg ccgacacaag cccgagaaca   5340
tcgttatcga gatggcccga gagaaccaga ccacccagaa gggtcagaag aactcccgag   5400
agcgaatgaa gcgaatcgaa gagggtatca aggagctcgg ttcccagatt ctcaaggagc   5460
accccgtcga gaacacccag ctccagaacg agaaactcta cctgtactac ctccagaatg   5520
gccgagacat gtacgttgac caggagctcg acatcaaccg actctccgac tacgacgtcg   5580
accacattgt tcctcagtcc ttcctcaagg acgactccat cgacaacaag gttctgaccc   5640
gatctgacaa gaaccgaggt aagtccgaca acgttccctc cgaagaggtc gttaagaaga   5700
tgaagaacta ctggcgacag cttctcaacg ccaaactgat cacccagcga aagtttgaca   5760
acctcaccaa ggccgagcga ggtggtctgt ccgagctgga caaggccggc ttcattaagc   5820
gacagctggt cgagactcga cagatcacca agcacgtcgc ccagatcctc gactcccgaa   5880
tgaacaccaa gtacgacgag aacgacaagc tcatccggga ggtcaaggtc atcaccctga   5940
agtctaagct tgtctccgac ttccgaaagg acttccagtt ctacaaggtc cgagagatca   6000
acaactacca ccacgcccac gacgcctacc tcaacgccgt tgttggtacc gccctcatca   6060
agaagtatcc caagctcgag tccgagttcg tttacggcga ctacaaggtt tacgatgtcc   6120
gaaagatgat tgccaagtcc gagcaggaga tcggtaaggc caccgccaag tactttttct   6180
actccaacat catgaatttc ttcaagaccg agatcactct cgccaacggt gagattcgaa   6240
agcgacccct gattgagact aatggtgaga ctggtgagat cgtctgggat aagggccgag   6300
acttcgccac cgtccgaaag gtcctgtcca tgccccaggt caacattgtc aagaagaccg   6360
aggtccagac cggtggcttc tccaaggagt ccattctccc caagcgaaac tccgacaaac   6420
tcatcgcccg taagaaggac tgggatccga agaagtacgg tggtttcgat tctcccaccg   6480
ttgcctactc cgtcctcgtt gttgctaaag tcgagaaggg taagtctaag aaactcaagt   6540
ccgtgaagga gctactcggt atcaccatca tggagcgatc ttcttttgag aagaacccca   6600
ttgacttcct cgaggccaag ggttacaaag aggtcaagaa ggacctgatt atcaagctgc   6660
ccaagtactc cctctttgag ctcgagaacg gccgaaagcg aatgctggct tccgctggtg   6720
agctgcagaa gggcaacgag ctcgctctgc cctccaagta cgtcaacttc ctctacctgg   6780
cctcccacta cgagaagctc aagggctccc ccgaggacaa cgagcagaag cagctgttcg   6840
ttgagcagca caagcactac ctcgacgaga tcatcgagca gatctccgag ttctccaagc   6900
gagtcatcct cgctgacgcc aaccttgata aggttctctc tgcttacaac aagcaccggg   6960
acaagcccat ccgagagcag gccgagaata tcatccacct cttcactctc accaacctcg   7020
gcgctcctgc tgccttcaag tacttcgaca ccaccattga ccgaaagagg tacacctcca   7080
```

```
ccaaggaagt cctcgacgcc accctgatcc accagtccat caccggcctc tacgaaaccc   7140
gaatcgacct ctcccagctc ggcggtgact ctcgagccga ccccaagaag aagcgaaaag   7200
tctaaatatc cgaagatcaa gagcgaagca agttgtaagt ccaggacatg tttcccgccc   7260
acgcgagtga tttataacac ctctcttttt tgacacccgc tcgccttgaa attcatgtca   7320
cataaattat agtcaacgac gtttgaataa cttgtcttgt agttcgatga tgatcatatg   7380
attacattaa tagtaattac tgtatttgat atatatacta attacaatag tacatattag   7440
aacatacaat agttagtgcc gtgaagtggc ttaaaatacc gcgagtcgat tacgtaatat   7500
tattacctct tgcccatcga acgtacaagt actcctctgt tctctccttc ctttgctttg   7560
tgcacgaaga actgcggtca ggtgacacaa ctttttccat ctcagggtgt gtcgcgtgtg   7620
cttcatccaa actttagttg gggttcgggt tcgcgcgaga tgatcacgtg ccctgatttg   7680
gtgtcgtccc ccgtcgcgct gcgcacgtga tttatttatt tccggtggct gctgtctacg   7740
cggggccttc tctgcccttc tgtttcaacc ttcgggcggt tctcgtaacc agcagtagca   7800
atccatttcg aaactcaaag agctaaaaac gttaaacctc agcagtcgct cgacgaatgg   7860
gctgcggttg ggaagcccac gaggcctata gccagagcct cgagttgaca ggagcccaga   7920
cgccttttcc aacggcaact tttatataaa atggcaatgt attcatgcaa ttgcggccgt   7980
gtcaggttgg agacactgga ccacactctc cattgcttcc tgaggagatg gatcattgct   8040
agtgcatcta cgcgcagcaa tcccgcaagc tcgacaaccg tagatgggct ttggtgggcc   8100
aatcaattac gcaacccgca cgttaaattg tatgaggaag gaaggccacg gtacaaagtg   8160
ggtggtcttc acccagtggt tgttggtggc gtcatgcaga ccatgcattg ggatagcac    8220
agggttgggg tgtcttgtgg actcaatggg tgaaaggaga tggaaaaggg cggtgaaaag   8280
tggtagaatc gaaatccctg acgtcaattt ataaagtaaa atgcgtttct gccattttgc   8340
tcccctcctt ctttcgcaat cgcctcccca aaagttgtcg tggcagtaca catgcttgca   8400
tacaatgaag ctaatccggc ttgctcagta gttgctatat ccaggcatgg tgtgaaaccc   8460
ctcaaagtat atataggagc ggtgagcccc agtctggggt cttttctctc catctcaaaa   8520
ctactttctc acaatggatt tgctgatgag tccgtgagga cgaaacgagt aagctcgtct   8580
ggaggcatga tcaacagcgg ttttagagct agaaatagca agttaaaata aggctagtcc   8640
gttatcaact tgaaaaagtg gcaccgagtc ggtgcttttg gccggcatgg tcccagcctc   8700
ctcgctggcg ccggctgggc aacatgcttc ggcatggcga atgggactaa acttcgagct   8760
aatccagtag cttacgttac ccaggggcag gtcaactggc tagccacgag tctgtcccag   8820
gtcgcaattt agtgtaataa acaatatata tattgagtct aaagggaatt gtagctattg   8880
tgattgtgtg attttcgtct tgctggttct tattgtgtcc cattcgtttc atcctgatga   8940
ggacccctgg aaccggtgtt ttcttagtct ctgcaatcgc tagtcttgtt gctatgacag   9000
ttgcgtcgac actattcagg tcatctatcg gttattctga tattataata cctccggatc   9060
gatgtacctg atttatactt gcagcaatgt ttacttctta tcgttggacc ccgtcttcaa   9120
ttacacttcc caactgggaa cacccctctt tatcgaccca ttttaggtaa tttaccctag   9180
cccattgtct ccataaggaa tattacccta acccacagtc cagggtgccc aggtccttct   9240
ttggccaaat tttaacttcg gtcctatggc acagcggtag cgcgtgagat tgcaaatctt   9300
aaggtcccga gttcgaatct cggtgggacc tagttgaaaa atacctctaa tgcgccgatg   9360
gtttagtggt aaaatccatc gttgccatcg atgggccccc ggttcgattc cgggtcggcg   9420
```

-continued

```
caggttgacg tacagcaggc tgaacgagga tgttttagag ctagaaatag caagttaaaa   9480
taaggctagt ccgttatcaa cttgaaaaag tggcaccgag tcggtgcttt ttttttcga   9540
tcggccccag ttgcaaaagt tgacacaact ctagatctgc ttccaaatat agaatcataa   9600
caagggttag ggtgtgatta tataatattg gtcttaattg atgtgctagg gctttaaaag   9660
ttggttaaaa taacgctcta atgccttttt aatatattgt ctttttcaaa atctcaaatc   9720
ggacacttct tcgtgtatga gactccattt tttggctccg tcacgtgata tgtattatca   9780
gctatagtgg tgtaaacaaa gtttttact agctgtaatg gcattttgtc ggagtggtaa   9840
atcgccttct tgttgtgcgt tcgagttctg gactctgcac tgggctactt tgaaaaatac   9900
ctctaatgcg ccgatggttt agtggtaaaa tccatcgttg ccatcgatgg gcccccggtt   9960
cgattccggg tcggcgcagg ttgacgttca ctcctcagcc tcccaaggtt ttagagctag  10020
aaatagcaag ttaaaataag gctagtccgt tatcaacttg aaaaagtggc accgagtcgg  10080
tgcttttttt tttcgcgata cacgaatgtg atacggatca aagtaagcag gactacgata  10140
agataacgaa tgcggtgcag tccatgtcga ttaggtatag atacatttat tttgtgttat  10200
gttacatttt ggggggatac tgtcctactt gtagtaccta cttgtagtgg cgcgtctatt  10260
cctttgccct cggacgagtg ctggggcgtc ggtttccact atcggcgagt acttctacac  10320
agccatcggt ccagacggcc gcgcttctgc gggcgatttg tgtacgcccg acagtcccgg  10380
ctccggatcg gacgattgcg tcgcatcgac cctgcgccca agctgcatca tcgaaattgc  10440
cgtcaaccaa gctctgatag agttggtcaa gaccaatgcg gagcatatac gcccggagcc  10500
gcggcgatcc tgcaagctcc ggatgcctcc gctcgaagta gcgcgtctgc tgctccatac  10560
aagccaacca cggcctccag aagaagatgt tggcgacctc gtattgggaa tccccgaaca  10620
tcgcctcgct ccagtcaatg accgctgtta tgcggccatt gtccgtcagg acattgttgg  10680
agccgaaatc cgcgtgcacg aggtgccgga cttcggggca gtcctcggcc caaagcatca  10740
gctcatcgag agcctgcgcg acggacgcac tgacggtgtc gtccatcaca gtttgccagt  10800
gatacacatg gggatcagca atcgcgcata tgaaatcacg ccatgtagtg tattgaccga  10860
ttccttgcgg tccgaatggg ccgaacccgc tcgtctggct aagatcggcc gcagcgatcg  10920
catccatggc ctccgcgacc ggctgcagaa cagcgggcag ttcggtttca ggcaggtctt  10980
gcaacgtgac accctgtgca cggcgggaga tgcaataggt caggctctcg ctgaattccc  11040
caatgtcaag cacttccgga atcgggagcg cggccgatgc aaagtgccga taaacataac  11100
gatctttgta gaaaccatcg gcgcagctat ttacccgcag gacatatcca cgccctccta  11160
catcgaagct gaaagcacga gattcttcgc cctccgagag ctgcatcagg tcggagacgc  11220
tgtcgaactt ttcgatcaga aacttctcga cagacgtcgc ggtgagttca ggctttttca  11280
tatgggtacc tgagaacatt tttgtgtcta ggtgtttgtg tttggactgc gatcagtgaa  11340
gaaaagaaga ggaaaaattg tgcaagaaat tttgctttca agacttggct gatgcagcag  11400
ggtaactctg ggacacagac ctatgtttgt ggttaaactc aatgcacgtg gtacgtgcgt  11460
ggagcgctta cccatccaag ggtgtggaca tggaaccgac ggtccgtgga gttgtgtaat  11520
gtcattttgg cgactcttga agcaaggcta taaaaaaatt gtgtggcttg agtcttatcg  11580
agctcggtca ctacaagagt taatcttcct gtctcaggca gacaggtcag gcagggttac  11640
ttttgggtgt gctgtaactc actgtatggc cgttagtgcg catagacgtt gtacatactg  11700
gaccgaattg tagcgtgctc aatagggcca ataaagctat tgtagggatc cgaattttca  11760
gaacctaatt tatctgttac ccggcctgtg gctcgcacag cttaaaaatg gtcaaacttt  11820
```

```
ccccttcttg tcttttttc ctcacattca tcaggttctt gtcttgatct ttcaagtgag  11880

tattaattac cgaccttggt tcttcattgg gagagcattg gaagccgtgg tgcagcaacc  11940

acaaaacggt tcttcccctt cgataccttc ttgcctgcct ttcaatacaa gtcggctcga  12000

ttagcggtgg tcgcccccgc cagcggagaa catggaacta acccagaatg agagctaagt  12060

ggagaaagaa gagagtcaga cgactcaagc gaaagcgccg caaggtccga gctcgatcca  12120

aataagcggt ttttaacgga gatttaacac taaatcgaag aacttttccc gtttcatttg  12180

cgaatgagct cgttaacaaa atcccccagt ttttttatcc agctgtaagg attgacatta  12240

gtaatgaatt attgtttggt atatttaaat ctgtagttcc tttctgtccg tgtcggcaac  12300

tgtcgtactc gtgatttact tgtattgacg aatacttact gtagcgcact ctgctgctac  12360

tggtcgtaag gatgtgctat ttcggtgtat ggtgggtttt ttgggggtcg gaaccgaaga  12420

ctgttacacg ggcacggctc gttgtgtaca cgcacagagc tcttgcgagt catgttgtag  12480

ctagctcgtc gtgttcagga actgttcgat ggttcggaga gagtcgccgc ccagaacata  12540

cgcgcaccga tgtcagcaga cagccttatt acaagtatat tcaagcaagt atatccgtag  12600

ggtgcgggtg atttggatct aaggttcgta ctcaacactc acgagcagct tgcctatgtt  12660

acatcctttt atcagacata acataattgg agtttactta cacacggggt gtacctgtat  12720

gagcaccacc tacaattgta gcactggtac ttgtacaaag aatttattcg tacgaatcac  12780

agggacggcc gccctcaccg aaccagcgaa tacctcagcg gtcccctgca gtgactcaac  12840

aaagcgatat gaacatcttg cgatggtatc ctgctgatag tttttactgt acaaacacct  12900

gtgtagctcc ttctagcatt tttaagttat tcacacctca aggggaggga taaattaaat  12960

aaattccaaa agcgaagatc gagaaactaa attaaaattc caaaaacgaa gttggaacac  13020

aaccccccga aaaaaaacaa caaacaaaaa acccaacaaa ataaacaaaa acaaaataaa  13080

tatataacta ccagtatctg actaaaagtt caaatactcg tacttacaac aaatagaaat  13140

gagccggcca aaattctgca gaaaaaaatt tcaaacaagt actggtataa ttaaattaaa  13200

aaacacatca aagtatcata acgttagtta ttttatttta tttaataaaa gaaaacaaca  13260

agatgggctc aaaactttca acttatacga tacataccaa ataacaattt agtatttatc  13320

taagtgcttt tcgtagataa tggaatacaa atggatatcc agagtataca catggatagt  13380

atacactgac acgacaattc tgtatctctt tatgttaact actgtgaggc attaaataga  13440

gcttgatata taaaatgtta catttcacag tctgaacttt tgcagattac ctaatttggt  13500

aagatattaa ttatgaactg aaagttgatg gcatccctaa atttgatgaa agatgaaatt  13560

gtaaatgagg tggtaaaaga gctacagtcg ttttgttttg agataccatc atctctaacg  13620

aaatatctat taaaaatctc agtgtgatca tgagtcattg ccatcctgga aaatgtcatc  13680

atggctgata tttctaactg tttacttgag ataaatatat atttacaaga acttcccttg  13740

aaattaattt agatataaaa tgtttgcggg caagttacta cgaggaataa attatatcta  13800

ga                                                                 13802
```

<210> SEQ ID NO 12
<211> LENGTH: 13246
<212> TYPE: DNA
<213> ORGANISM: Artificial Sequence
<220> FEATURE:
<223> OTHER INFORMATION: expression plasmid

<400> SEQUENCE: 12

```
ggttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctgca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaaca   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctggcctag gaagcgactt ccaatcgctt tgcatatcca   2040
gtaccacacc cacaggcgtt tgtgctactc tactgatagc aatagatgcg tcataattgg   2100
ttggcccgct gagcctccac aggatactat tgcacatacc ctggtcatgt gcagatcagc   2160
tcatttgtgg agactctgga gtaacttaga cgacgcctgg ttcaattgcc gcaatgtgcg   2220
cccacgcaga taatgtattg aggggtggag cgcctcttgg ggacttgctg tacttgtacg   2280
ggatattaaa cgcactcagc aagaccatga cgtaaaacac acctactgta cgatacgtac   2340
tgtaggtatt gtactcgtac ccggtactac aaatagtacg atactatacg gagtgtattt   2400
```

```
gtaccttgat atacgactgg cggagtgaag agaaggagtt gaacaagacc agatggggat   2460
atcagcccca gtgctttgta ttacaagtac gagtacttaa tagatactgt aaggctattg   2520
atacggatgg cagtaagtca ttgagtaagc aattgtggcc cagcatctcc cctacgtact   2580
tgtaccatac cccatggaga caccaatggt ctttcacgca cactgtcgtg tgctgtatcg   2640
cagaatcggg tgtccaacca aatgccgtta cccccacgtc acagccgata gacagataca   2700
ccatcaatac cagcaggttg tatcatgcgg ttggctgaag gtaagctgat tggtctaaaa   2760
actgtagctg tcctaattca acgagcgcta tttggggcca accacctcgg ccaagcggcc   2820
tttaatctgc gtgccccaga ggcgtctaat gaggctctgg ccgccactgt aggagtgttt   2880
ctctgtgcgc acacgcagtt ttgagtttgg gcgactttcc ctttttccca attgcgtaca   2940
cacacagctc cgagctaagc gctgtccttg aaccttctcc ctcttttccc tctttttctc   3000
ttccccttcc cctcctccac attaaggcca aatcctgaat tgcaccaact agtacaacga   3060
caacaatgga caagaagtac tccatcggtt tggacattgg tactaactct gtcggctggg   3120
ccgtcatcac cgacgagtac aaggttccct ccaagaagtt caaggtcctt ggcaacaccg   3180
accgacactc tatcaagaag aacctgatcg gtgctctgct gttcgactct ggcgagactg   3240
ccgaggccac ccgactgaag cgaaccgctc gacgccgata cacccgacga aagaaccgaa   3300
tctgttacct ccaggagatc ttcagcaacg agatggctaa ggtcgacgac tccttcttcc   3360
accgactcga ggagtctttc ctggtcgaag aggataagaa gcacgagcga caccccatct   3420
tcggcaacat tgttgatgag gttgcctacc atgagaagta ccccaccatc taccacctcc   3480
gaaagaagct cgtcgactcc actgacaagg ctgacctccg actcatctac cttgctctcg   3540
cccacatgat caagttccga ggtcacttcc tcattgaggg tgatctcaac cccgacaact   3600
ccgacgttga caagctgttc atccagctcg tccagaccta caaccagctc tttgaggaga   3660
accctatcaa cgcttctggt gttgacgcca aggccattct ctccgcccga ctctctaagt   3720
cccgacgact cgagaacctc attgcccagc tgcccggcga gaagaagaac ggcctcttcg   3780
gtaacctgat tgctctctct cttggtctga cccccaactt caagtccaac tttgacctcg   3840
ccgaggacgc caagctccag ctgtccaagg acacctacga tgacgatctg gacaacctcc   3900
tggcccagat cggtgaccag tacgccgatc tcttccttgc cgccaagaac ctctccgacg   3960
ccatcctgct ctccgacatc ctccgagtca acaccgagat taccaaggct cctctgtctg   4020
cctctatgat caagcgatac gacgagcacc accaggatct cactcttctc aaggctctcg   4080
tccgacagca gctccccgag aagtacaagg agattttctt tgaccagtcc aagaacggtt   4140
acgctggcta cattgacggt ggtgcttccc aggaagagtt ttacaagttc atcaagccta   4200
ttctggagaa gatggacggt accgaggagc tgctcgtcaa gctcaaccga gaggacctcc   4260
ttcgaaagca gcgaaccttc gataacggct ccatccccca ccagatccac ctgggtgagc   4320
tccacgccat tctccgaaga caagaggact tctacccctt cctaaaggat aaccgagaga   4380
agatcgagaa gattctcacc ttccgaatcc cctactacgt cggtcccctc gctcgaggta   4440
actcccgatt tgcttggatg acccgaaagt ccgaggagac tatcaccccc tggaactttg   4500
aagaggtagt cgacaagggt gcctccgccc agtctttcat tgagcggatg accaacttcg   4560
ataagaacct ccccaacgag aaggtccttc ccaagcactc tctcctctac gagtacttca   4620
ccgtctacaa cgagctgacc aaggtcaagt acgttaccga gggcatgcga aagcccgctt   4680
tcctctctgg tgagcagaag aaggccattg tcgacctcct gttcaagact aaccgaaaag   4740
```

tcaccgtcaa gcagctcaag gaagactact tcaagaagat tgagtgcttc gactccgtcg 4800
agatttccgg tgtcgaggac cgattcaacg cctccctcgg cacctaccac gatcttctga 4860
agatcatcaa ggacaaggac tttcttgata acgaggagaa cgaggacatt ctcgaggaca 4920
tcgtcctcac cctcaccctt ttcgaggatc gagagatgat cgaggagcga ctcaagacct 4980
acgcccatct cttcgacgac aaggtcatga agcaactcaa gcgacgacga tacactggct 5040
ggggccgact ttcccgaaag ctcatcaacg gcatccgaga caagcagtct ggcaagacca 5100
tcctggactt cctgaagtcc gacggtttcg ccaaccgaaa cttcatgcag ctcatccacg 5160
acgactctct taccttcaaa gaggatatcc agaaggccca ggtttctggc cagggcgact 5220
ccctccacga gcacattgcc aacctcgccg gatcccccgc catcaaaaag ggtatcctcc 5280
agaccgtcaa ggttgtcgac gaactcgtga aggtcatggg ccgacacaag cccgagaaca 5340
tcgttatcga gatggcccga gagaaccaga ccacccagaa gggtcagaag aactcccgag 5400
agcgaatgaa gcgaatcgaa gagggtatca aggagctcgg ttcccagatt ctcaaggagc 5460
accccgtcga gaacacccag ctccagaacg agaaactcta cctgtactac ctccagaatg 5520
gccgagacat gtacgttgac caggagctcg acatcaaccg actctccgac tacgacgtcg 5580
accacattgt tcctcagtcc ttcctcaagg acgactccat cgacaacaag gttctgaccc 5640
gatctgacaa gaaccgaggt aagtccgaca acgttccctc cgaagaggtc gttaagaaga 5700
tgaagaacta ctggcgacag cttctcaacg ccaaactgat cacccagcga aagtttgaca 5760
acctcaccaa ggccgagcga ggtggtctgt ccgagctgga caaggccggc ttcattaagc 5820
gacagctggt cgagactcga cagatcacca agcacgtcgc ccagatcctc gactcccgaa 5880
tgaacaccaa gtacgacgag aacgacaagc tcatccggga ggtcaaggtc atcaccctga 5940
agtctaagct tgtctccgac ttccgaaagg acttccagtt ctacaaggtc cgagagatca 6000
acaactacca ccacgcccac gacgcctacc tcaacgccgt tgttggtacc gccctcatca 6060
agaagtatcc caagctcgag tccgagttcg tttacggcga ctacaaggtt tacgatgtcc 6120
gaaagatgat tgccaagtcc gagcaggaga tcggtaaggc caccgccaag tactttttct 6180
actccaacat catgaatttc ttcaagaccg agatcactct cgccaacggt gagattcgaa 6240
agcgacccct gattgagact aatggtgaga ctggtgagat cgtctgggat aagggccgag 6300
acttcgccac cgtccgaaag gtcctgtcca tgccccaggt caacattgtc aagaagaccg 6360
aggtccagac cggtggcttc tccaaggagt ccattctccc caagcgaaac tccgacaaac 6420
tcatcgcccg taagaaggac tgggatccga agaagtacgg tggtttcgat tctcccaccg 6480
ttgcctactc cgtcctcgtt gttgctaaag tcgagaaggg taagtctaag aaactcaagt 6540
ccgtgaagga gctactcggt atcaccatca tggagcgatc ttcttttgag aagaacccca 6600
ttgacttcct cgaggccaag ggttacaaag aggtcaagaa ggacctgatt atcaagctgc 6660
ccaagtactc cctctttgag ctcgagaacg gccgaaagcg aatgctggct tccgctggtg 6720
agctgcagaa gggcaacgag ctcgctctgc cctccaagta cgtcaacttc ctctacctgg 6780
cctcccacta cgagaagctc aagggctccc ccgaggacaa cgagcagaag cagctgttcg 6840
ttgagcagca caagcactac ctcgacgaga tcatcgagca gatctccgag ttctccaagc 6900
gagtcatcct cgctgacgcc aaccttgata aggttctctc tgcttacaac aagcaccggg 6960
acaagcccat ccgagagcag gccgagaata tcatccacct cttcactctc accaacctcg 7020
gcgctcctgc tgccttcaag tacttcgaca ccaccattga ccgaaagagg tacacctcca 7080
ccaaggaagt cctcgacgcc accctgatcc accagtccat caccggcctc tacgaaaccc 7140

```
gaatcgacct ctcccagctc ggcggtgact ctcgagccga ccccaagaag aagcgaaaag   7200
tctaaatatc cgaagatcaa gagcgaagca agttgtaagt ccaggacatg tttcccgccc   7260
acgcgagtga tttataacac ctctcttttt tgacacccgc tcgccttgaa attcatgtca   7320
cataaattat agtcaacgac gtttgaataa cttgtcttgt agttcgatga tgatcatatg   7380
attacattaa tagtaattac tgtatttgat atatatacta attacaatag tacatattag   7440
aacatacaat agttagtgcc gtgaagtggc ttaaaatacc gcgagtcgat tacgtaatat   7500
tattacctct tgcccatcga acgtacaagt actcctctgt tctctccttc ctttgctttg   7560
tgcacgaaga actgcggtca ggtgacacaa ctttttccat ctcagggtgt gtcgcgtgtg   7620
cttcatccaa actttagttg gggttcgggt tcgcgcgaga tgatcacgtg ccctgatttg   7680
gtgtcgtccc ccgtcgcgct gcgcacgtga tttatttatt tccggtggct gctgtctacg   7740
cggggccttc tctgcccttc tgtttcaacc ttcgggcggt tctcgtaacc agcagtagca   7800
atccatttcg aaactcaaag agctaaaaac gttaaacctc agcagtcgct cgacgaatgg   7860
gctgcggttg ggaagcccac gaggcctata gccagagcct cgagttgaca ggagcccaga   7920
cgccttttcc aacggcaact tttatataaa atggcaatgt attcatgcaa ttgcggccgt   7980
gtcaggttgg agacactgga ccacactctc cattgcttcc tgaggagatg gatcattgct   8040
agtgcatcta cgcgcagcaa tcccgcaagc tcgacaaccg tagatgggct ttggtgggcc   8100
aatcaattac gcaacccgca cgttaaattg tatgaggaag gaaggccacg gtacaaagtg   8160
ggtggtcttc acccagtggt tgttggtggc gtcatgcaga ccatgcattg gggatagcac   8220
agggttgggg tgtcttgtgg actcaatggg tgaaaggaga tggaaaaggg cggtgaaaag   8280
tggtagaatc gaaatccctg acgtcaattt ataaagtaaa atgcgtttct gccattttgc   8340
tcccctcctt ctttcgcaat cgcctcccca aaagttgtcg tggcagtaca catgcttgca   8400
tacaatgaag ctaatccggc ttgctcagta gttgctatat ccaggcatgg tgtgaaaccc   8460
ctcaaagtat atataggagc ggtgagcccc agtctggggt cttttctctc catctcaaaa   8520
ctactttctc acaatgacga gactgatgag tccgtgagga cgaaacgagt aagctcgtcg   8580
gtggcctgga ttcgagtggg ttttagagct agaaatagca agttaaaata aggctagtcc   8640
gttatcaact tgaaaaagtg gcaccgagtc ggtgcttttg gccggcatgg tcccagcctc   8700
ctcgctggcg ccggctgggc aacatgcttc ggcatggcga atgggactaa acttcgagct   8760
aatccagtag cttacgttac ccaggggcag gtcaactggc tagccacgag tctgtcccag   8820
gtcgcaattt agtgtaataa acaatatata tattgagtct aaagggaatt gtagctattg   8880
tgattgtgtg attttcgtct tgctggttct tattgtgtcc cattcgtttc atcctgatga   8940
ggacccctgg aaccggtgtt ttcttagtct ctgcaatcgc tagtcttgtt gctatgacag   9000
ttgcgtcgac actattcagg tcatctatcg gttattctga tattataata cctccggatc   9060
gatgtacctg atttatactt gcagcaatgt ttacttctta tcgttggacc ccgtcttcaa   9120
ttacacttcc caactgggaa cacccctctt tatcgaccca ttttaggtaa tttaccctag   9180
cccattgtct ccataaggaa tattacccta acccacagtc cagggtgccc aggtccttct   9240
ttggccaaat tttaacttcg gtcctatggc acagcggtag cgcgtgagat tgcaaatctt   9300
aaggtcccga gttcgaatct cggtgggacc tagttgaaaa atacctctaa tgcgccgatg   9360
gtttagtggt aaaatccatc gttgccatcg atgggccccc ggttcgattc cgggtcggcg   9420
caggttgacg tttacaccca ctctatcgga ggttttagag ctagaaatag caagttaaaa   9480
```

```
taaggctagt ccgttatcaa cttgaaaaag tggcaccgag tcggtgcttt ttttttcgc   9540
gatacacgaa tgtgatacgg atcaaagtaa gcaggactac gataagataa cgaatgcggt   9600
gcagtccatg tcgattaggt atagatacat ttattttgtg ttatgttaca ttttgggggg   9660
atactgtcct acttgtagta cctacttgta gtggcgcgtc tattcctttg ccctcggacg   9720
agtgctgggg cgtcggtttc cactatcggc gagtacttct acacagccat cggtccagac   9780
ggccgcgctt ctgcgggcga tttgtgtacg cccgacagtc ccggctccgg atcggacgat   9840
tgcgtcgcat cgaccctgcg cccaagctgc atcatcgaaa ttgccgtcaa ccaagctctg   9900
atagagttgg tcaagaccaa tgcggagcat atacgcccgg agccgcggcg atcctgcaag   9960
ctccggatgc ctccgctcga agtagcgcgt ctgctgctcc atacaagcca accacggcct  10020
ccagaagaag atgttggcga cctcgtattg ggaatccccg aacatcgcct cgctccagtc  10080
aatgaccgct gttatgcggc cattgtccgt caggacattg ttggagccga aatccgcgtg  10140
cacgaggtgc cggacttcgg ggcagtcctc ggcccaaagc atcagctcat cgagagcctg  10200
cgcgacggac gcactgacgg tgtcgtccat cacagtttgc cagtgataca catggggatc  10260
agcaatcgcg catatgaaat cacgccatgt agtgtattga ccgattcctt gcggtccgaa  10320
tgggccgaac ccgctcgtct ggctaagatc ggccgcagcg atcgcatcca tggcctccgc  10380
gaccggctgc agaacagcgg gcagttcggt ttcaggcagg tcttgcaacg tgacaccctg  10440
tgcacggcgg gagatgcaat aggtcaggct ctcgctgaat tccccaatgt caagcacttc  10500
cggaatcggg agcgcggccg atgcaaagtg ccgataaaca taacgatctt tgtagaaacc  10560
atcggcgcag ctatttaccc gcaggacata tccacgccct cctacatcga agctgaaagc  10620
acgagattct tcgccctccg agagctgcat caggtcggag acgctgtcga acttttcgat  10680
cagaaacttc tcgacagacg tcgcggtgag ttcaggcttt ttcatatggg tacctgagaa  10740
catttttgtg tctaggtgtt tgtgtttgga ctgcgatcag tgaagaaaag aagaggaaaa  10800
attgtgcaag aaattttgct ttcaagactt ggctgatgca gcagggtaac tctgggacac  10860
agacctatgt ttgtggttaa actcaatgca cgtggtacgt gcgtggagcg cttacccatc  10920
caagggtgtg gacatggaac cgacggtccg tggagttgtg taatgtcatt ttggcgactc  10980
ttgaagcaag gctataaaaa aattgtgtgg cttgagtctt atcgagctcg gtcactacaa  11040
gagttaatct tcctgtctca ggcagacagg tcaggcaggg ttacttttgg gtgtgctgta  11100
actcactgta tggccgttag tgcgcataga cgttgtacat actggaccga attgtagcgt  11160
gctcaatagg gccaataaag ctattgtagg gatccgaatt ttcagaacct aatttatctg  11220
ttacccggcc tgtggctcgc acagcttaaa aatggtcaaa ctttcccctt cttgtctttt  11280
tttcctcaca ttcatcaggt tcttgtcttg atctttcaag tgagtattaa ttaccgacct  11340
tggttcttca ttgggagagc attggaagcc gtggtgcagc aaccacaaaa cggttcttcc  11400
ccttcgatac cttcttgcct gcctttcaat acaagtcggc tcgattagcg gtggtcgccc  11460
ccgccagcgg agaacatgga actaacccag aatgagagct aagtggagaa agaagagagt  11520
cagacgactc aagcgaaagc gccgcaaggt ccgagctcga tccaaataag cggtttttaa  11580
cggagattta acactaaatc gaagaacttt tcccgtttca tttgcgaatg agctcgttaa  11640
caaaatcccc cagttttttt atccagctgt aaggattgac attagtaatg aattattgtt  11700
tggtatattt aaatctgtag ttcctttctg tccgtgtcgg caactgtcgt actcgtgatt  11760
tacttgtatt gacgaatact tactgtagcg cactctgctg ctactggtcg taaggatgtg  11820
ctatttcggt gtatggtggg tttttggggg gtcggaaccg aagactgtta cacgggcacg  11880
```

gctcgttgtg tacacgcaca gagctcttgc gagtcatgtt gtagctagct cgtcgtgttc 11940
aggaactgtt cgatggttcg gagagagtcg ccgcccagaa catacgcgca ccgatgtcag 12000
cagacagcct tattacaagt atattcaagc aagtatatcc gtagggtgcg ggtgatttgg 12060
atctaaggtt cgtactcaac actcacgagc agcttgccta tgttacatcc ttttatcaga 12120
cataacataa ttggagttta cttacacacg gggtgtacct gtatgagcac cacctacaat 12180
tgtagcactg gtacttgtac aaagaattta ttcgtacgaa tcacagggac ggccgccctc 12240
accgaaccag cgaatacctc agcggtcccc tgcagtgact caacaaagcg atatgaacat 12300
cttgcgatgg tatcctgctg atagttttta ctgtacaaac acctgtgtag ctccttctag 12360
catttttaag ttattcacac ctcaagggga gggataaatt aaataaattc caaaagcgaa 12420
gatcgagaaa ctaaattaaa attccaaaaa cgaagttgga acacaacccc ccgaaaaaaa 12480
acaacaaaca aaaaacccaa caaaataaac aaaaacaaaa taaatatata actaccagta 12540
tctgactaaa agttcaaata ctcgtactta caacaaatag aaatgagccg gccaaaattc 12600
tgcagaaaaa aatttcaaac aagtactggt ataattaaat taaaaaacac atcaaagtat 12660
cataacgtta gttattttat tttatttaat aaaagaaaac aacaagatgg gctcaaaact 12720
ttcaacttat acgatacata ccaaataaca atttagtatt tatctaagtg cttttcgtag 12780
ataatggaat acaaatggat atccagagta tacacatgga tagtatacac tgacacgaca 12840
attctgtatc tctttatgtt aactactgtg aggcattaaa tagagcttga tatataaaat 12900
gttacatttc acagtctgaa cttttgcaga ttacctaatt tggtaagata ttaattatga 12960
actgaaagtt gatggcatcc ctaaatttga tgaaagatga aattgtaaat gaggtggtaa 13020
aagagctaca gtcgttttgt tttgagatac catcatctct aacgaaatat ctattaaaaa 13080
tctcagtgtg atcatgagtc attgccatcc tggaaaatgt catcatggct gatatttcta 13140
actgtttact tgagataaat atatatttac aagaacttcc cttgaaatta atttagatat 13200
aaaatgtttg cgggcaagtt actacgagga ataaattata tctaga 13246

<210> SEQ ID NO 13
<211> LENGTH: 20
<212> TYPE: DNA
<213> ORGANISM: Artificial Sequence
<220> FEATURE:
<223> OTHER INFORMATION: sequence used for Cas9 CRISPR targeting

<400> SEQUENCE: 13
acagcaggct gaacgaggat 20

<210> SEQ ID NO 14
<211> LENGTH: 20
<212> TYPE: DNA
<213> ORGANISM: Artificial Sequence
<220> FEATURE:
<223> OTHER INFORMATION: sequence used for Cas9 CRISPR targeting

<400> SEQUENCE: 14
tggaggcatg atcaacagcg 20

<210> SEQ ID NO 15
<211> LENGTH: 20
<212> TYPE: DNA
<213> ORGANISM: Artificial Sequence
<220> FEATURE:
<223> OTHER INFORMATION: sequence used for Cas9 CRISPR targeting -continued

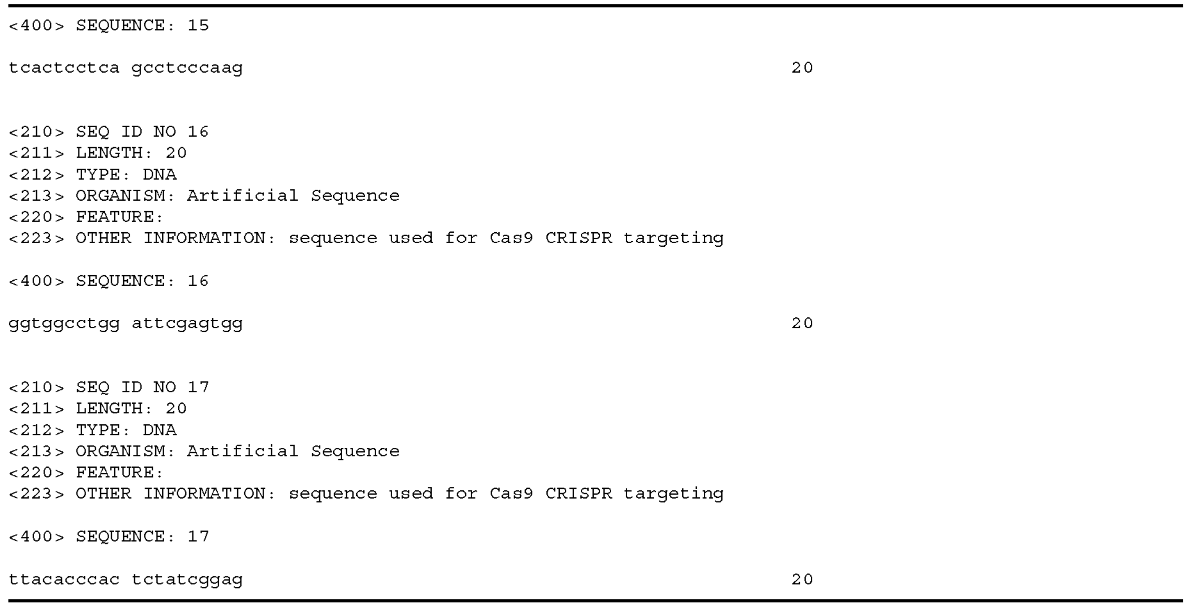

<400> SEQUENCE: 15
tcactcctca gcctcccaag 20

<210> SEQ ID NO 16
<211> LENGTH: 20
<212> TYPE: DNA
<213> ORGANISM: Artificial Sequence
<220> FEATURE:
<223> OTHER INFORMATION: sequence used for Cas9 CRISPR targeting

<400> SEQUENCE: 16
ggtggcctgg attcgagtgg 20

<210> SEQ ID NO 17
<211> LENGTH: 20
<212> TYPE: DNA
<213> ORGANISM: Artificial Sequence
<220> FEATURE:
<223> OTHER INFORMATION: sequence used for Cas9 CRISPR targeting

<400> SEQUENCE: 17
ttacacccac tctatcggag 20